US005990241A

United States Patent [19]

Emanuele et al.

[11] Patent Number: 5,990,241

[45] Date of Patent: *Nov. 23, 1999

[54] POLYOXYPROPYLENE/ POLYOXYETHYLENE COPOLYMERS WITH IMPROVED BIOLOGICAL ACTIVITY

[75] Inventors: R. Martin Emanuele, Hillbrook; Robert L. Hunter, Tucker; Paula H. Culbreth, Loganville, all of Ga.

[73] Assignee: CytRx, Corporation, Norcross, Ga.

[ * ] Notice: This patent issued on a continued prosecution application filed under 37 CFR 1.53(d), and is subject to the twenty year patent term provisions of 35 U.S.C. 154(a)(2).

[21] Appl. No.: 08/889,342

[22] Filed: Jul. 8, 1997

Related U.S. Application Data

[60] Continuation of application No. 08/657,161, Jun. 3, 1996, Pat. No. 5,691,387, which is a division of application No. 08/087,136, Jul. 2, 1993, Pat. No. 5,523,492, which is a continuation of application No. 07/847,874, Mar. 13, 1992, abandoned, which is a continuation-in-part of application No. 07/673,289, Mar. 19, 1991, abandoned.

[51] Int. Cl.[6] .......................... C07C 43/11; A61K 47/32
[52] U.S. Cl. ............................ 525/88; 525/89; 525/93; 568/624
[58] Field of Search .......................... 568/624; 514/723; 424/280.1; 524/505; 525/88, 89, 93

[56] References Cited

U.S. PATENT DOCUMENTS

| | | | |
|---|---|---|---|
| Re. 29,909 | 2/1979 | Kurtz | 568/624 |
| 2,674,619 | 4/1954 | Lundsted | 568/624 |
| 2,854,378 | 9/1958 | Buckwalter et al. | 568/624 |
| 2,979,528 | 4/1961 | Lundsted | 568/624 |
| 3,022,335 | 2/1962 | Lundsted | 568/624 |
| 3,036,118 | 5/1962 | Jackson et al. | 568/624 |
| 3,089,818 | 5/1963 | Stone | 568/624 |
| 3,140,232 | 7/1964 | Noseworthy | 568/624 |
| 3,228,834 | 1/1966 | Gans et al. | 568/624 |
| 3,391,196 | 7/1968 | Earing et al. | 568/624 |
| 3,450,502 | 6/1969 | Hymes | 568/624 |
| 3,577,522 | 5/1971 | Hymes | 568/624 |
| 3,590,125 | 6/1971 | Hymes | 568/624 |
| 3,641,240 | 2/1972 | Hymes et al. | 568/624 |
| 3,740,421 | 6/1973 | Schmolka | 568/624 |
| 3,867,521 | 2/1975 | Miskel et al. | 568/624 |
| 3,867,533 | 2/1975 | Schmolka | 568/624 |
| 3,956,259 | 5/1976 | Garcia et al. | 568/624 |
| 3,980,772 | 9/1976 | Ginger et al. | 568/624 |
| 4,073,886 | 2/1978 | Kehm | 568/624 |
| 4,100,271 | 7/1978 | Krezanoski | 568/624 |
| 4,104,455 | 8/1978 | Nagasawa | 568/624 |
| 4,179,337 | 12/1979 | Davis et al. | 568/624 |
| 4,186,253 | 1/1980 | Yokoyama et al. | 568/624 |
| 4,305,922 | 12/1981 | Rhodes | 568/624 |
| 4,323,560 | 4/1982 | Baschang et al. | 568/624 |
| 4,378,347 | 3/1983 | Franco | 568/624 |
| 4,395,393 | 7/1983 | Schmolka | 568/624 |
| 4,407,790 | 10/1983 | Oakes et al. | 568/624 |

(List continued on next page.)

FOREIGN PATENT DOCUMENTS

| | | |
|---|---|---|
| 0 000 704 | 7/1978 | European Pat. Off. . |
| 0003999 | 9/1979 | European Pat. Off. . |
| 0011237 | 5/1980 | European Pat. Off. . |
| 0 049 422 | 9/1981 | European Pat. Off. . |
| 0 103 290 | 9/1983 | European Pat. Off. . |
| 2081436 | 1/1971 | France . |
| 2708152 | 2/1977 | Germany . |
| 1183112 | 8/1985 | U.S.S.R. . |
| WO 87/06831 | 11/1987 | WIPO . |
| WO 87/06836 | 11/1987 | WIPO . |
| 90/07336 | 7/1990 | WIPO . |

OTHER PUBLICATIONS

Schmolka, I., "A Reivew of Block Polymer Surfactants," *Journal of the American Oil Chemists Society*, 54, No. 3, pp. 110–116 (1977).

Block and Graft Copolymerization, vol. 2, (ed. by R.J. Ceresa, John Wiley & Sons, 1976) "The Applications of Block Copolymer Polyol Surfactants," L.G. Lundsted and I.R. Schmolka; pp. 174–205 and pp. 255–272.

Reindorf, C.A., et al., "Perfluorocarbon Compounds: Effects on the Rheological Properties of Sickle Erythrocytes in vitro," *American Journal of Hematology*, vol. 19, pp. 229–236 (1985).

Padilla, F., et al., "Effect of Fluoricarbon Emulsions on the Mechanical Fragility of Normal and Sickle Cells: In Vitro Studies," *Federation Proceedings*, vol. 34, pp. 1510–1512 (1975).

Vercellotti, G.M., et al., "Activation of Plasma Complement by Perfluorocarbon Artificial Blood: Probable Mechanism of Adverse Pulmonary Reactions in Treated Patients and Rationale for Corticosteroid Prophylaxis," *Blood*, vol. 59, pp. 1299–1304 (1982).

Rodeheaver, G.T., "Pluronic® F–68: A Promising New Skin Wound Cleanser," *Ann Emerg Med*, 9:11, pp. 572–576 (1980).

Janoff, A.S., et al., "The Modification of Human Erythrocyte Membrane Structure by Membrane Stabilizers: An Electron Spin Resonance Study," *American Journal of Hematology*, vol. 10, pp. 171–179 (1981).

(List continued on next page.)

*Primary Examiner*—Joseph K. McKane
*Attorney, Agent, or Firm*—Jones & Askew, LLP

[57] ABSTRACT

The present invention comprises novel preparations of polyoxypropylene/polyoxyethylene copolymers which retain the therapeutic activity of the commercial preparations, but are substantially free from the undesirable effects which are inherent in the prior art preparations. Because the preparations of polyoxypropylene/polyoxyethylene copolymers which comprise the present invention are a less polydisperse population of molecules than the prior art polyoxypropylene/polyoxyethylene copolymers, the biological activity of the copolymers is better defined and more predictable.

176 Claims, 20 Drawing Sheets

U.S. PATENT DOCUMENTS

| | | | |
|---|---|---|---|
| 4,409,209 | 10/1983 | Baschang et al. | 568/624 |
| 4,410,660 | 10/1983 | Straus | 568/624 |
| 4,423,038 | 12/1983 | Baschang et al. | 568/624 |
| 4,489,158 | 12/1984 | Straus | 568/624 |
| 4,575,484 | 3/1986 | Straus | 568/624 |
| 4,600,652 | 7/1986 | Solomon et al. | 568/624 |
| 4,606,918 | 8/1986 | Allison et al. | 568/624 |
| 4,609,546 | 9/1986 | Hiratani | 568/624 |
| 4,764,567 | 8/1988 | Ott | 568/624 |
| 4,801,452 | 1/1989 | Hunter et al. | 568/624 |
| 4,803,070 | 2/1989 | Cantrell et al. | 568/624 |
| 4,806,352 | 2/1989 | Cantrell | 568/624 |
| 4,837,014 | 6/1989 | Hunter et al. | 568/624 |
| 4,837,083 | 6/1989 | Hunter et al. | 568/624 |
| 4,879,109 | 11/1989 | Hunter | 568/624 |
| 4,897,263 | 1/1990 | Hunter | 568/624 |
| 4,937,070 | 6/1990 | Hunter | 568/624 |
| 4,997,644 | 3/1991 | Hunter | 568/624 |
| 5,017,370 | 5/1991 | Hunter et al. | 568/624 |
| 5,028,599 | 7/1991 | Hunter | 568/624 |
| 5,030,448 | 7/1991 | Hunter | 568/624 |
| 5,032,394 | 7/1991 | Hunter | 568/624 |
| 5,039,520 | 8/1991 | Hunter | 568/624 |
| 5,041,288 | 8/1991 | Hunter | 568/624 |
| 5,047,236 | 9/1991 | Hunter et al. | 568/624 |
| 5,057,540 | 10/1991 | Kensil et al. | 568/624 |
| 5,064,643 | 11/1991 | Hunter et al. | 568/624 |
| 5,071,649 | 12/1991 | Hunter | 568/624 |
| 5,078,995 | 1/1992 | Hunter et al. | 568/624 |
| 5,080,894 | 1/1992 | Hunter et al. | 568/624 |
| 5,089,260 | 2/1992 | Hunter et al. | 568/624 |
| 5,198,211 | 3/1993 | Hunter et al. | 568/624 |
| 5,250,294 | 10/1993 | Hunter et al. | 568/624 |
| 5,294,365 | 3/1994 | Welch et al. | 568/624 |
| 5,340,916 | 8/1994 | Henn et al. | 568/624 |
| 5,371,253 | 12/1994 | Cooper | 568/624 |
| 5,523,492 | 6/1996 | Emanuele et al. | 568/624 |

OTHER PUBLICATIONS

Moore, A.R., et al., "Reduction of Splenic Vascular Resistance During Profusion by Pluronic® F–68," *Journal of Surgical Research,* vol. 8, pp. 563–566 (1968).

Benner, K.U., et al., "Cold–Induced Platelet Aggregation In Vivo And Its Inhibition By A Nonionic Surface Active Substance," *Thrombosis Research,* vol. 2, pp. 331–342 (1973).

Hymes, A.C., et al., "The Influence Of An Industrial Surfactant Pluronic® F–68, In The Treatment of Hemorrhagic Shock," *Journal of Surgical Research,* Vol. 11, pp. 191–197 (1971).

Hoie, J., et al., "Effects of Pluronic® F68, Poloralkol, On Vascular Resistance In Vivo," *Journal of Surgical Research,* vol. 11, pp. 515–517 (1971).

Grover, F.L., et al., "A Nonionic Surfactant And Blood Viscosity," *Arch Surg.,* vol. 106, pp. 307–310 (1973).

Grover, F.L., et al., "The Effect of Pluronic® F–68 On Circulatory Dynamics And Renal And Carotid Artery Flow During Hemorrhagic Shock," *Journal of Surgical Research,* vol. 17, pp. 30–35 (1974).

Ketchum, L.D., et al., "Experimental Use of Pluronic® F–68 In Microvascular Surgery,"*Plastic and Reconstructive Surgery,* vol. 53, pp. 288–292 (1974).

Ketchum, L.D., "Pharmacological alternations in the clotting mechanism: Use in microvascular surgery,"*Journal of Hand Surgery,* vol. 3, pp. 407–415 (1978).

Vasko, K.A., et al., "Poloxalkol® (Pluronic F–68): A priming solution for cardiopulmonary bypass," *Trans. Am. Soc. Artif. Int. Organs,* 18, pp. 526–531 (1972).

Block, N.L., et al., "Acutely Traumatized Canine Ureter, Effects of Low Molecular Weight Dextran and Surfactant Pluronic F–68," *Urology,* vol. III, pp. 190–194 (1974).

Knize, D.M., et al., "Use of antisludging agents in experimental cold injuries," *Surgery, Gynecology & Obstetrics,* vol. 129, pp. 1019–1026 (1969).

Organ Perfusion and Preservation, (ed. by Norman, J.C., Appleton–Century–Crofts, (1968)), Paton, B.C., et al., "The use of a nonionic detergent added to organ perfusates," pp. 105–120.

Smillie, J.A., et al., "Cryopreservation of Human Platelets with Polyvinylpyrrolidone," *Transfusion,* vol. 21, pp. 552–556 (1981).

Gaehtgens, P., et al., "Desaggregation of Human Red Blood Cells by Various Surface–Active Agents as Related to Changes of Cell Shape and Hemolysis," *Act Heamat,* vol. 33, pp. 82–89 (1975).

Advances in Blood Substitute Research (ed. by Bolin, et al., Alan R. Liss, Inc. New York (1983)) Sugi, et al., The Use of Fluosol–DA (FDA) in Emergency Situations: A Report of 67 Clinical Cases, Abstract/451.

Lane, T.A., et al., "Reduction in the Toxicity of a Component of an Artificial Blood Substitute by supercritical fluid fractionation," *Transfusion,* vol. 28, pp. 375–378 (1987).

Lane, T.A., et al., "Paralysis of Phagocyte Migration Due to an Artificial Blood Substitute," *Blood,* vol. 64, pp. 400–405 (1984).

Spiess, B.D., et al., "Protection from Cerebral Air Emboli with Perfluorocarbons in Rabbits," *Stroke,* vol. 17, pp. 1146–1149 (1986).

Kanter, K.R., et al., "Superiority of Perfluorocarbon Cardioplegia over Blood or Crystalloid Cardioplegia," *Circulation,* vol. 64, pp. II–75–II–80 (1981).

Harjula, A., et al., "Perfluorocarbon solution as a myocardial preservative," *J. Applied Cardiology,* vol. 2, pp. 121–136 (1987).

Tokioka, M.D., et al., "Effects of intracoronary infusion of arterial blood or Fluosol–DA 20% on regional myocardial metabolism and function during brief coronary artery occlusions," *Laboratory Investigation,* vol. 75, pp. 473–481 (1987).

Benner, K.U., et al., "Uber die Wirkung von Pluronic® F68, einem polyoxypropylen–Polyoxyäthylen–Kondensat, auf die ADP–induzierte Thrombocytenaggregation in vitro," *Pflügers Arch.,* vol. 315, pp. 45–52 (1970).

Forman, M.B., et al., "Reduction of Infarct Size with Intracoronary Perfluorochemical in a Canine Preparation of Reperfusion," *Circulation,* vol. 71, pp. 1060–1068 (1985).

Forman, M.B., et al., "Beneficial Long–Term Effect of Intracoronary Perfluorochemical on Infarct Size and Ventricular Function in a Canine Reperfusion Model," *J. Am. Col. of Cardiol.,* pp. 1082–1090 (May 1987).

Goodman, R.L., et al., "Perfluorocarbon Emulsions in Cancer Therapy: Preliminary Observations on Presently Available Formulations," *Int. J. Radiation Oncology Biol. Phys.,* vol. 10, pp. 1421–1424 (1984).

Grover et al., "A Nonionic Surfactant and Blood Viscosity— Experimental Observations," *Arch. Surg.,* vol. 106, pp. 307–310 (Mar., 1973).

Connaghan et al., Specific Identification of Fibrin Polymers, Fibrinogen Degradation Products, and Crosslinked Fibrin Degration Products in Plasma and Serum With a New Sensitive Technique, *Blood,* vol. 65, No. 3, pp. 589–597 (Mar., 1985).

Atkinson, T.P., et al., "Ion transport mediated by copolymers composed of polyoxyethylene and polyoxypropylene," *The American Physiological Society,* 0363–6143/88, pp. C20–C26 (1988).

Wiman et al., "Determination of Soluble Fibrin in Plasma by a Rapid and Quantitative Spectrophotometric Assay," *Thrombosis and Haemostasos,* F.K. Schattauer Verlag GmbH (Stuttgart) 55 (2), pp. 18–193 (1986).

Hunter, R.L., et al., "The Adjuvant Activity of Nonionic Block Polymer Surfactants. III. Characterization of Selected Biologically Active Surfaces," *Scand. J. Immunol.,* vol. 23, pp. 287–300 (1986).

Perfluorochemmical Blood Substitues, Technical Information Ser. No. 5, Jun. 30, 1978, Revised, Jul. 1, 1981, Manufacturer: The Green Cross Corporation.

Heron, M.W., et al., "A Method for Measuring a Nonionic Surface–Active Agent (Pluronic F–68) in Biological Fluids," *Analytical Biochemistry,* vol. 24, pp. 491–495 (1968).

Uno, T., et al., "Determination of Surface–Active Agents. VIII. Infrared Determination of the Proportion of Ethylene Oxide and Propylene Oxide in Pluronic," *Chem. Pharm. Bull.,* vol. 15(1), pp. 77–82 (1967).

Hymes, A.C., et al., "Influence of an Industrial Surfactant (Pluronic F–68) on Human Amniotic Fluid Embolism," *American Journal Obstetrics and Gynecology,* vol. 107(8), pp. 1217–1222 (Aug. 15, 1970).

Grover, F.L., et al., "Beneficial Effect of Pluronic F–68 on the Microcirculation in Experimental Hemorrhagic Shock," *Surgical Forum,* vol. 21, pp. 30–32 (1970).

Maugh, T.H., "Perfluorochemical Emulsions: Promising Blood Substitutes," *Science,* vol. 179, pp. 669–672 (1973).

Justice, C., et al., "Prevention of Thrombosis with Agents which Reduce Platelet Adhesiveness," *The American Surgeon,* vol. 40, pp. 186–189 (1974).

Danielson, G., et al., "Use of Pluronic F–68 to Diminish Fat Emboli and Hemolysis During Cardiopulmonary Bypass," *The Journal of Thoracic and Carrdiovascular Surgery,* vol. 59(2), pp. 178–184 (1970).

Ketchum, L.D., "Experimental Use of Pluronic F68 in Microvascular Surgery," *Plastic Reconstructive Surgery,* vol. 54, p. 478 (1974).

Hunter, R., "Adjuvant Activity of Non–ionic Block Copolymers. IV. Effect of Molecular Weight and Formulation on Titre and Isotype of Antibody," *Vaccine,* vol. 9, pp. 250–256 (Apr. 1991).

Byars, N.E., et al., "Adjuvant formulation for use in vaccines to elicit both cell–mediated and humoral immunity," *Vaccine,* vol. 5, pp. 223–228 (Sep. 1987).

Hunter, et al., "The Adjuvant Activity of Nonionic Block Polymer Surfactants I. The role of Hydrophile–Lipophile Balance," *J. of Immunology,* vol. 127, No. 3, pp. 1244–1250 (1981).

Hunter, R.L., et al., "The Adjuvant Activity of Nonionic Block Polymer Surfactants II. Antibody Formulation and Infammation Related to the Structure of Triblock and Octablock Copolymers," *J. of Immunology.,* vol. 133, No. 6, pp. 3167–3175 (1984).

Hunter, R.L., et al., "Nonionic Block Copolymer Surfactants as Immunological Adjuvants: Mechanisms of Action and Novel Formulations," *Immunological Adjuvants and Vacines,* ed. by Gregoriadis, G., et al., Plenum Publishing Corp., pp. 133–144 (1989).

Cornforth, et al., "Antituberculosis Effect of Certain Surface–Active Polyoxyethylene Ethers in Mice," *Nature,* vol. 168, pp. 150–153 (1951).

Lin, T.S., et al., "Synthesis and Biological Activity of Several Amio Analogs of Thymidine," *J. Med. Chem.,* vol. 21, pp. 109–112 (1978).

McDougal, J.S., et al., "Immunoassay for the detection and Quantitation of infectious human retrovirus, lymphadenopathy–associated virus (LAV)," *J. Immun. Meth.,* vol. 76, pp. 171–183 (1985).

Groopman, J.E., et al., "Characterization of serum neutralization response to the human immunodeficiency virus (HIV)," *AIDS Res. Human Retro.,* vol. 3, pp. 71–85 (1987).

Spira, et al., "Micromethod for assaying the reverse transcriptase of LAV–HTLV–III/lymphadenopathy–associated virus," *J. Clin. Microbiol.,* vol. 25, pp. 97–99 (1987).

Schinazi, R.F., et al., "Combinations of Isoprinosine and 3'–Azido–3'–Deoxythymidine in Lymphocytes Infected with Human Immunodificiency Virus Type 1," *Antimicrob. Agents Chemother.,* vol. 32, pp. 1784–1789 (1988).

Schinazi, R.F., et al., "Effect of combination of acyclovir, and vidarabine or its 5'–monophosphate on herpes simplex viruses in cell culture and in mice," *Antimicrob. Agents Chemother.,* vol. 22, pp. 499–507 (1982).

Chou, T.C., et al., "Quantitative analysis of dose–effect relationships: the combined effects of multiple drugs or enzyme inhibitors," *Adv. Enz. Regul.,* vol. 22, pp. 27–55 (1984).

Weintraub, H.M., "Antisense RNA and DNA," *Scientific American,* pp. 40–46 (Jan. 1990).

Schmolka, I.R., et al., "Artificial Skin I. Preparation and Properties of Pluronic F–127 Gels for Treatment of Burns," *J. Biomed. Mater. Res.,* vol. 6, pp. 571–582 (1972).

Snippe, H., et al., "Adjuvant Effect of Nonionic Block Polymer Surfactants in Humoral and Cellular Immunity," *Int. Archs. Allergy Appl. Immun.,* vol. 65, pp. 390–398 (1981).

Takayama, K., et al., "Adjuvant activity of non–ionic block copolymers. V. Modulation of antibody isotype by lipopolysaccharides, lipid A and precursors," *Vaccine,* vol. 9, pp. 257–265 (Apr. 1991).

Williams, J.H., et al., "Modulation of Rat Granulocyte Traffic by a Surface Active Agent in Vitro and Bleomycin Injury," *Proceedings of the Society for Experimental Biology and Medicine,* vol. 188, pp. 461–470 (1988).

Matsukura, M., et al., "Phosphorothioate analogs of oligodeoxynucleotides: Inhibitors of replication and cytopathic effects of human immunodeficiency virus," *Proc. Natl. Acad. Sci.,* vol. 84, pp. 7706–7710 (Nov., 1987).

Rodeheaver, et al., "Mechanical Cleansing of Contaminated Wounds with Surfactant," *Am. J. Surg.,* vol. 129, No. 3, pp. 241–245 (1975).

Database WPI, Derwent Publications Ltd., London, GB; AN 82–1478IE(08) & JP–A–57 008 223 (mitsui Petrochem.) Jan. 17, 1982.

Schick, M.J., *Non–ionic Surfactants.* Marcel Dekker Inc., New York, pp. 893–920 (1967).

Davis, B.D., M.D., et al., *Microbiology: Indluding Immunology and Molecular Genetics.* Third Edition, Harper & Row Publishers, Cambridge, pp. 740–741 and 842–843 (1980).

Crémieux, A., et al., "Methods of Testing Disinfectants," *Disinfection, Sterilization, and Preservation,* Block, S.S., ed., Lea & Febiger Publishers, Philadelphia, pp. 918–925, 940 (1983).

Hunter, et al., "Increased Whole Blood Viscosity During Coronary Bypass Surgery," *Thromb. Haemost.,* vol. 63, No. 1, pp. 6–12 (Feb. 19, 1990).

Kondo, et al., "Prolonged Suspended Animation in Puppies," *Cryobiology,* vol. 11, No. 5, pp. 446–451 (1974).

Mezrow, et al., "Poloxamer 188 improves neurologic outcome after hypothermic circulatory arrest," *J. Thorac. Cardiovasc. Surg.,* vol. 103, No. 6, pp. 1143–1146 (Jun., 1992).

Nagata, et al. "Clinical evaluation on the effect of Poloxamer 188 on the hemolysis during cardiopulmonary bypass," *J. Aichi, Med. Univ. Assoc.,* vol. 11, No. 1, pp. 48–54 (1983).

Papadea, et al., "Effect of RheothRx (TM) Copolymer on Blood Viscosity Related to Fibrin(ogen) Concentration," *FASEB J.,* vol. 2, No. 4, p. A384A, abstract 512 (Mar. 15, 1988).

Richard, M.N., et al., "Effect of Lysine and Wettig Agents on Activated Plasinogen Solutions," *Canadian Journal of Biochemistry & Physiology,* vol. 41, pp. 211–217 (1963).

Sakauchi, "Prevention of Excess Hemolysis During Cardiopulmonary Bypass by the Use of Pluronic F–68," *Kitakanto Med. J.,* vol. 23, No. 3, pp. 231–238 (1973).

Fig_5

Fig_6

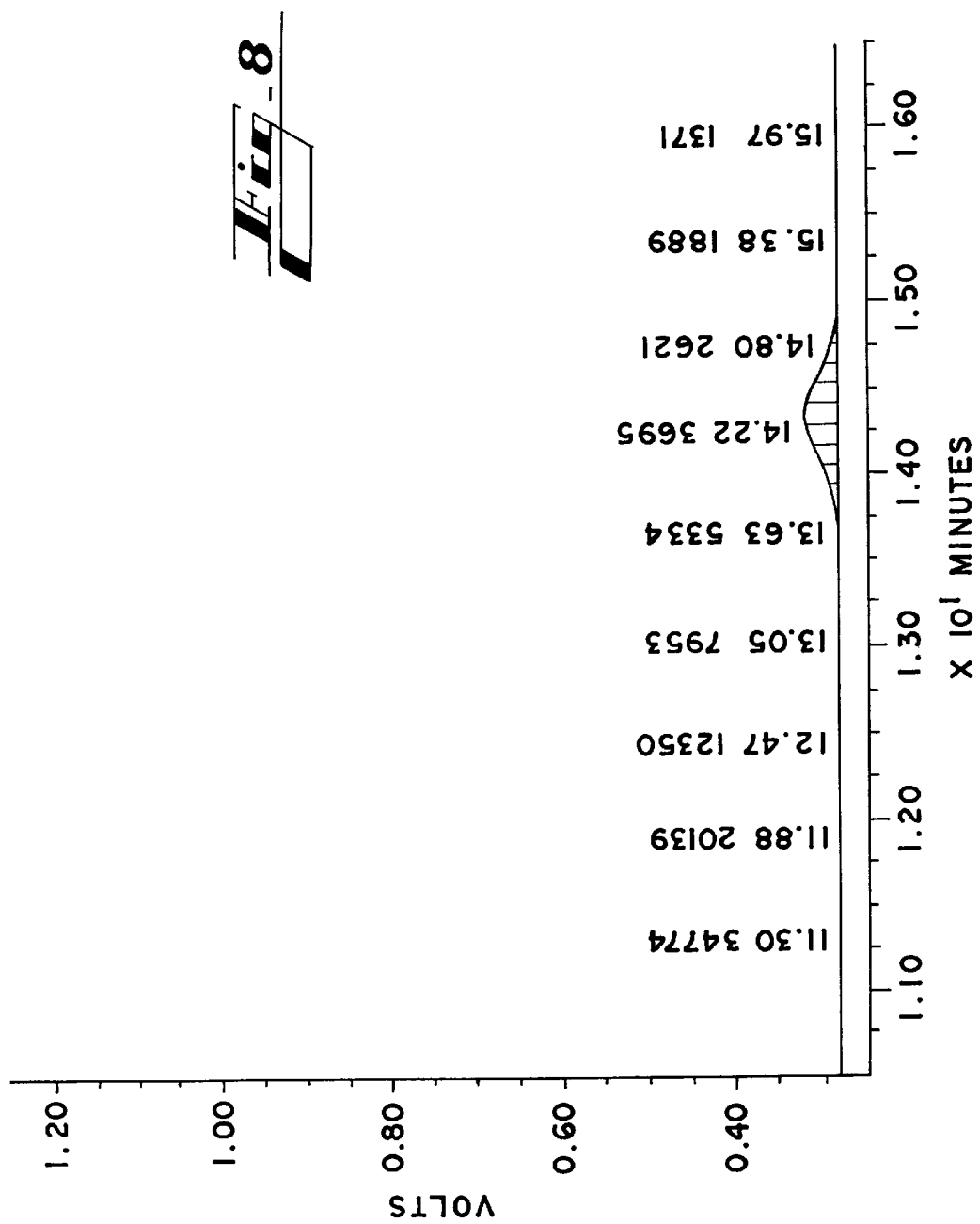

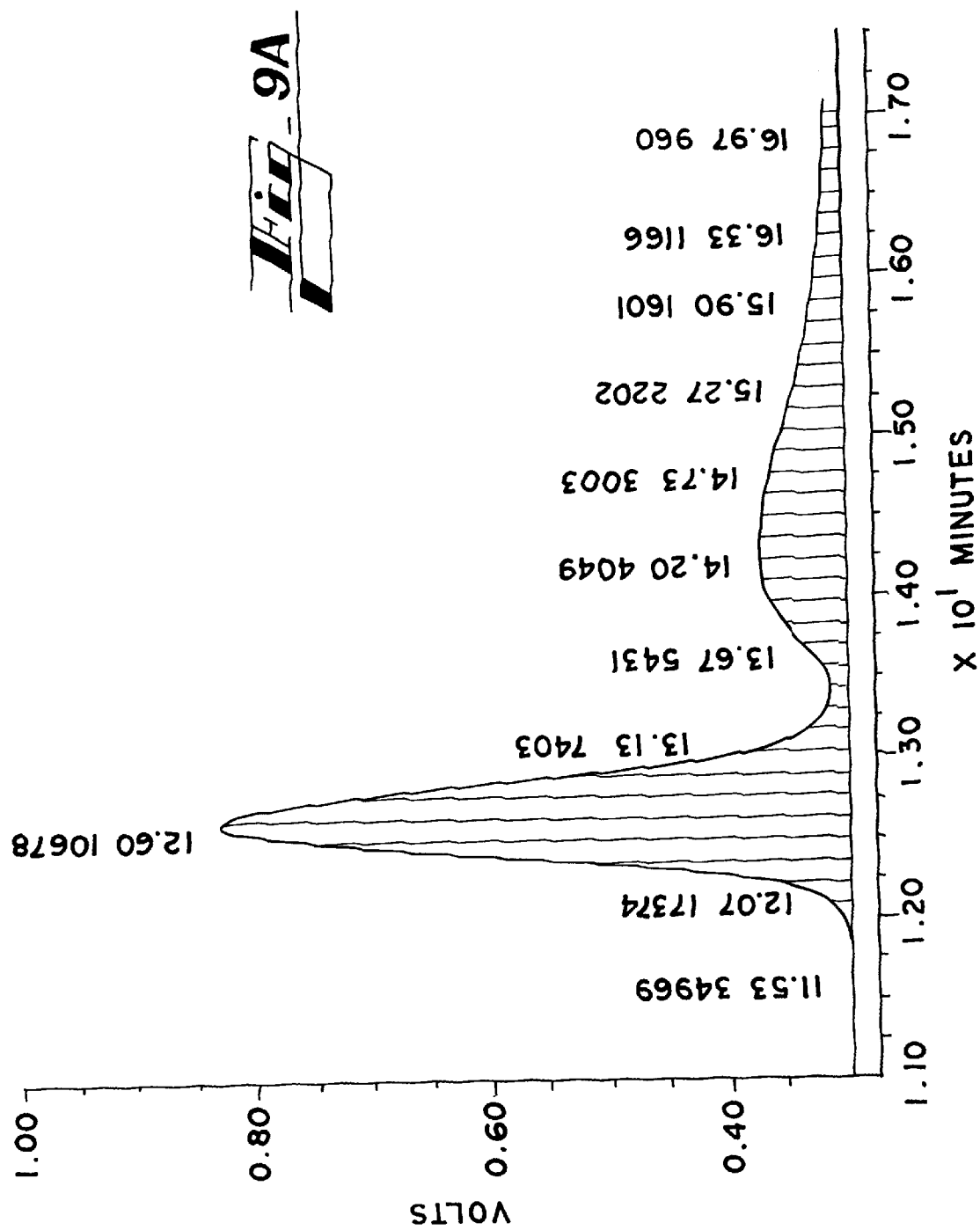

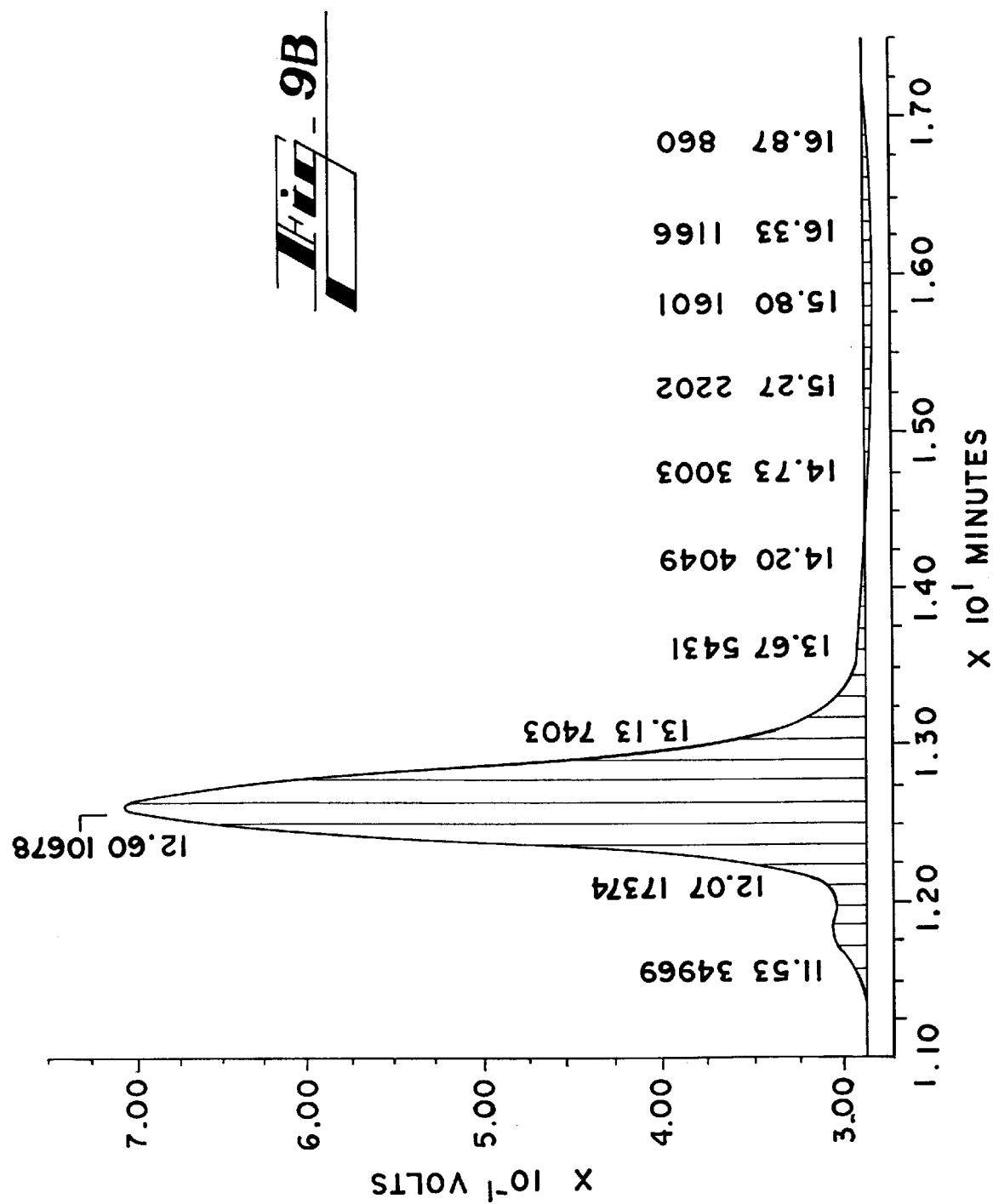

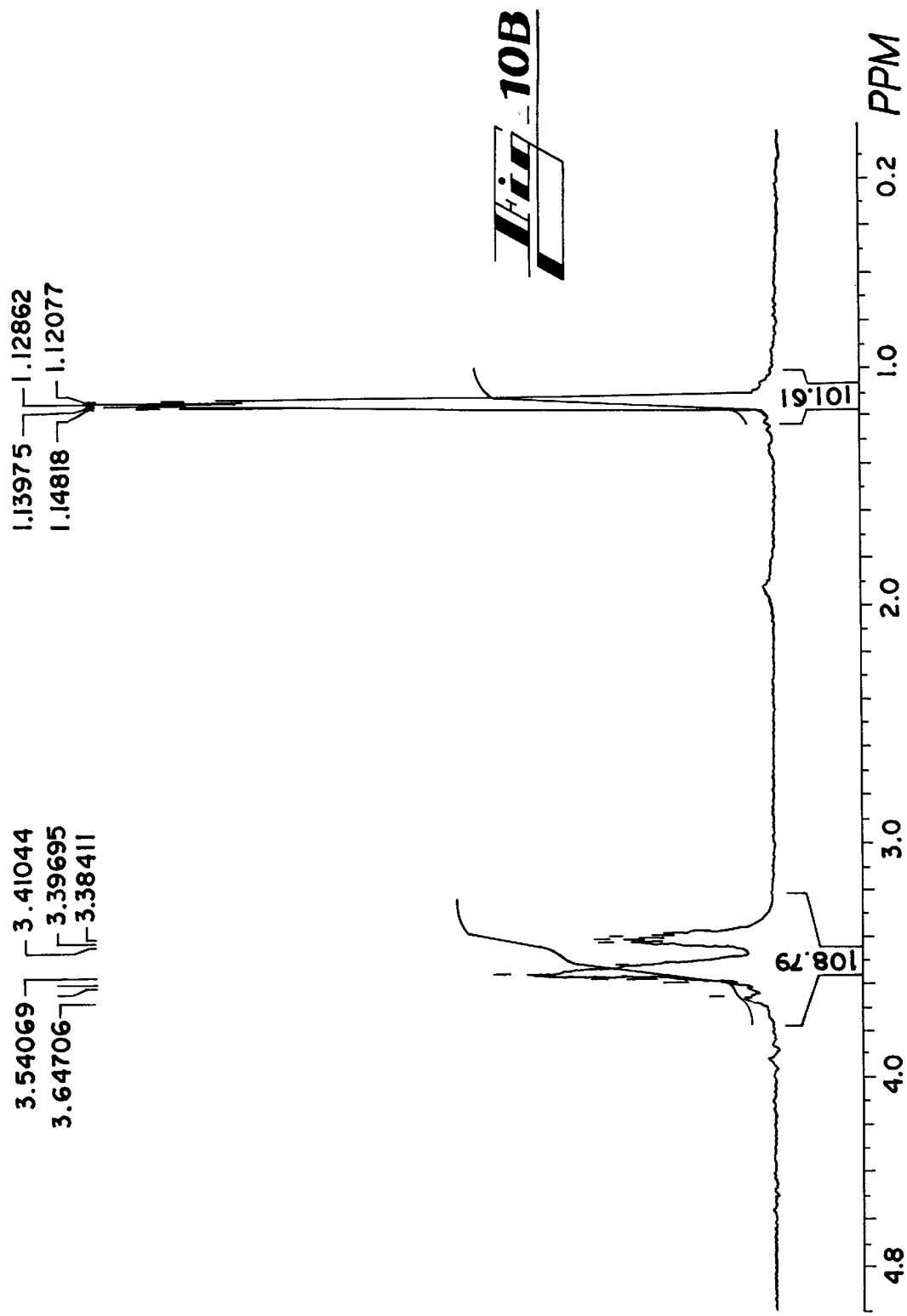

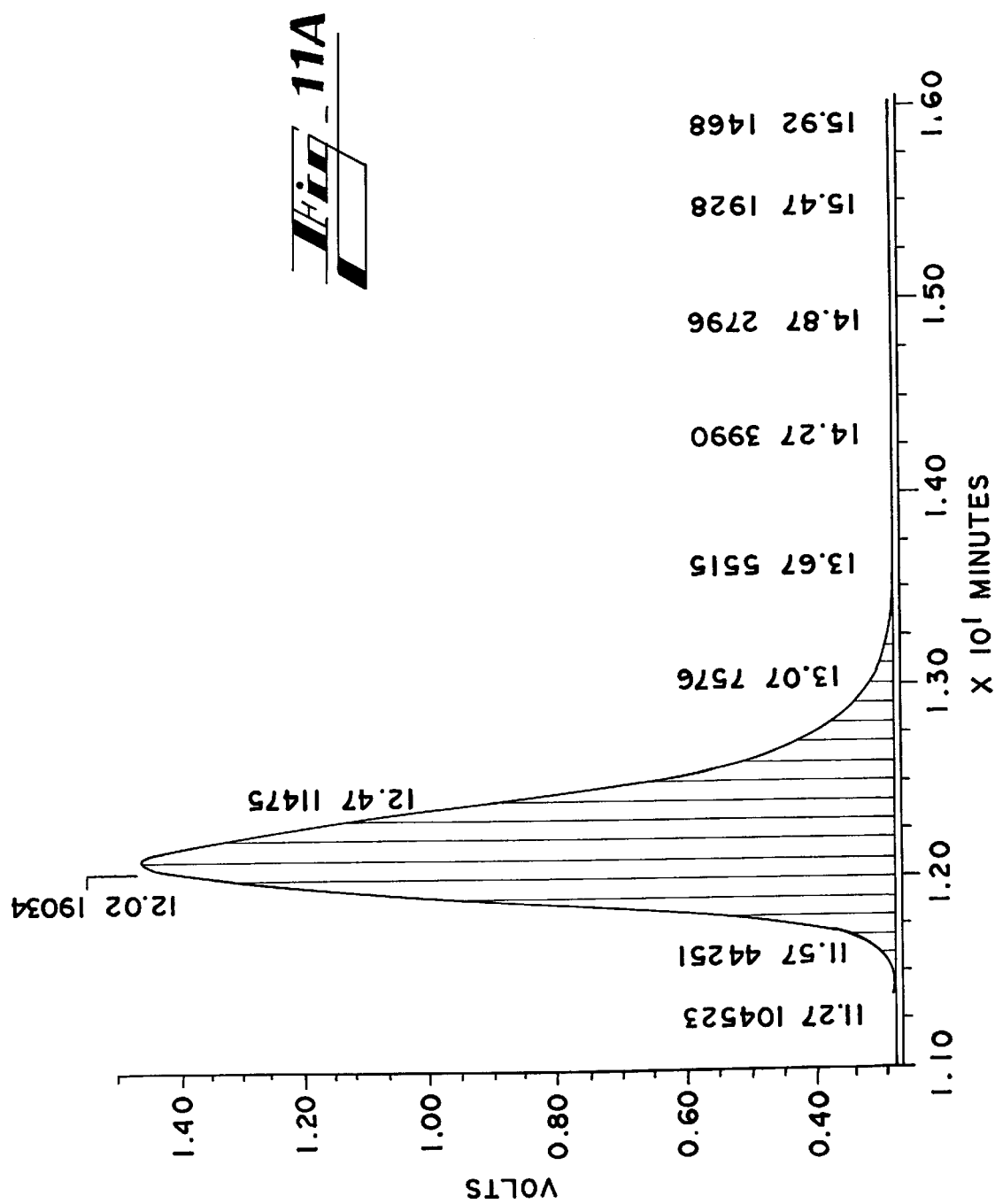
Fig_11A

POLYOXYPROPYLENE/ POLYOXYETHYLENE COPOLYMERS WITH IMPROVED BIOLOGICAL ACTIVITY

CROSS-REFERENCE TO RELATED APPLICATIONS

This application is a continuation of application Ser. No. 08/657,161, filed Jun. 3, 1996 now U.S. Pat. No. 5,699,387, of application Ser. No. 08/087,136, filed Jul. 2, 1993, now U.S. Pat. No. 5,523,490, which is a continuation of Ser. No. 07/847,874 filed Mar. 13, 1992, now abandoned which is a continuation-in-part of U.S. patent application Ser. No. 07/673,289, filed Mar. 19, 1991, now abandoned.

TECHNICAL FIELD

The present invention relates to a preparation of polyoxypropylene/polyoxyethylene copolymer which has an improved toxicity and efficacy profile. The present invention also includes polyoxypropylene/polyoxyethylene block copolymers with a polydispersity value of less than approximately 1.05.

BACKGROUND OF THE INVENTION

Certain polyoxypropylene/polyoxyethylene copolymers have been found to have beneficial biological effects when administered to a human or animal. These beneficial biological effects are summarized as follows:

Polyoxypropylene/polyoxyethylene Copolymers as Rheologic Agents

The copolymers can be used for treating circulatory diseases either alone or in combination with other compounds, including but not limited to, fibrinolytic enzymes, anticoagulants, free radical scavengers, antiinflammatory agents, antibiotics, membrane stabilizers and/or perfusion media. These activities have been described in U.S. Pat. Nos. 4,801,452, 4,873,083, 4,879,109, 4,837,014, 4,897,263, 5,064,643; 5,028,599; 5,047,236; 5,089,260; 5,017,370; 5,078,995; 5,032,394; 5,041,288; 5,071,649; 5,039,520; 5,030,448; 4,997,644; 4,937,070; 5,080,894; and 4,937,070, all of which are incorporated herein by reference.

The polyoxypropylene/polyoxyethylene copolymers have been shown to have quite extraordinary therapeutic activities. The surface-active copolymers are useful for treating pathologic hydrophobic interactions in blood and other biological fluids of humans and animals. This includes the use of a surface-active copolymer for treatment of diseases and conditions in which resistance to blood flow is pathologically increased by injury due to the presence of adhesive hydrophobic proteins or damaged membranes. This adhesion is produced by pathological hydrophobic interactions and does not require the interaction of specific ligands with their receptors. Such proteins and/or damaged membranes increase resistance in the microvasculature by increasing friction and reducing the effective radius of the blood vessel. It is believed that the most important of these proteins is soluble fibrin.

Pathological hydrophobic interactions can be treated by administering to the animal or human suffering from a condition caused by a pathological hydrophobic interaction an effective amount of a surface-active copolymer. The surface-active copolymer may be administered as a solution by itself or it may by administered with another agent, including, but not limited to, a fibrinolytic enzyme, an anticoagulant, or an oxygen radical scavenger.

The method described in the foregoing patents comprises administering to an animal or human an effective amount of a surface-active copolymer with the following general formula:

$$HO(C_2H_4O)_b(C_3H_6O)_a(C_2H_4O)_bH$$

wherein a is an integer such that the hydrophobe represented by $(C_3H_6O)$ has a molecular weight of approximately 950 to 4000 daltons, preferably about 1200 to 3500 daltons, and b is an integer such that the hydrophile portion represented by $(C_2H_4O)$ constitutes approximately 50% to 95% by weight of the compound.

A preferred surface-active copolymer is a copolymer having the following formula:

$$HO(C_2H_4O)_b(C_3H_6O)_a(C_2H_4O)_bH$$

wherein the molecular weight of the hydrophobe $(C_3H_6O)$ is approximately 1750 daltons and the total molecular weight of the compound is approximately 8400 daltons.

The surface-active copolymer is effective in any condition where there is a pathological hydrophobic interaction between cells and/or molecules. These interactions are believed to be caused by 1) a higher than normal concentration of fibrinogen, 2) generation of intravascular or local soluble fibrin, especially high molecular weight fibrin, 3) increased friction in the microvasculature, or 4) mechanical or chemical trauma to blood components. All of these conditions cause an increase in pathological hydrophobic interactions of blood components such as cells and molecules.

It is believed that fibrin, especially soluble fibrin, increases adhesion of cells to one another, markedly increases friction in small blood vessels and increases viscosity of the blood, especially at low shear rates. The effects of the surface-active copolymer are believed to be essentially lubrication effects because they reduce the friction caused by the adhesion.

Although not wanting to be bound by the following hypothesis, it is believed that the surface-active copolymer acts according to the following mechanism: Hydrophobic interactions are crucial determinants of biologic structure. They hold the phospholipids together in membranes and protein molecules in their native configurations. An understanding of the biology of the surface-active copolymer is necessary to appreciate the biologic activities of the compound. Water is a strongly hydrogen bonding liquid which, in its fluid state, forms bonds in all directions with surrounding molecules. Exposure of a hydrophobic surface, defined as any surface which forms insufficient bonds with water, produces a surface tension or lack of balance in the hydrogen bonding of water molecules. This force can be exceedingly strong. The surface tension of pure water is approximately 82 dynes/cm. This translates into a force of several hundred thousand pounds per square inch on the surface molecules.

As two molecules or particles with hydrophobic surfaces approach, they adhere avidly. This adhesion is driven by the reduction in free energy which occurs when water molecules transfer from the stressed non-hydrogen bonding hydrophobic surface to the non-stressed bulk liquid phase. The energy holding such surfaces together, the work of adhesion, is a direct function of the surface tension of the particles:[1]

$$W_{AB} = \gamma A + \gamma B - \gamma AB$$

where $W_{AB}$=work of adhesion or the energy necessary to separate one square centimeter of particle interface AB into two separate particles, $\gamma A$ and $\gamma B$ are the surface tensions of particle A and particle B, $\gamma AB$ the interfacial tension between them.

Consequently, any particles or molecules in the circulation which develop significant surface tensions will adhere to one another spontaneously. Such adhesion within membranes and macromolecules is necessary to maintain their integrity. We use the term "normal hydrophobic interaction" to describe such forces. Under normal circumstances, all cells and molecules in the circulation have hydrophilic non-adhesive surfaces. Receptors and ligands which modulate cell and molecular interactions are generally located on the most hydrophilic exposed surfaces of cells and molecules where they are free to move about in the aqueous media and to interact with one another. Special carrier molecules are necessary to transport lipids and other hydrophobic substances in the circulation. In body fluids such as blood, nonspecific adhesive forces between mobile elements are extremely undesirable. These forces are defined as "pathologic hydrophobic interactions"=0 because they restrict movement of normally mobile elements and promote inappropriate adhesion of cells and molecules.

In damaged tissue, hydrophobic domains normally located on the interior of cells and molecules may become exposed and produce pathologic adhesive surfaces whose interaction compounds the damage. Fibrin deposited along vessel walls also provide an adhesive surface. Such adhesive surfaces appear to be characteristic of damaged tissue. It is believed that the ability of the surface-active copolymer to bind to adhesive hydrophobic surfaces and convert them to non-adhesive hydrated surfaces closely resembling those of normal tissues underlies its potential therapeutic activities in diverse disease conditions.

Adhesion due to surface tension described above is different from the adhesion commonly studied in biology. The commonly studied adhesion is due to specific receptor ligand interactions. In particular, it is different from the receptor-mediated adhesion of the fibrinogen—von Willibrands factor family of proteins.[2]

Both the hydrophilic and hydrophobic chains of the surface-active copolymer have unique properties which contribute to biologic activity. The hydrophilic chains of polyoxyethylene (POE) are longer than those of most surfactants and they are flexible. They bind water avidly by hydrogen bond acceptor interactions with ether-linked oxygens. These long, strongly hydrated flexible chains are relatively incompressible and form a barrier to hydrophobic surfaces approaching one another. The hydroxyl moieties at the ends of the molecule are the only groups capable of serving as hydrogen bond donors. There are no charged groups.

This extremely limited repertoire of binding capabilities probably explains the inability of the molecule to activate host mediator and inflammatory mechanisms. The POE chains are not necessarily inert, however. Polyoxyethylene can bind cations by ion-dipole interactions with oxygen groups. The crown polyethers and reverse octablock copolymer ionophores are examples of such cation binding.[3] It is possible that the flexible POE chains form configurations which bind and modulate calcium and other cation movements in the vicinity of damaged membranes or other hydrophobic structures.

The hydrophobic component of the surface-active copolymer is large, weak and flexible. The energy with which it binds to a cell membrane or protein molecule is less than the energy which holds the membrane phospholipids together or maintains the tertiary conformation of the protein. Consequently, unlike common detergents which dissolve membrane lipids and proteins, the surface-active copolymer adheres to damaged spots on membranes and prevents propagation of the injury.

The ability of the surface-active copolymer to block adhesion of fibrinogen to hydrophobic surfaces and the subsequent adhesion of platelets and red blood cells is readily demonstrated in vitro. Most surfactants prevent adhesion of hydrophobic particles to one another, however, the surface-active copolymer has a unique balance of properties which optimize the anti-adhesive activity while minimizing toxicity. Thus, the surface-active copolymer is not routinely used by biochemists who use nonionic surfactants to lyse cells or dissolve membrane proteins. The surface-active copolymer protects cells from lysis. The hydrophobe effectively competes with damaged cells and molecules to prevent pathologic hydrophobic interactions, but cannot disrupt the much stronger normal hydrophobic interactions which maintain structural integrity.

The viscosity of blood is generally assumed to be the dominant determinant of flow through vessels with a constant pressure and geometry. In the smallest vessels, such as those in damaged tissue, other factors become significant. When the diameter of the vessel is less than that of the cell, the blood cell must deform in order to enter the vessel and then must slide along the vessel wall producing friction. The deformability of blood cells entering small vessels has been extensively studied[4] but the adhesive or frictional component has not. The adhesion of cells to vessel walls is generally attributed to specific interactions with von Willebrand's factor and other specific adhesive molecules.[5] Our data suggests that in pathologic situations, friction resulting from nonspecific physicochemical adhesion between the cell and the vessel wall becomes a major determinant of flow.

Mathematically, both the strength of adhesion between two particles and the friction force which resists sliding of one along the other are direct functions of their surface tensions which are largely determined by their degree of hydrophobic interaction. The friction of a cell sliding through a small vessel consists of an adhesion component and a deformation component[6] which are in practice difficult to separate:

$$F = Fa + Fd$$

where F is the friction of cells, Fa is the adhesion component and Fd is the deformation component.

The deformation component within a vessel differs from that required for entry into the vessel. It may be similar to that which occurs in larger vessels with blood flowing at a high rate of shear.[7] Friction within blood vessels has been studied very little, but undoubtedly involves the same principles which apply to polymer systems in which the friction force correlates directly with the work of adhesion:[8]

$$Fa = k\ WA + c$$

where Fa is the adhesional component of the friction force, WA the work of adhesion, and k and c constants which pertain to the particular system studied. Many lubricants act as thin films which separate the two surfaces and reduce adhesion.[9]

The effects of the surface-active copolymer on microvascular blood flow were evaluated in several models ranging from artificial in vitro systems where critical variables could be rigidly controlled to in vivo systems mimicking human disease. First, the surface-active copolymer can be an effective lubricant when used at therapeutic concentrations in a model designed to simulate movement of large cells through small vessels. It markedly reduced the adhesive component of friction, but had no detectable effect on the deformation component of friction. Second, the surface-active copolymer greatly accelerates the flow through the narrow channels formed by the thrombogenic surfaces of glass and air. A drop of blood was placed on a cover slip and viewed under a microscope with cinemicroscopy during the time it took the blood to flow to the edges of the cover slip in response to gentle pressure. The surface-active copolymer inhibited the adhesion of platelets to the glass and maintained the flexibility of red cells which enabled them to pass through the microscopic channels. While the surface-active copolymer did not inhibit the formation of rouleaux by red cells, it did cause the rouleaux to be more flexible and more easily disrupted. Third, the surface-active copolymer increases the flow of blood through tortuous capillary-sized fibrin-lined channels by over 20-fold. It decreased viscosity of the blood by an amount (10%) far too small to account for the increased flow.

In a more physiologic model, the surface-active copolymer increased coronary blood flow by a similar amount in isolated rat hearts perfused with human red blood cells at a 30% hematocrit following ischemic damage.

In an in vivo model of stroke produced by ligature of the middle cerebral artery of rabbits, the surface-active copolymer increases blood flow to ischemic brain tissue. As much as a two-fold increase was measured by a hydrogen washout technique. In each of these models, there were controls for hemodilution and there was no measurable effect on viscosity at any shear rate measured.

It is believed that available data suggests that the surface-active copolymer acts as a lubricant to increase blood flow through damaged tissues. It blocks adhesion of hydrophobic surfaces to one another and thereby reduces friction and increases flow. This hypothesis is strengthened by the observation that the surface-active copolymer has little effect on blood flow in normal tissues where such frictional forces are small.[10]

The surface-active copolymers are not metabolized by the body and are quickly eliminated from the blood. The half-life of the copolymer in the blood is believed to be approximately two hours. It is to be understood that the surface-active copolymer in the improved fibrinolytic composition is not covalently bound to any of the other components in the composition nor is it covalently bound to any proteins.

The surface-active copolymer can be administered with a fibrinolytic enzyme, a free radical scavenger, or it can be administered alone for treatment of certain circulatory conditions which either are caused by or cause pathological hydrophobic interactions of blood components. These conditions include, but not limited to, myocardial infarction, stroke, bowel or other tissue infarctions, malignancies, adult respiratory distress syndrome (ARDS), disseminated intravascular coagulation (DIC), diabetes, unstable angina pectoris, hemolytic uremic syndrome, red cell fragmentation syndrome, heat stroke, retained fetus, eclampsia, malignant hypertension, burns, crush injuries, fractures, trauma producing shock, major surgery, sepsis, bacterial, parasitic, viral and rickettsial infections which promote activation of the coagulation system, central nervous system trauma, and during and immediately after any major surgery. It is believed that treatment of the pathological hydrophobic interactions in the blood that occurs in these conditions significantly reduces microvascular and other complications that are commonly observed.

The surface-active copolymer is also effective in increasing the collateral circulation to undamaged tissues with compromised blood supply. Such tissues are frequently adjacent to areas of vascular occlusion. The mechanism appears to be reducing pathological hydrophobic interactions in small blood vessels. Circulatory conditions where the surface-active copolymers are effective include, but are not limited to, cerebral thrombosis, cerebral embolus, myocardial infarction, unstable angina pectoris, transient cerebral ischemic attacks, intermittent claudication of the legs, plastic and reconstructive surgery, balloon angioplasty, peripheral vascular surgery, and orthopedic surgery, especially when using a tourniquet.

The surface-active copolymer has little effect on the viscosity of normal blood at shear rates ranging from 2.3 $sec^{-1}$ (low) to 90 $sec^{-1}$ (high). However, it markedly reduces the abnormally high viscosity found in postoperative patients and in those with certain pathologic conditions. This observation posed two questions: 1) what caused the elevated whole blood viscosity in these patients and, 2) by what mechanisms did the surface-active copolymer, which has only minor effects on the blood viscosity of healthy persons, normalize pathologic elevations in viscosity?

It is generally accepted that hematocrit and plasma fibrinogen levels are the major determinants of whole blood viscosity. This has been confirmed in normal individuals and in many patients with inflammatory conditions. However, these factors could not explain the changes that were observed. In patients having coronary artery cardiac bypass surgery, it was found that hematocrit fell an average of 23±4% and fibrinogen fell 48±9% within six hours after surgery. The viscosity did not decrease as expected, but increased from a mean of 23±2 to 38±4 centipoise (at a shear rate of 2.3 $sec^{-1}$). Viscosities in excess of 100 were found in some patients. The abnormally high viscosity of blood was associated with circulating high molecular weight polymers of soluble fibrin.[11] The soluble fibrin levels rose from 19±5 µg/ml to 43±6 µg/ml during surgery. These studies utilized a calorimetric enzymatic assay for soluble fibrin[12] and Western blotting procedures with SDS agarose gels to determine the molecular weight of the large protein polymers.[13]

In the absence of specific receptors, cells and molecules in the circulation adhere to one another if the adherence reduces the free energy or surface tension between them. An assessment of the surface tension of various components of the blood can be made by measuring contact angles.

Red blood cells, lymphocytes, platelets, neutrophils all have contact angles in the range of 14 to 17 degrees. Peripheral blood proteins, such as albumin, $\alpha_2$macroglobulin, and Hageman factor have contact angles in the slightly lower range of 12–15. This means that these proteins have no adhesive energy for the cells. In contrast, fibrinogen has a contact angle of 24 degrees and soluble fibrin of 31. Consequently, fibrinogen adheres weakly to red blood cells and other cells in the circulation promoting rouleaux formation. Fibrin promotes a very much stronger adhesion than fibrinogen because of its elevated contact angle and its tendency to form polymers with fibrinogen. Soluble fibrin in the circulation produces the increased adhesion which results in a very markedly increased viscosity at low shear rates. This adhesion also involves the endothelial walls of the blood vessels. If the adhesive forces are insufficient to slow movement of cells, they produce an increased friction. This is especially important in the very small blood vessels and capillaries whose diameters are equal to or less than that of the circulating cells. The friction of cells sliding through these small vessels is significant. The surface-active copolymer blocks the adhesion of fibrinogen and fibrin to hydrophobic surfaces of cells and endothelial cells. This prevents their adhesion and lubricates them so there is a greatly reduced resistance to flow. This can be measured only partially by measurements of viscosity.

Whether a certain fibrinogen level is sufficient to cause a problem in circulation is dependent upon several parameters of the individual patient. High hematocrits and high levels of fibrinogen are widely regarded as the primary contributors to increased viscosity. However, elevated fibrinogen levels are frequently associated with elevated soluble fibrin in the circulation. Careful studies have demonstrated that the fibrin is frequently responsible for the most severe changes. The normal level of fibrinogen is 200–400 μg/ml. It has been determined that, in most patients, fibrinogen levels of greater than approximately 800 μg/ml will cause the high blood viscosity at the low shear rates mentioned hereinabove. The normal level of soluble fibrin has been reported to be approximately 9.2±1.9.[14] Using the Wiman and Ranby assay, viscosity at low shear rates was unacceptably high above about 15 μg/ml. It must be understood that soluble fibrin means molecular species that have a molecular weight of from about 600,000 to several million.

Numerous methods have been used for demonstrating soluble fibrin. These include cryoprecipitation especially cryofibrinogen. Heparin has been used to augment the precipitate formation. Ethanol and protamine also precipitate fibrin from plasma. Modem techniques have demonstrated that the soluble fibrin in the circulation is generally complexed with solubilizing agents. These are most frequently fibrinogen or fibrin degradation products. Des AA fibrin in which only the fibrin of peptide A moieties have been cleaved, tends to form relatively small aggregates consisting of one molecule of fibrin with two of fibrinogen. If both the A and B peptides have been cleaved to produce des AABB fibrin, then much larger aggregates are produced in the circulation. Fibrin degradation products can polymerize with fibrin to produce varying size aggregates depending upon the particular product involved.

Soluble fibrin in the circulation can markedly increase blood viscosity, especially at low shear rates. However, the relevance of this for clinical situations remains unclear. Viscosity assesses primarily the aggregation of red blood cells which is only one of many factors which determine in vivo circulation. Other factors affected by soluble fibrin are the endothelial cells, white blood cells and platelets. Soluble fibrin is chemotactic for endothelial cells, adheres to them avidly and causes their disorganization. It also has stimulatory effects for white blood cells, especially macrophages. Some of the effects of soluble fibrin may be mediated by specific receptors on various types of cells. However, since the free energy, as measured by contact angles of soluble fibrin, is less than that of any other plasma protein, it adheres avidly by a nonspecific hydrophobic interactions to virtually all formed elements in the blood.

Circulating soluble fibrin is normally cleared by macrophages and fibrinolytic mechanisms without producing damage. However, if the production of soluble fibrin is too great or if the clearance mechanisms have been compromised or if complicating disease factors are present, then soluble fibrin can induce deleterious reactions.

Soluble fibrin is produced in damaged or inflamed tissues. Consequently, its effects are most pronounced in these tissues where it coats endothelial cells and circulating blood cells in a fashion which markedly reduces perfusion. The largest effects are in the small blood vessels where soluble fibrin coating the endothelial cells and white blood cells produces a severe increase in friction to the movement of white cells through the small vessels. Friction appears to be a much more severe problem with white blood cells and red blood cells because they are larger and much more rigid.

If production of soluble fibrin is sufficient, then effects are noticed in other areas. The best studied is the adult respiratory distress syndrome where soluble fibrin produced in areas of damaged tissue produces microthrombi and other processes in the lungs which can cause pulmonary failure. However, lesser degrees of vascular compromise can be demonstrated in many other organs.

Soluble fibrin, either alone or in complex with fibrinogen and other materials, is now recognized as being a major contributor to the pathogenesis of a diverse range of vascular diseases ranging from coronary thrombosis through trauma, burns, reperfusion injury following transplantation or any other condition where there has been localized or generalized activation of coagulation. A recent study demonstrated that virtually all patients with acute myocardial infarction or unstable angina pectoris have markedly elevated levels of soluble fibrin in their circulation.

An example of the effects of soluble fibrin has been shown in studies using dogs. A normal dog is subjected to a hysterectomy. Then, while the animal is still under anesthesia, the external jugular vein is carefully dissected. Alternatively, the vein may be occluded by gentle pressure with the fingers for seven minutes. It is examined by scanning electron microscopy for adhesion of fibrin, red blood cells and other formed elements.

One finds that very few cells adhere to the endothelia of veins from dogs which had not undergone hysterectomy, whether or not there had been stasis produced by seven minutes occlusion. Similarly, there was only a small increase in adhesion of red blood cells to the endothelium of the jugular vein in animals who had undergone hysterectomy. If, however, the animals had a hysterectomy in addition to mild seven minute occlusion of the veins, then there was a striking increase in adhesion of formed elements of blood to the endothelial surfaces in some cases producing frank mural thrombi. Both red blood cells and fibrin were visibly adherent to the endothelial surfaces. In addition, there was disruption of the normal endothelial architecture. All of the animals had elevated levels of soluble fibrin after the surgery. This model demonstrates the effects of soluble fibrin produced by relatively localized surgery to produce a greatly increased risk of deep vein thrombosis at a distant site.

The surface-active copolymer addresses the problems of fibrin and fibrinogen in the blood by inhibiting the adhesion of fibrin, fibrinogen, platelets, red blood cells and other detectable elements of the blood stream. It blocks the formation of a thrombus on a surface. The surface-active copolymer has no effect on the viscosity of water or plasma. However, it markedly increases the rate of flow of water and plasma in small segments through tubes. The presence of air interfaces at the end of the columns or air bubbles which provide a significant surface tension produce a friction along the walls of the tubes. The surface-active copolymer reduces this surface tension and the friction and improves flow. This is an example whereby the surface-active copolymer improves flow of fluid through tissues through a tube even though it has no effect on the viscosity of the fluid as usually measured.

The surface-active copolymer has only a small effect on the viscosity of whole blood from normal individuals. It has little effect on the increase that occurs with high hematocrit. However, it has an effect on the very large increase in viscosity at low shear rates thought to be caused by soluble fibrin and fibrinogen polymers.

Recent studies demonstrate that the surface-active copolymer also has the ability to protect myocardial and other cells from a variety of noxious insults. During prolonged ischemia, myocardial cells undergo "irreversible injury." Cells which sustain irreversible injury are morphologically intact but are unable to survive when returned to a normal environment. Within minutes of reperfusion with oxygenated blood, cells containing such occult lesions develop swelling and contraction bands and die.

Irreversibly injured myocardial cells have mechanical and osmotic fragility and latent activation of lipases, proteases and other enzymes. Reperfusion initiates a series of events including calcium loading, cell swelling, mechanical membrane rupture and the formation of oxygen free radicals which rapidly destroy the cell. The surface-active copolymer retards such injury in the isolated perfused rat heart model. The mechanisms probably include osmotic stabilization and increased mechanical resistance in a fashion similar to that known for red blood cells.

The protective effects of the surface-active copolymer on the myocardium are not limited to the myocardial cells. It also protects the endothelial cells of the microvasculature as assessed morphologically. By maintaining the integrity of such cells and helping to restore and maintain non-adhesive surfaces, the surface-active copolymer tends to reduce the adhesion of macromolecules and cells in the microvasculature, to reduce coronary vascular resistance and to retard development of the no reflow phenomenon.

Examples of conditions where the surface-active copolymer can be used is in the treatment of sickle cell disease and preservation of organs for transplantation. In both of these embodiments, blood flow is reduced because of pathologic hydrophobic interactions.

During a sickle cell crisis, sickled red blood cells aggregate because of the abnormal shape of the cells. In many cases, there are high concentrations of soluble fibrin due to disseminated intravascular coagulation. This results in pathological hydrophobic interactions between blood cells, cells lining the blood vessels and soluble fibrin and fibrinogen. By administering to the patient the surface-active copolymer, blood flow is increased and tissue damage is thereby reduced. The surface-active copolymer may be given prior to a sickle cell crisis to prevent onset of the crisis. In addition, the solution with the effective amount of surface-active copolymer may also contain an effective amount of anticoagulant.

In organs that have been removed from a donor for transplantation, the tissue is damaged due to ischemia and lack of blood. Preferably, the surface-active copolymer is mixed with a perfusion medium. The perfusion media that can be used with the surface-active copolymer are well known to those of ordinary skill in the art. The perfusion media can also be whole blood or plasma. The solution can be perfused through the organ thereby reducing the damage to the tissue. Because the tissue damage is reduced by perfusing the organ with the surface-active copolymer solution, the time the organ is viable and therefore the time the organ can be transplanted is increased.

Because the surface-active copolymer improves flow of blood through diseased or damaged tissue with minimal effect on blood flow in normal tissue, it is contemplated that the surface-active copolymer includes a method for delivering drugs to damaged tissue comprising the step of administering to the animal or human a solution containing an effective amount of a drug, and an effective amount of the surface-active copolymer.

Any drug that has an activity in diseased or damaged tissue is suitable for use with the surface-active copolymer. These drugs include:
 1. antimicrobial drugs
    antibiotics
    antifungal drugs
    antiviral drugs
    antiparasitic drugs;
 2. antifungal drugs;
 3. chemotherapeutic drugs for treating cancers and certain infections;
 4. free radical scavenger drugs, including those drugs that prevent the production of free radicals;
 5. fibrinolytic drugs;
 6. perfusion media;
 7. anti-inflammnatories, including, but not limited to, both steroids and nonsteroid antiinflammatory drugs;
 8. membrane stabilizers, such as dilantin;
 9. anticoagulants;
 10. ionotropic drugs, such as calcium channel blockers;
 11. autonomic nervous system modulators.

Polyoxypropylene/polyoxyethylene Copolymers as Adjuvants

Other polyoxypropylene/polyoxyethylene copolymers are also useful as an adjuvant and a vaccine which is comprised of an antigen and an improved adjuvant. In one embodiment, the antigen is admixed with an effective amount of a surface-active copolymer having the following general formula:

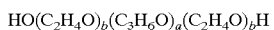

wherein the molecular weight of the hydrophobe ($C_3H_6O$) is between approximately 4500 to 5500 daltons and the percentage of hydrophile ($C_2H_4$)) is between approximately 5% and 15% by weight.

The improved vaccine also comprises an antigen and an adjuvant wherein the adjuvant comprises a surface-active copolymer with the following general formula:

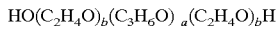

wherein the molecular weight of the hydrophobe ($C_3H_6O$) is between approximately 3000 to 5500 daltons and the percentage of hydrophile (C2H$_4$O) is between approximately 5% and 15% by weight which is formulated as a water-in-oil emulsion. The copolymers destabilize commonly used water-in-oil vaccine emulsions, but surprisingly increase their efficacy and increase stability if the usual emulsifying agents are omitted.

The improved vaccine also comprises an antigen and an adjuvant wherein the adjuvant comprises a surface-active copolymer with the following general formula:

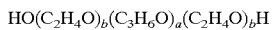

wherein the molecular weight of the hydrophobe ($C_3H_6O$) is between approximately 3000 to 5500 daltons and the percentage of hydrophile ($C_2H_4O$) is between approximately 5% and 15% by weight, and a lipopolysaccharide (LPS) derivative. The adjuvant comprising a combination of LPS and surface-active copolymer produces a synergy of effects in terms of peak titer, time to reach peak titer and length of time of response. In addition, the combination tends to increase the protective IgG2 isotypes.

The adjuvants also comprise an octablock copolymer (poloxamine) with the following general formula:

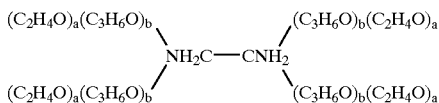

wherein:
the molecular weight of the hydrophobe portion of the octablock copolymer consisting of $(C_3H_6O)$ is between approximately 5000 and 7000 daltons;
a is a number such that the hydrophile portion represented by $(C_2H_4O)$ constitutes between approximately 10% and 40% of the total molecular weight of the compound;
b is a number such that the $(C_3H_6O)$ portion of the octablock copolymer constitute between approximately 60% and 90% of the compound and a lipopolysaccharide derivative.

The $(C_3H_6O)$ portion of the copolymer can constitute up to 95% of the compound. The $(C_2H_4O)$ portion of the copolymer can constitute as low as 5% of the compound.

The combination of lipid conjugated polysaccharide with copolymer and an immunomodulating agent such as monophosphoryl lipid A, induces the production of a strong IgG response in which all of the subclasses of IgG are present. In particular, the IgG2 and IgG3 subclasses which are protective against pneumococcal infections are predominant. This is an unexpected finding because there is no protein or peptide in the immnunogen preparation. It is believed that peptide moieties are essential for stimulating T cells which are required for production of these isotypes. Others have reported that polysaccharides are incapable of stimulating T cells. Nevertheless, the combination of copolymer, lipid conjugated polysaccharide and immunomodulating agent is able to produce such a response. The adjuvant activity of the poloxamers and the poloxamines is described in detail in copending U.S. patent application Ser. No. 07/544,831, which is incorporated herein by reference.

Polyoxypropylene/polyoxyethylene Copolymers as Antiinfective Agents

Another group of polyoxypropylene/polyoxyethylene copolymers inhibit the growth of bacteria and viruses. For example, these surface-active copolymers have been shown to inhibit HIV viruses, *Mycobacteria species* and *Toxoplasma gondii*.

The surface-active copolymers are effective in treating a viral infection in a human or animal including infections caused by the HIV virus or related strains. The present invention provides a composition that can be administered to patients who are infected with HIV viruses or similar viruses. The surface-active copolymer is effective in inhibiting or suppressing the replication of the HIV virus and related virus strains in cells.

The surface-active copolymers are useful for treating infections caused by microorganisms when used alone or with a conventional antibiotic. Several conventional antibiotics that can be used with the surface-active copolymer include, but are not limited to, rifampin, isoniazid, ethambutol, gentamicin, tetracycline, and erythromycin.

The surface-active copolymer has the following general formula:

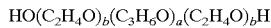

wherein a is an integer such that the hydrophobe represented by $(C_3H_6O)$ has a molecular weight of about 1200 to 5300 daltons, preferably about 1750 to 4500 daltons, and b is an integer such that the hydrophile portion represented by $(C_2H_4O)$ constitutes approximately 10% to 50% by weight of the compound.

The antiinfective activity of the poloxamers is described in detail in copending U.S. patent application Ser. No. 07/760,808, which is incorporated herein by reference.

Polyoxypropylene/polyoxyethylene Copolymers as Growth Stimulators and Immune Stimulators Certain of the polyoxypropylene/polyoxyethylene copolymers are capable of effecting biological systems in several different ways. The biologically-active copolymers are capable of stimulating the growth of an organism, stimulating the motor activity of an organism, stimulating the production of T-cells in the thymus, peripheral lymphoid tissue, and bone marrow cells of an animal, and stimulating immune responsiveness of poultry.

The biologically-active copolymers also have a wide variety of effects on individual cells. These compounds have ionophoric activity, i.e., they cause certain ions to be transported across cell membranes. The compounds can cause non-cytolytic mast cell degranulation with subsequent histamine release. In addition, it has been found that certain members of this class of biologically-active copolymers are capable of specifically killing certain cancer cell lines.

Certain„of the biologically-active copolymers can be administered orally to animals to stimulate the growth of food animals such as chickens and swine. These and other biological activities are discussed in detail in copending U.S. patent application Ser. Nos. 07/107,358 and 07/610,417, which are incorporated herein by reference.

Polyoxypropylene/polyoxyethylene Copolymer Structure

The surface-active copolymer blocks are formed by condensation of ethylene oxide and propylene oxide at elevated temperature and pressure in the presence of a basic catalyst. However, there is statistical variation in the number of monomer units which combine to form a polymer chain in each copolymer. The molecular weights giver are approximations of the average weight of copolymer molecule in each preparation. A more detailed discussion of the preparation of these compounds is found in U.S. Pat. No. 2,674,619, which is incorporated herein by reference. A more general discussion of the structure of poloxamers and poloxamine block copolymers can be found in Schmolka, I. R., "A Review of Block Polymer Surfactants", J. AM. OIL CHEMISTS' SOC., 54:110–116 (1977), which is incorporated herein by reference.

It has been determined that the commercially available preparations of polyoxypropylene/polyoxyethylene copolymers vary widely relative to the size and configuration of the constituent molecules. For example, the preparation of poloxamer 188 that is purchased from BASF (Parsippany, N.J.) has a published structure of a molecular weight of the hydrophobe $(C_3H_6O)$ of approximately 1750 daltons and the total molecular weight of the compound of approximately 8400 daltons. In reality, the compound is composed of molecules which range from a molecular weight of less than 3,000 daltons to over 20,000 daltons. The molecular diversity and distribution of molecules of commercial poloxamer 188 is illustrated by broad primary and secondary peaks detected using gel permeation chromatography.

In addition to the wide variation in polymer size in the poloxamer preparations currently available, it has been further determined that these fractions contain significant amounts of unsaturation. It is believed that this unsaturation in the polymer molecule is responsible, at least in part, for the toxicity and variable biological activities of the available poloxamer preparations.

Thus, the wide diversity of molecules which are present in the commercially available polyoxypropylene/polyoxyethylene copolymers make prediction of the biological activity difficult. In addition, as is shown in the poloxamer 188 preparations, the presence of other molecular species in the preparation can lead to unwanted biological activities.

The surface-active copolymer poloxamer 188 has been used as an emulsifier for an artificial blood preparation containing perfluorocarbons. It has been reported that patients receiving the artificial blood preparations have exhibited toxic reactions. The toxic reactions included activation of complement[15], paralysis of phagocyte migration[16], and cytotoxicity to human and animal cells in tissue culture[17]. Efforts using supercritical fluid fractionation to reduce the toxicity of the copolymers proved only partially successful.[18] In addition, in toxicological studies in beagle dogs, infusion of poloxamer 188 was shown to result in elevated liver enzymes, (SGOT) and increased organ weights (kidney). Histologic evaluation of the kidney demonstrated a dose related cytoplasmic vacuolation of the proximal tubular epithelial cells.

The enormous variation that can occur in biological activity when only small changes are made in chain length in the poloxamer copolymers is illustrated in Hunter, et al.[19] The authors show that a difference of 10% in the chain length of the polyoxyethylene portions of the poloxamer polymer can mean the difference between an excellent adjuvant and no adjuvant activity at all. Poloxamer 121 has a molecular weight of approximately 4400 daltons and contains approximately 10% by weight of polyoxyethelene. Poloxamer 122 has a molecular weight of approximately 5000 daltons and contains approximately 20% by weight of polyoxyethelene. The amount of polyoxypropylene in each molecule is approximately the same. As shown in Hunter, et al., when poloxamer 121 was used as an adjuvant with bovine serum albumin, the antibody titers were 67,814±5916. When poloxamer 122 was used as an adjuvant with bovine serum albumin under the same conditions, the antibody titer against BSA was 184±45. The control titer without any adjuvant was <100. Thus, a relatively small change in the chain length of the poloxamer can result in enormous changes in biological activity.

Because the commercially available sources of the polyoxypropylene/polyoxyethylene copolymers have been reported to exhibit toxicity as well as variation in biological activity, what is needed is a preparation of polyoxypropylene/polyoxyethylene copolymers which retain the therapeutic activities of the commercial preparations but are free from their other biological activities such as toxicity. In addition, what is needed is a preparation of polyoxypropylene/polyoxyethylene copolymers which is less polydisperse in molecular weight and contains less unsaturation and therefore is more efficacious.

SUMMARY OF THE INVENTION

The present invention comprises novel preparations of polyoxypropylene/polyoxyethylene copolymers which retain the therapeutic activity of the commercial preparations, but are free from the undesirable effects which are inherent in the prior art preparations. Because the polyoxypropylene/polyoxyethylene copolymers which comprise the present invention are a less polydisperse population of molecules than the prior art polyoxypropylene/polyoxyethylene copolymers, the biological activity of the copolymers is better defined and more predictable. In addition, the polyoxypropylene/polyoxyethylene copolymers which comprise the present invention are substantially free of unsaturation.

The present invention also comprises a polyoxypropylene/polyoxyethylene copolymer which has the following formula:

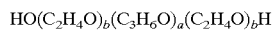

wherein the molecular weight of the hydrophobe ($C_3H_6O$) is approximately 1750 daltons and the total molecular weight of the compound is approximately 8400 daltons. The compound has a polydispersity value of less than approximately 1.05.

It has been determined that the toxicity exhibited by the commercially available surface-active copolymer poloxamer 188 is primarily due to the small amounts of high and low molecular weight molecules that are present as a result of the manufacturing process. The high molecular weight molecules (those greater than 15,000 daltons) are probably responsible for activation of the complement system. The low molecular weight molecules (those lower than 5,000 daltons) have detergent-like physical properties which can be toxic to cells in culture. In addition, the low molecular weight molecules have unsaturated polymers present in the population.

The optimal rheologic molecules of poloxamer 188 are approximately 8,400 to 9400 daltons. It has also been determined that poloxamer 188 molecules above 15,000 and below 5,000 daltons are less effective rheologic agents and exhibit unwanted side effects. A preparation containing molecules between 5,000 and t5,000 daltons is a more efficient rheologic agent.

The present invention also includes a method of preparing polyoxypropylene/polyoxyethylene block copolymers with polydispersity values of less than 1.05. The method of preparing a non-toxic surface-active copolymer includes first condensing propylene oxide with a base compound containing a plurality of reactive hydrogen atoms to produce polyoxypropylene polymer and then condensing ethylene oxide with the polyoxypropylene polymer to produce a polyoxypropylene/polyoxyethylene block copolymer with the following general formula:

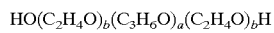

wherein the polydispersity value of the copolymer is less than 1.05, the improvement being the purification of the polyoxypropylene polymer to remove any truncated polymers before condensation with the ethylene oxide. The purification of the polyoxypropylene polymer can be by gel permeation chromatography.

Accordingly, it is an object of the present invention to provide a surface-active copolymer with a higher proportion of therapeutically active molecules while also eliminating molecules responsible for toxic effects.

It is another object of the present invention to provide a more homogeneous polyoxypropylene/polyoxyethylene copolymer relative to the molecular weight range.

It is another object of the present invention to provide a preparation of polyoxyethylene/polyoxypropylene block copolymer with a polydispersity value of less than 1.05.

It is another object of the present invention to provide a preparation of polyoxyethylene/polyoxypropylene block copolymer with substantially no unsaturation.

It is another object of the present invention to provide a surface-active copolymer with the therapeutic activity of poloxamer 188 that will not activate complement.

It is yet another object of the present invention to provide a purified poloxamer 188 that can be used safely in both humans and animals in treating tissue that has been damaged by ischemia.

It is yet another object of the present invention to provide a surface-active copolymer that can be used safely in both humans and animals in treating tissue that has been damaged by reperfusion injury.

It is yet another object of the present invention to provide a surface-active copolymer that can be used safely in both humans and animals as a vaccine adjuvant.

It is another object of the present invention to provide a surface-active copolymer with the therapeutic activity of poloxamer 188 that is not cytotoxic.

It is yet another object of the present invention to provide a surface-active copolymer that can be used safely in both humans and animals in treating stroke.

It is yet another object of the present invention to provide a surface-active copolymer which has less renal toxicity and less detergent-like activity.

It is yet another object of the present invention to provide a surface-active copolymer that can be used safely in both humans and animals as an antimicrobial agent.

It is yet another object of the present invention to provide a surface-active copolymer that can be used safely in both humans and animals as an antibacterial, an antiviral, an antifungal and an antiprotozoa agent.

It is yet another object of the present invention to provide a surface-active copolymer that can be used safely in both humans and animals in treating myocardial damage.

It is yet another object of the present invention to provide a surface-active copolymer that can be used safely in both humans and animals in treating adult respiratory distress syndrome.

These and other objects, features and advantages of the present invention will become apparent after a review of the following detailed description of the disclosed embodiments and the appended claims.

BRIEF DESCRIPTION OF THE FIGURES

FIG. 8 is a chromatogram of fraction 6 of the poloxamer 188 collected from the chromatographic run described in Example I.

FIGS. 9A through 9C are gel permeation chromatograms of unfractionated and fractionated poloxamer 760.5.

FIGS. 10A through 10C are nuclear magnetic spectra of the fractions represented in FIGS. 9A through 9C.

FIGS. 11A through 11C are gel permeation chromatograms of three fractions of poloxamer 188.

DETAILED DESCRIPTION

Although the prior art preparations of polyoxypropylene/polyoxyethylene block copolymers may have been suitable for industrial uses, it has been determined that the newly discovered uses for the copolymers as therapeutic agents require less polydisperse populations of molecules in the preparations.

The present invention comprises polyoxypropylene/polyoxyethylene copolymers that have a polydisperse value of less than 1.05. The novel copolymers can be prepared by removing disparate molecules from the prior art preparation or by preparing the copolymer according to the method that is contemplated as part of the present invention. The method of preparation of the copolymers of the present invention is the purification of the polyoxypropylene block of the polyoxypropylene/polyoxyethylene copolymer before the polyoxyethylene blocks are added to the molecule. In this way, the partially polymerized polyoxypropylene polymers are removed before the addition of polyoxyethylene polymers to the molecule. This results in a block copolymer that is within the physical parameters which are contemplated as the present invention.

The present invention also comprises a polyoxypropylene/polyoxyethylene block copolymer which has the following formula:

wherein the molecular weight represented by the polyoxypropylene portion of the copolymer is between approximately 900 and 15000 daltons with a more preferred molecular weight of between 1,200 and 6500 daltons and the molecular weight represented by the polyoxyethylene portion of the copolymer constitutes between approximately 5% and 95% of the copolymer with a more preferred range of between approximately 10% and 90% of the copolymer and the polydispersity value is less than approximately 1.07.

The present invention also comprises a polyoxypropylene/polyoxyethylene block copolymer which has the following formula:

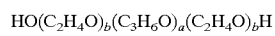

wherein the molecular weight of the hydrophobe ($C_3H_6O$) is approximately 1750 daltons and the average molecular weight of the compound is approximately 8300 to 9400 daltons. The compound has a molecular weight distribution ranging from approximately 5,000 to 15,000 daltons with a preferred molecular weight range of between approximately 7,000 to 12,000 daltons. In addition, the copolymer has substantially no unsaturation as measured by nuclear magnetic resonance.

Figure 1:
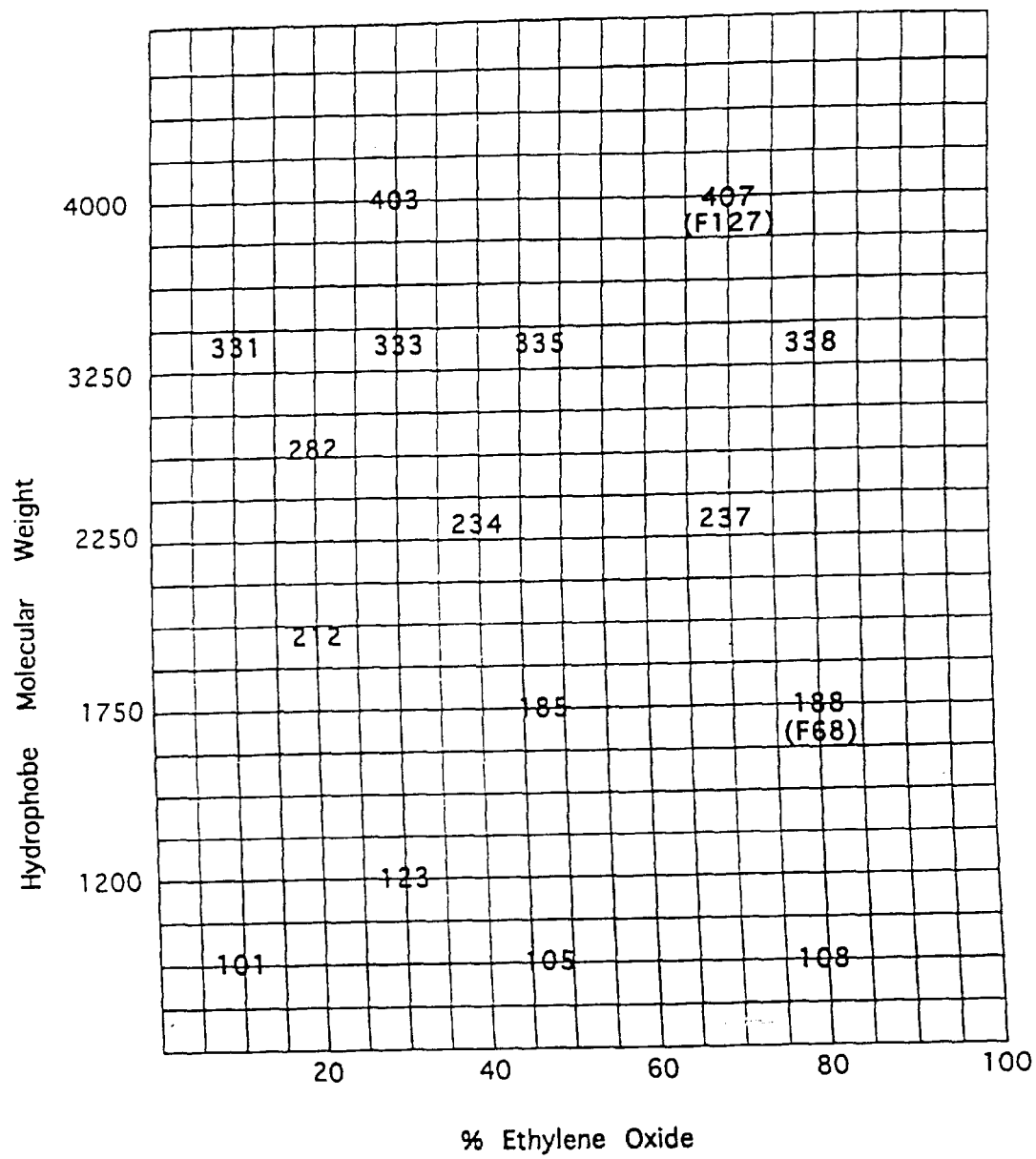
FIG. 1 is a poloxamer grid for naming poloxmer compounds.

The nomenclature of the poloxamer compounds is based on a poloxamer grid (FIG. 1). The poloxamer grid is the relationship between nomenclature and composition of the various polymer members. The hydrophobe (polyoxypropylene) molecular weights are given as approximate midpoints of ranges. The first two digits of a poloxamer number on the grid, multiplied by 100, gives the approximate molecular weight of the hydrophobe. The last digit, times 10, gives the approximate weight percent of the hydrophile (polyoxyethylene) content of the surfactant. For example, poloxamer 407, shown in the upper right hand quadrant of the grid (FIG. 1), is derived from a 4000 molecular weight hydrophobe with the hydrophile comprising 70% of the total molecular weight of the copolymer. Another example is poloxmer 760.5 which has a hydrophobe with a molecular weight of 7600 daltons and has a hydrophile which comprises 5% of the total molecular weight of the copolymer.

The representative poloxamers that are described in this patent application along with their Pluronic® numbers are shown in Table I.

TABLE I

| Poloxamer No. | Pluronic® No. | % POE |
|---|---|---|
| 188 | F68 | 80% |
| 331 | L101 | 10% |
| 760.5 | L180.5 | 5% |
| 1000.5 | L331 | 5% |

Although molecular weight averages are important and useful when characterizing polymers in general, it is important to know the molecular weight distribution of a polymer. Some processing and end-use characteristics (melt flow, flex life, tensile strength, etc.) are often predicted or understood by observing the values and/or changes occurring in specific molecular weight averages. These values can also be assigned to biological properties of the polyoxypropylene/polyoxyethylene copolymers. A list of the processing characteristics follows.

| Molecular Weight Averages | Processing Characteristics |
|---|---|
| Mz | Flex life/stiffness |
| Mn | Brittleness, flow |
| Mw | Tensile strength |

For example, the breadth of the distribution is known as the polydispersity (D) and is usually defined as Mw/Mn. A monodisperse sample is defined as one in which all molecules are identical. In such a case, the polydispersity (Mw/Mn) is 1.0. Narrow molecular weight standards have a value of D near 1 and a typical polymer has a range of 2 to 5. Some polymers have a polydispersity in excess of 20.

The equations for expressing polydispersity are as follows:

$$\overline{M}_n = \frac{\sum \text{Area}_i}{\sum \text{Area}_i / M_i}$$

$$\overline{M}_w = \frac{\sum [(\text{Area}_i)(M_i)]}{\sum (\text{Area}_i)}$$

$$\overline{M}_z = \frac{\sum [(\text{Area}_i)(M_i)^2]}{\sum [(\text{Area}_i)(M_i)]}$$

$$\overline{M}_{z+1} = \frac{\sum [(\text{Area}_i)(M_i)^3]}{\sum [(\text{Area}_i)(M_i)^2]}$$

$$\text{Polydispersity}(D) = \frac{\overline{M}_w}{\overline{M}_n}$$

where:
Area$_i$=area of the ith slice
M$_i$=molecular weight of the ith slice

Thus, by calculating the parameters listed above, one can specify a certain polydispersity that is acceptable for a pharmaceutical preparation. A high polydispersity value indicates a wide variation in size for the population of molecules in a given preparation while a lower polydispersity value indicates less variation. Because molecular size is an important determinant of biological activity, it is important to restrict the dispersity of the molecules in the preparation in order to achieve a more homogeneous biological effect. Thus, the polydispersity measurement can be used to measure the dispersity of molecules in a preparation and correlates to that compound's potential for variation in biological activity.

It is to be understood that the polydispersity values that are described herein were determined from chromatograms which were obtained using a Model 600E Powerline chromatographic system equipped with a column heater module, a Model 410 refractive index detector, Maxima 820 software package (all from Waters, Div. of Millipore, Milford, Mass.), two LiChrogel PS-40 columns and a LiChrogel PS-20 column in series (EM Science, Gibbstown, N.J.), and polyethylene glycol molecular weight standards (Polymer Laboratories, Inc., Amherst, Mass.). Polydispersity values obtained using this system are relative to the chromatographic conditions, the molecular weight standards and the size exclusion characteristics of the gel permeation columns. Polydispersity measurements using different separation principles may give absolute polydispersity values which are different from those described herein. However, one of ordinary skill in the art can easily convert any polydispersity value that is obtained using a different separation method to the values described herein simply by running a single sample on both systems and then comparing the polydispersity values from each chromatogram.

In accordance with the present invention, a composition is provided that is a polyoxypropylene/polyoxyethylene block copolymer that has a polydispersity value of less than 1.07. Preferably, the polydispersity value is less than approximately 1.05, with a most preferable polydispersity value of 1.03. It is to be understood that the present invention includes, but is not limited to, poloxamer compounds and poloxamine compounds.

Also in accordance with the present invention, a composition is provided that is a surface-active copolymer comprising a polyoxypropylene/polyoxyethylene block copolymer with the following general formula:

wherein the total molecular weight of the copolymer is between approximately 5,000 and 15,000 daltons, preferably a molecular weight of between approximately 7,000 and 12,000 daltons and the molecular weight represented by the polyoxyethylene portion of the copolymer constitutes approximately 80% of the copolymer.

One embodiment of the present invention comprises a polyoxypropylene/polyoxyethylene copolymer which has the following formula:

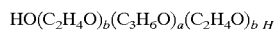

wherein the molecular weight of the hydrophobe (C$_3$H$_6$O) is approximately 1750 daltons and the average molecular weight of the compound is approximately 8300 to 9400 daltons. The polydispersity value is less than approximately 1.05. A block copolymer corresponding to at least these physical parameters has the beneficial biological effects of the prior art poloxamer 188 but does not exhibit the unwanted side effects which have been reported for the prior art compound. By reducing the polydispersity value of the surface-active copolymer, it has been found that the toxicity associated with the prior art poloxamer 188 is significantly reduced. However, the beneficial therapeutic activity of the modified poloxamer 188 is retained.

The surface-active copolymers of the present invention can be prepared in a number of ways. The polydispersity value can be reduced by subjecting the prior art compounds to gel permeation chromatography. In addition, the compounds can be subjected to molecular sieving techniques that are known to those of ordinary skill in the art.

The surface-active copolymer of the present invention can be prepared in several ways. In the first method, commercially available poloxamer 188 is subjected to gel permeation chromatography. The chromatogram that is obtained from this procedure is shown in FIG. 1.

As can be seen in FIG. 1, commercial poloxamer 188 is composed of a broad distribution of molecules with a peak molecular weight of approximately 7900 to 9500 daltons. This corresponds generally to the published molecular weight for poloxamer 188 of 8400 daltons. The published molecular weight for poloxamer 188 is determined by the hydroxyl method. The end groups of polyether chains are hydroxyl groups. The number averaged molecular weight can be calculated from the analytically determined "OH Number" expressed in mg KOH/g sample. It should be understood that the molecular weight of a polydisperse compound can be different depending upon the methodology used to determine the molecular weight.

FIG. 1 also shows small secondary peaks or shoulders lying to the left and right of the primary peak. These areas of the poloxamer 188 chromatogram represent the high and low molecular weight molecules respectively. The high molecular weight species range in size from approximately 24,000 to 15,000 daltons. It is believed that these larger molecules have a greater capacity to activate complement compared to the lower molecular weight species. The shoulder on the right or lower molecular weight side of the chromatogram is composed of molecules between approximately 2,300 daltons and 5,000 daltons. This species represents compounds which have more detergent-like properties and are cytotoxic to cells.

Using the gel permeation chromatography procedure, it has been determined that a fraction of poloxamer 188 with molecules ranging from approximately 5,000 daltons to 15,000 daltons, preferably between approximately 6,000 daltons and 13,000 daltons, with a peak at approximately 8,700 daltons, represents a population of surface-active copolymers which are essentially devoid of toxic activities while still retaining the beneficial therapeutic activity of the commercially available poloxamer 188. This new composition is a much more homogeneous preparation than those currently available and unexpectedly has fewer side effects than the prior art preparation.

It should be understood that the molecular weight range that is described as the optimum range for the copolymer is to be considered the outside range and that any population of molecules that fall within that range are considered as embodiments of the present invention.

The present invention also includes a novel method of preparing a surface-active copolymer composition with the specifications described herein. The novel method involves the preparation of a uniform hydrophobic polyoxypropylene polymer and then proceed with the addition of the hydrophilic polyoxyethylene as is normally done. It is believed that the toxic copolymers that are the result of the standard commercial method of preparing poloxamer 188 are due to truncated polymer chains and to unsaturation in the polymer.

In practicing the present invention, the hydrophobic polyoxypropylene polymer is purified to obtain a substantially uniform population of polyoxypropylene polymers. The purification can be performed using gel permeation chromatography. However, any method known to one of ordinary skill in the art which gives the desired range of polyoxypropylene polymers can be used.

In preparing the improved rheologic reagent, the polyoxypropylene polymer should have an average molecular weight of approximately 1750 daltons with an approximate molecular weight range between 1,000 and 2,600 daltons. The preferred molecular weight range is between 1,200 and 2,400 daltons.

After the desired polyoxypropylene copolymer has been obtained, the ethylene portion of the copolymer is added to both ends of the molecule by standard methods well known to those of ordinary skill in the art. The final polymer population should have a polyoxyethylene composition of approximately 20% of the total molecular weight of the molecule.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLE I

Poloxamer 188 (BASF Corporation, Parsippany N.J.) is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the commercially prepared poloxamer 188 copolymer. The chromatographic system is equipped with two LiChrogel PS-40 columns and a LiChrogel PS-20 column in series (EM Science, Gibbstown, N.J.). The LiChrogel PS-40 columns are 10 μm particle size and the LiChrogel PS-20 column is 5 μm particle size. All columns are 7 mm by 25 cm in size.

Figure 2:
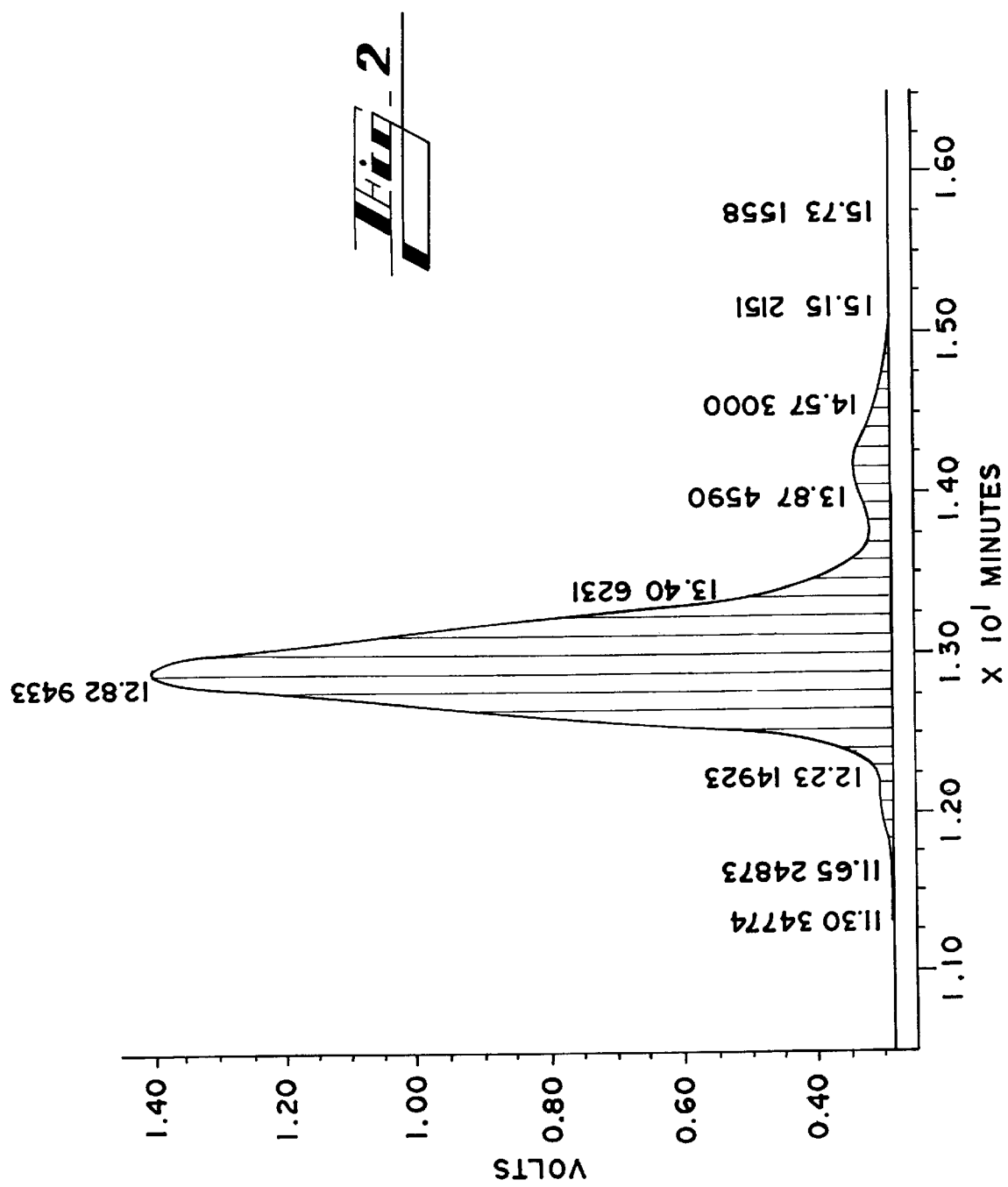
FIG. 2 is a chromatogram of commercially available poloxamer 188 subjected to gel permeation chromatography.
Figure 3:
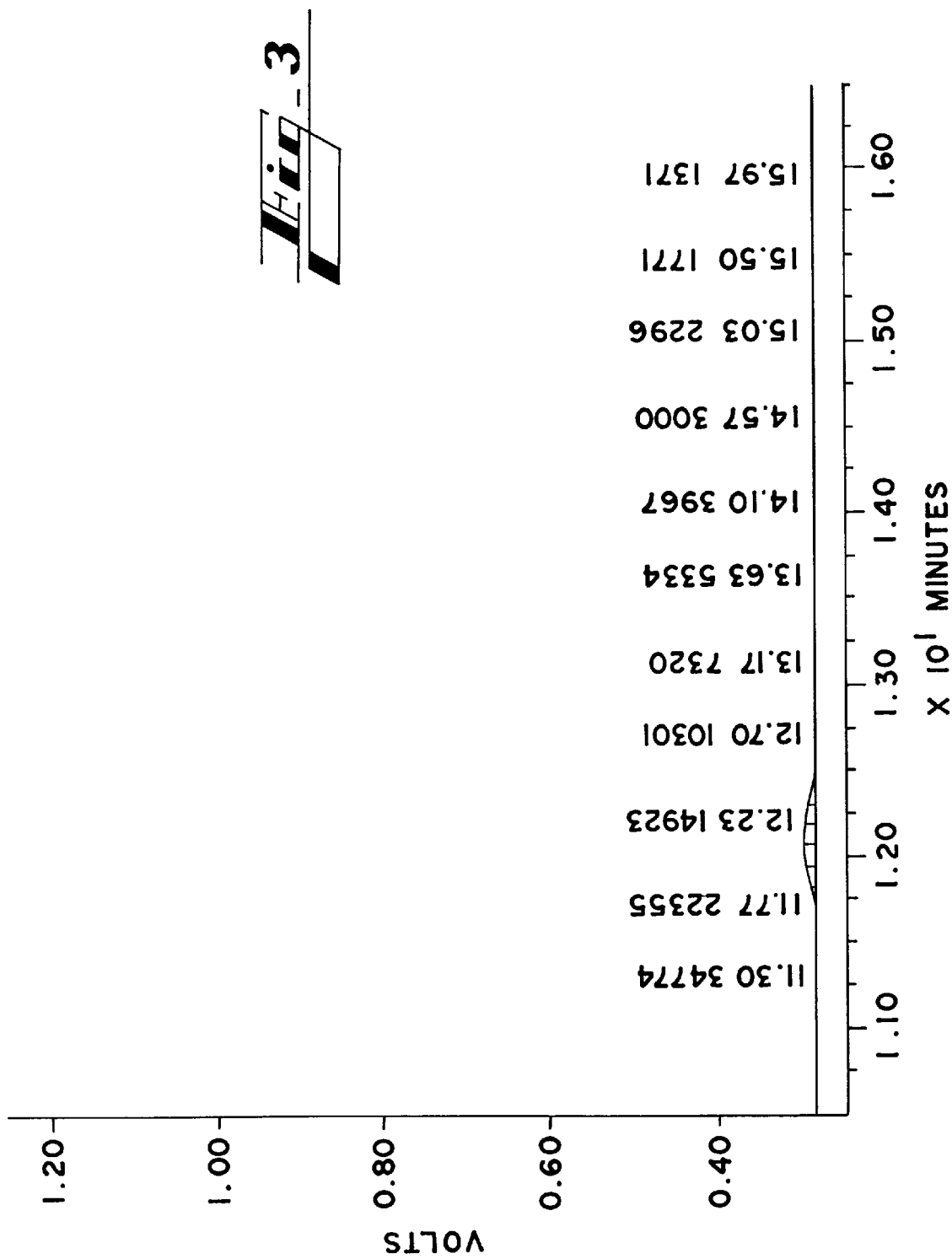
FIG. 3 is a chromatogram of fraction 1 of the poloxamer 188 collected from the chromatographic run described in Example I.
Figure 4:
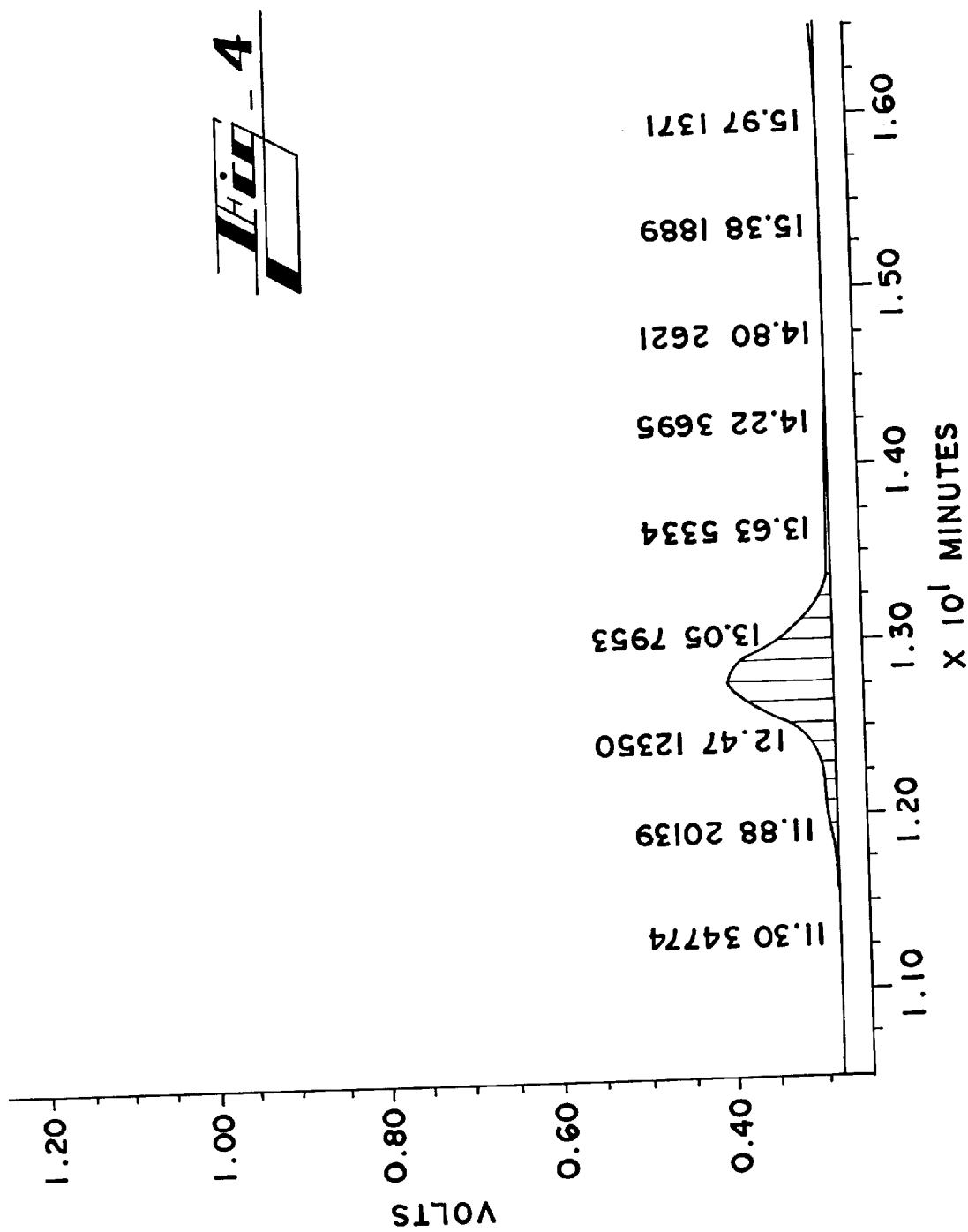
FIG. 4 is a chromatogram of fraction 2 of the poloxamer 188 collected from the chromatographic run described in Example I.

200μL (4mg) of the poloxamer 188 in tetrahydrofuran is added to the column and the sample is run with the columns and the detector at 40° C. The resulting chromatogram is shown in FIG. 2.

EXAMPLE II

Figure 5:
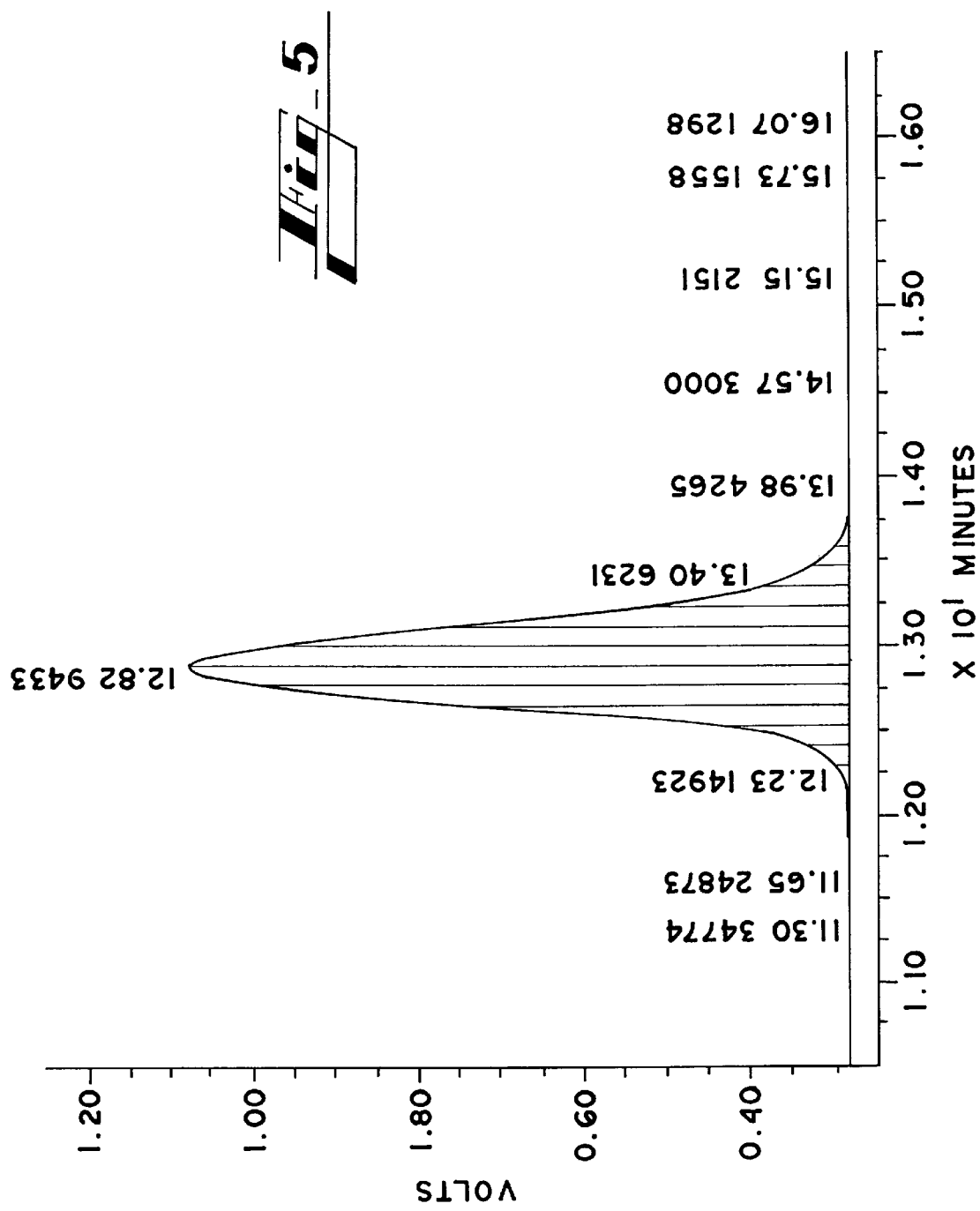
FIG. 5 is a chromatogram of fraction 3 of the poloxamer 188 collected from the chromatographic run described in Example I.
Figure 6:
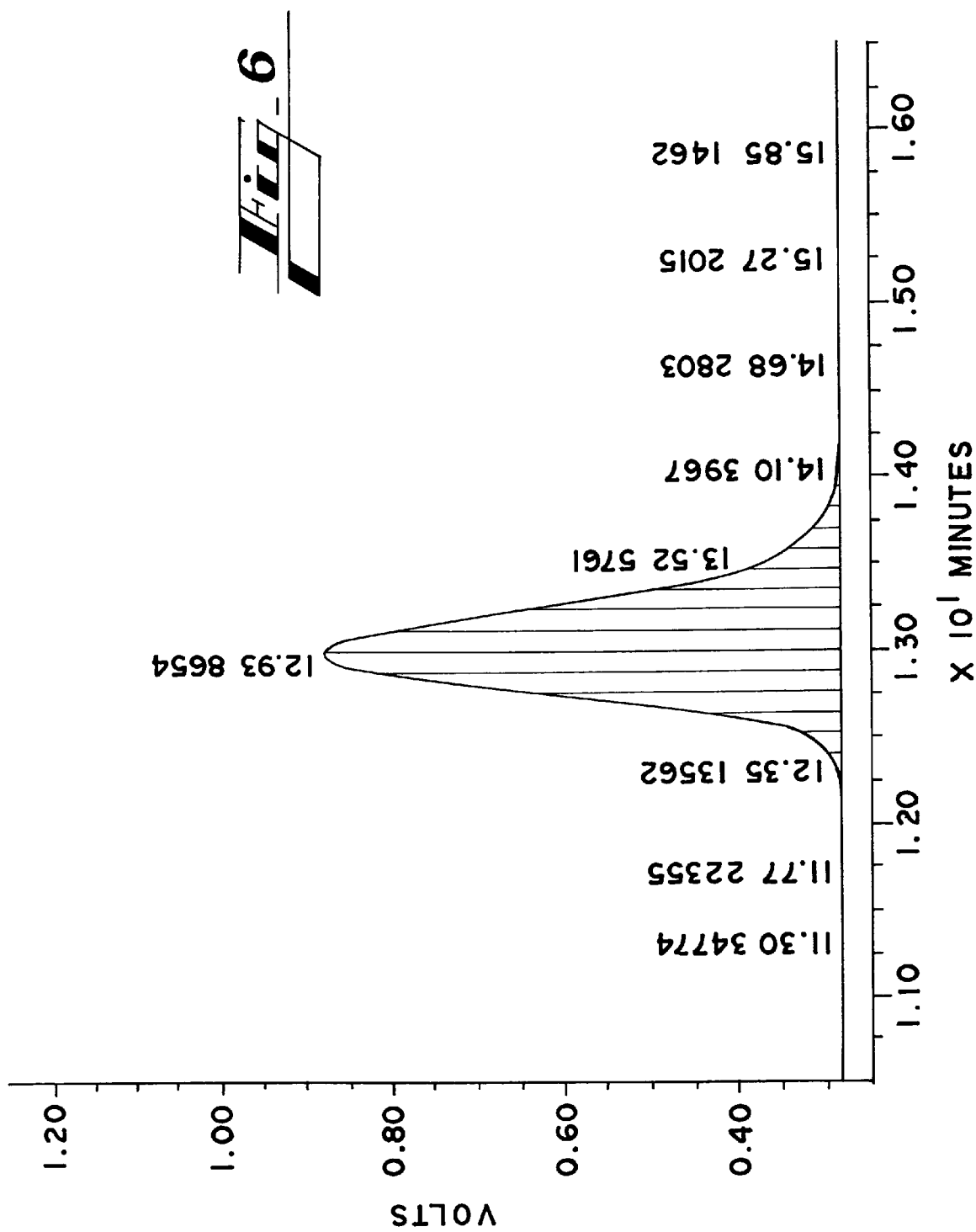
FIG. 6 is a chromatogram of fraction 4 of the poloxamer 188 collected from the chromatographic run described in Example I.
Figure 7:
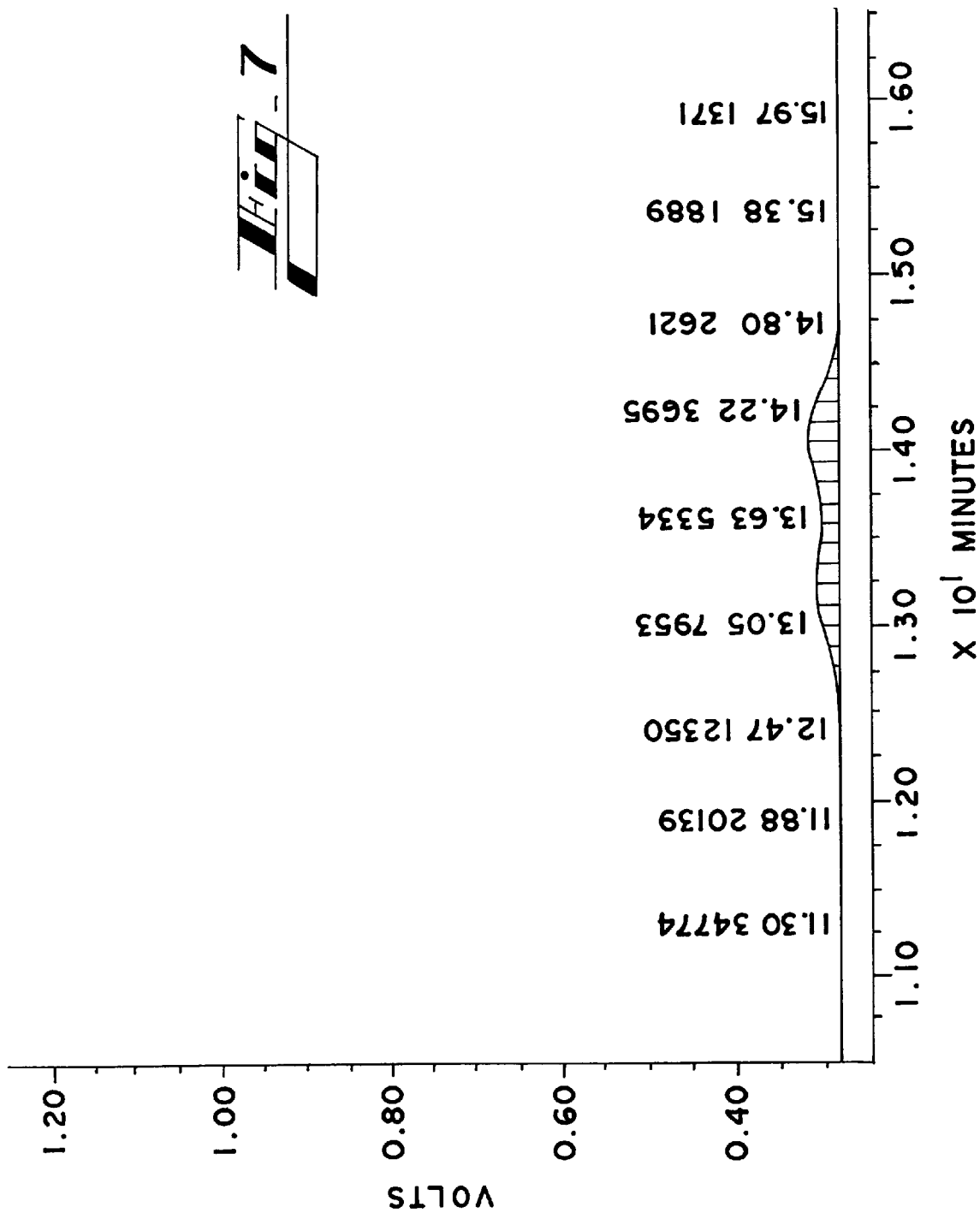
FIG. 7 is a chromatogram of fraction 5 of the poloxamer 188 collected from the chromatographic run described in Example I.

The sample that was collected in Example I was fractionated into five fractions and each fraction was run on the column as described in Example I. The chromatograms from the various chromatographic runs are shown in FIGS. 3 through 8. The fraction that demonstrates the least toxicity while retaining the therapeutic activity of the poloxamer 188 is shown in FIG. 5. As can be clearly seen, the shoulders on either side of the peak in FIG. 5 are absent.

The average molecular weight for each fraction is shown in Table II. The chromatogram for each fraction is indicated in FIGS. 3 through 8.

TABLE II

| Fraction | FIG. | Time off Column (Min) | Molecular Wt. | Polydispersity Value |
|---|---|---|---|---|
| 1 | 3 | 11.5–12.0 | 17000 | 1.0400 |
| 2 | 4 | 12.0–12.5 | 10270 | 1.0474 |
| 3 | 5 | 12.5–13.0 | 8964 | 1.0280 |
| 4 | 6 | 13.0–13.5 | 8188 | 1.0332 |
| 5 | 7 | 13.5–14.0 | 5418 | 1.1103 |
| 6 | 8 | 14.0–14.5 | 3589 | 1.0459 |

The polydispersity value for the unfractionated poloxamer 188 is 1.0896. The fraction that most closely corresponds to poloxamer 188 is fraction 3 which has a polydispersity value of approximately 1.0280.

EXAMPLE III

In a one-liter 3 neck round bottom flask equipped with a mechanical stirrer, reflux condenser, thermometer and propylene oxide feed inlet, there is placed 57 grams (0.75 mol) of propylene glycol and 7.5 grams of anhydrous sodium hydroxide. The flask is purged with nitrogen to remove air and heated to 120° C. with stirring until the sodium hydroxide is dissolved. Sufficient propylene oxide is introduced into the mixture as fast as it reacts until the product possesses a calculated molecular weight of approximately 1750 daltons. The product is cooled under nitrogen and the NaOH catalyst is neutralized with sulfuric acid and the product is then filtered. The final product is a water-insoluble polyoxypropylene glycol.

EXAMPLE IV

The polyoxypropylene glycol from Example III is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the commercially prepared poloxamer 188 copolymer. The chromatographic system is equipped with two LiChrogel PS-40 columns and a LiChrogel PS-20 column in series (EM Science, Gibbstown, N.J.). The LiChrogel PS-40 columns are 10 $\mu$m particle size and the LiChrogel PS-20 column is 5 $\mu$m particle size. All columns are 7 mm by 25 cm in size.

200$\mu$L (4mg) of the polyoxypropylene glycol in tetrahydrofuran is added to the column and the sample is run with the columns and the detector at 40° C. The fraction which corresponded to an average molecular weight of 1750 daltons with a molecular weight distribution between 1,000 and 2,600 daltons was collected. Other fractions were discarded.

EXAMPLE V

The purified polyoxypropylene glycol from Example IV was placed in the same apparatus as described in Example III with an appropriate amount of anhydrous sodium hydroxide. An appropriate amount of ethylene oxide was added at an average temperature of 120° C. using the same technique described in Example III. The amount of added ethylene oxide corresponded to 20% of the total weight of the polyoxypropylene glycol base plus the weight of added ethylene oxide.

This procedure results in a polyoxypropylene/polyoxyethylene block copolymer composed of molecules which are far more homogeneous relative to molecular size and configuration compared to commercial preparations.

EXAMPLE VI

Fractions of poloxamer 760.5 prepared by gel permeation chromatography and were analyzed for weight percent of oxyethylene and for unsaturation by NMR analysis as follows: Poloxamer 760.5 (BASF Corporation, Parsippany N.J.) is dissolved in tetrahydrofuran at a concentration of 20 mg/mL. A Model 600E Powerline chromatographic system equipped with a column heater module, a Model 410 refractive index detector and Maxima 820 software package (all from Waters, Div. of Millipore, Milford, Mass.) is used to fractionate the conmmercially prepared poloxamer 760.5 copolymer. The chromatographic system is equipped with Ultrastyragel 103 A and 500 A in series (Waters, Div. of Millipore, Milford, Mass.). Column size is 7.8 mm internal diameter by 30 cm. Precolumn filters #A-315 with removable 2$\mu$m fits (Upchurch Scientific, Oak Harbor, Wash.) were used for protection of the columns. 200$\mu$L (4mg) of the poloxamer 760.5 in tetrahydrofuran is added to the column and the sample is run with the columns at 40° C. and the detector at 45° C.

Figure 9C:
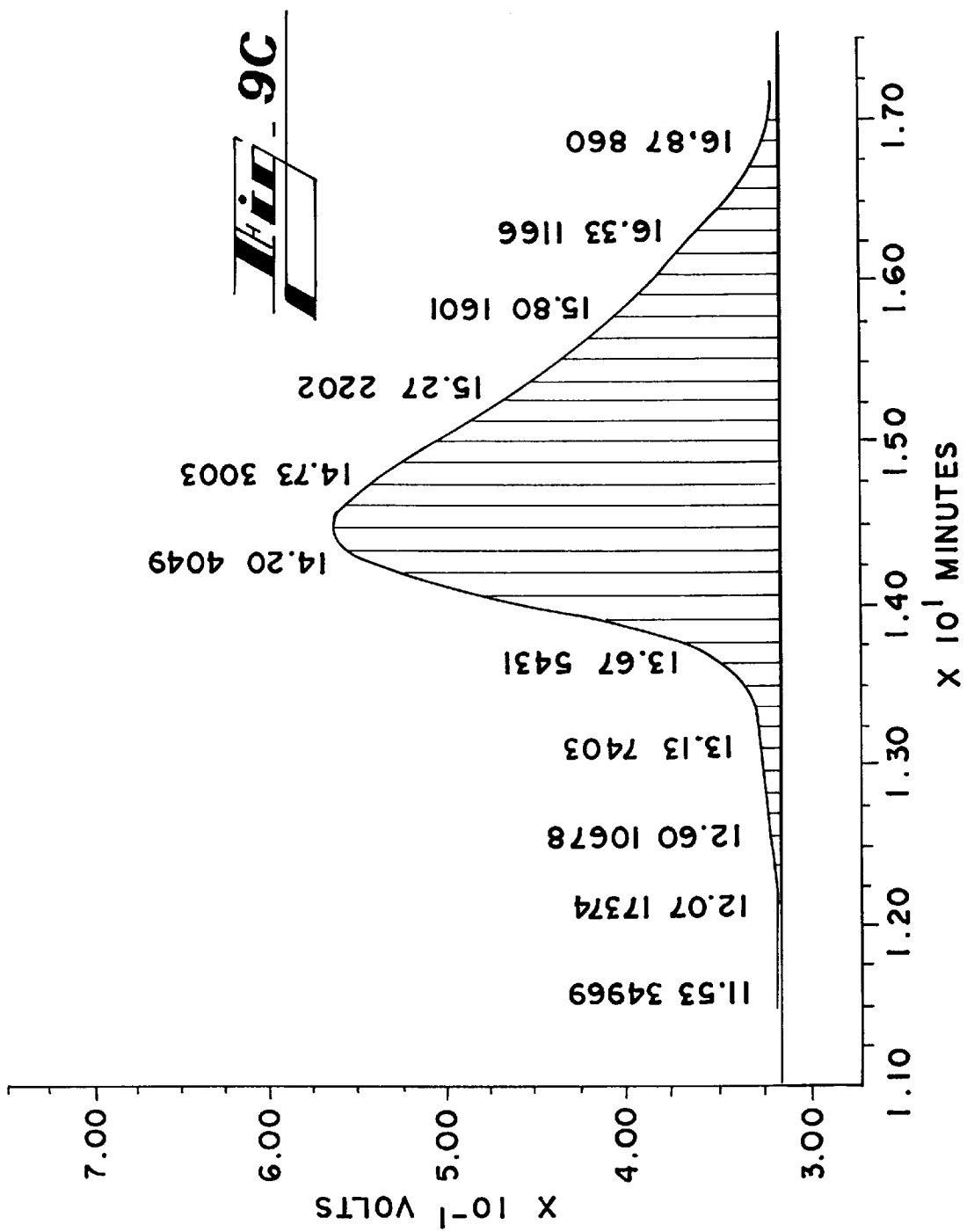
Figure 10A:
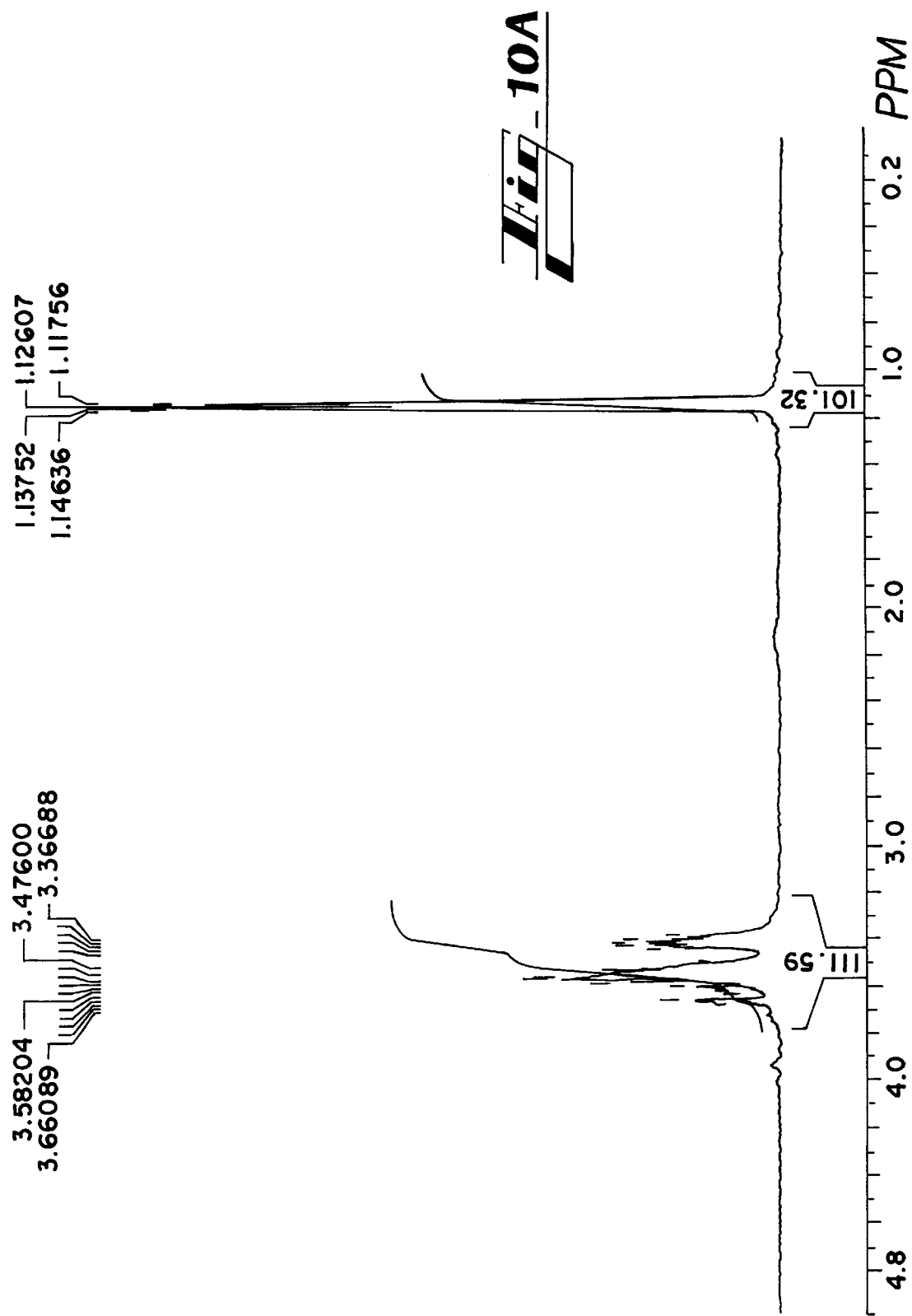
Figure 10C:
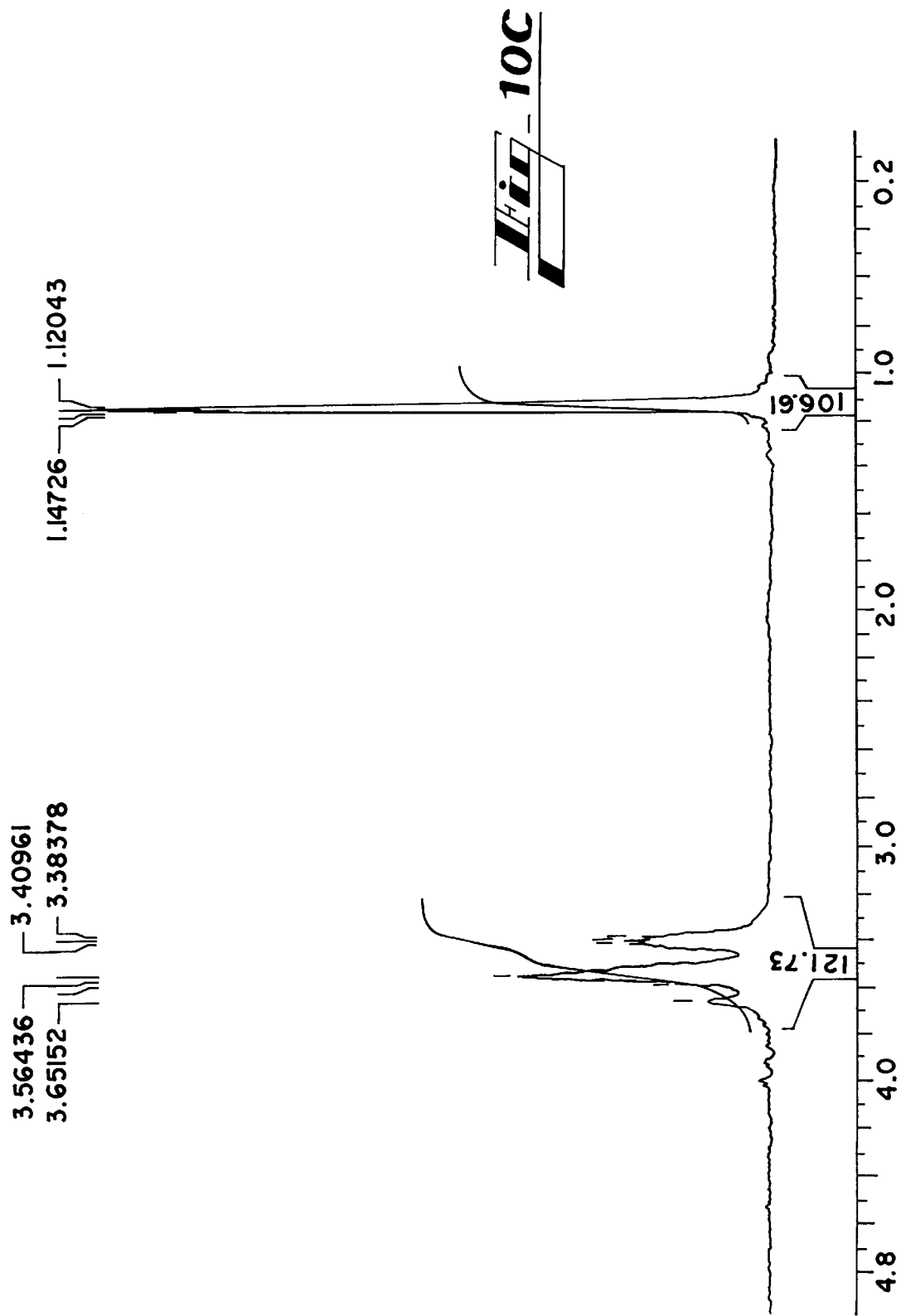

Sample one is an unfractionated sample of the polaxamer 760.5 as obtained from BASF Corporation (Parsipanny, N.J.) and is shown in FIG. 9A. Fraction one is an early fraction from the chromatographic system and is shown in FIG. 9B. Fraction two is a late fraction and is shown in FIG. 9C. All proton NMR analyses were performed in accordance with the NF procedure "Weight Percent Oxyethylene" on a Bruker 300 MHz instrument.

The proton nuclear magnetic resonance spectra from FIGS. 9B and 9C showed slight ban broadening in the spectra when compared to the unfractionated sample. The late eluting fraction (Fraction 2) contains the largest amount of unsaturation as noted by a doublet signal at about 4.0 ppm. The proton spectra for the early eluting peak (Fraction 1) showed no impurities except water.

The weight percent oxyethylene was calculated for the samples. As can be seen from Table III, the early eluting fraction, which is the purest fraction, has the lowest percentage of oxyethylene. This fraction also showed no unsaturation as measured by nuclear magnetic resonance. Using the poloxamer nomenclature system described above, the various fractions have the following characteristics and poloxamer number.

TABLE III

| Fraction | % POE[a] | MW[b] | Poloxamer | Unsaturation[c] |
|---|---|---|---|---|
| Unfractionated | 5.5 | 8135 | 760.5 | Yes |
| Early Fraction | 3.9 | 10856 | 104.4 | No |
| Late Fraction | 7.5 | 3085 | 291 | Yes | a. As measured by NMR
b. Polyoxypropylene as measured by gel permeation chromatography
c. As measured by NMR

EXAMPLE VII

Figure 11B:
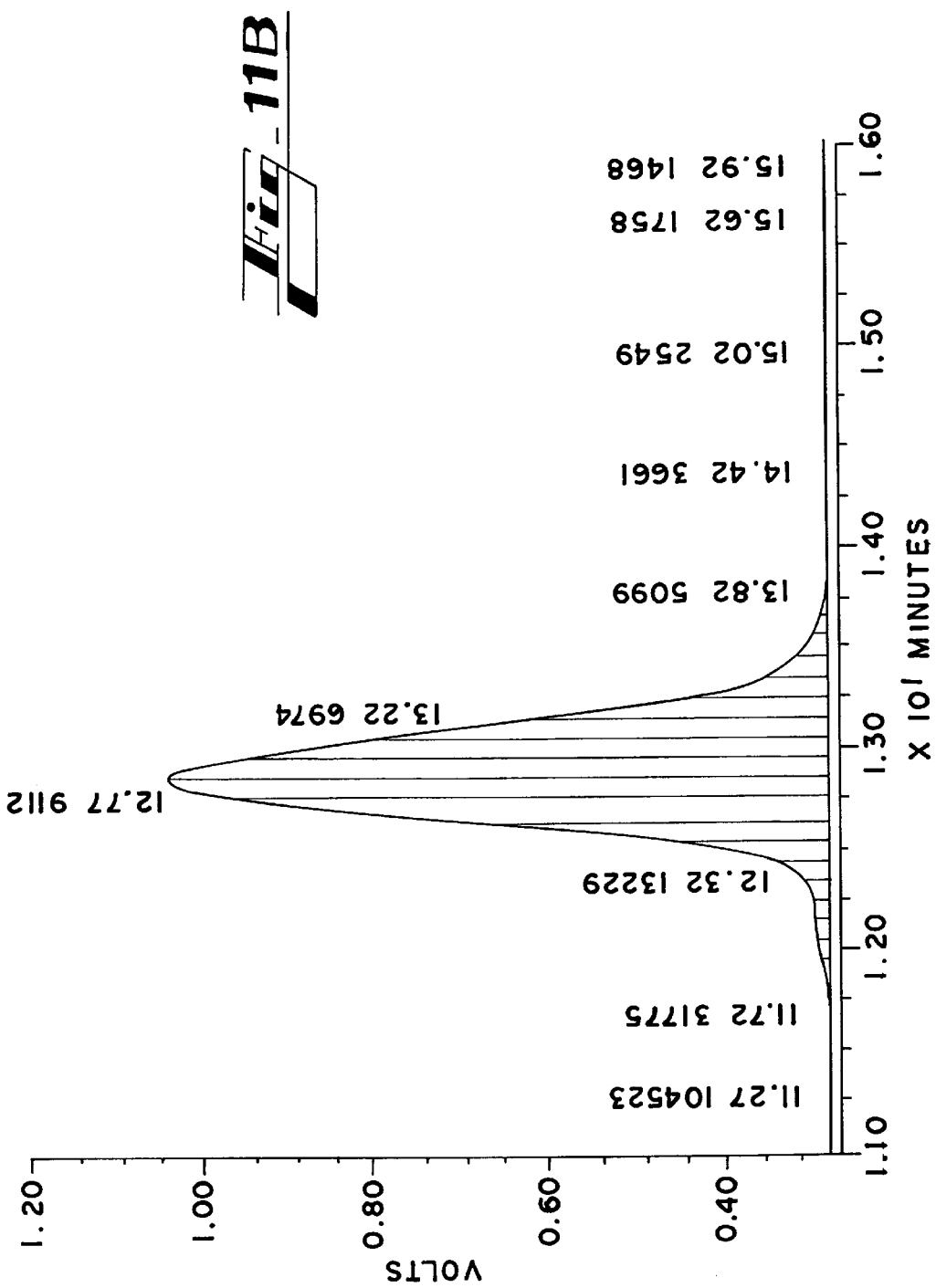
Figure 11C:
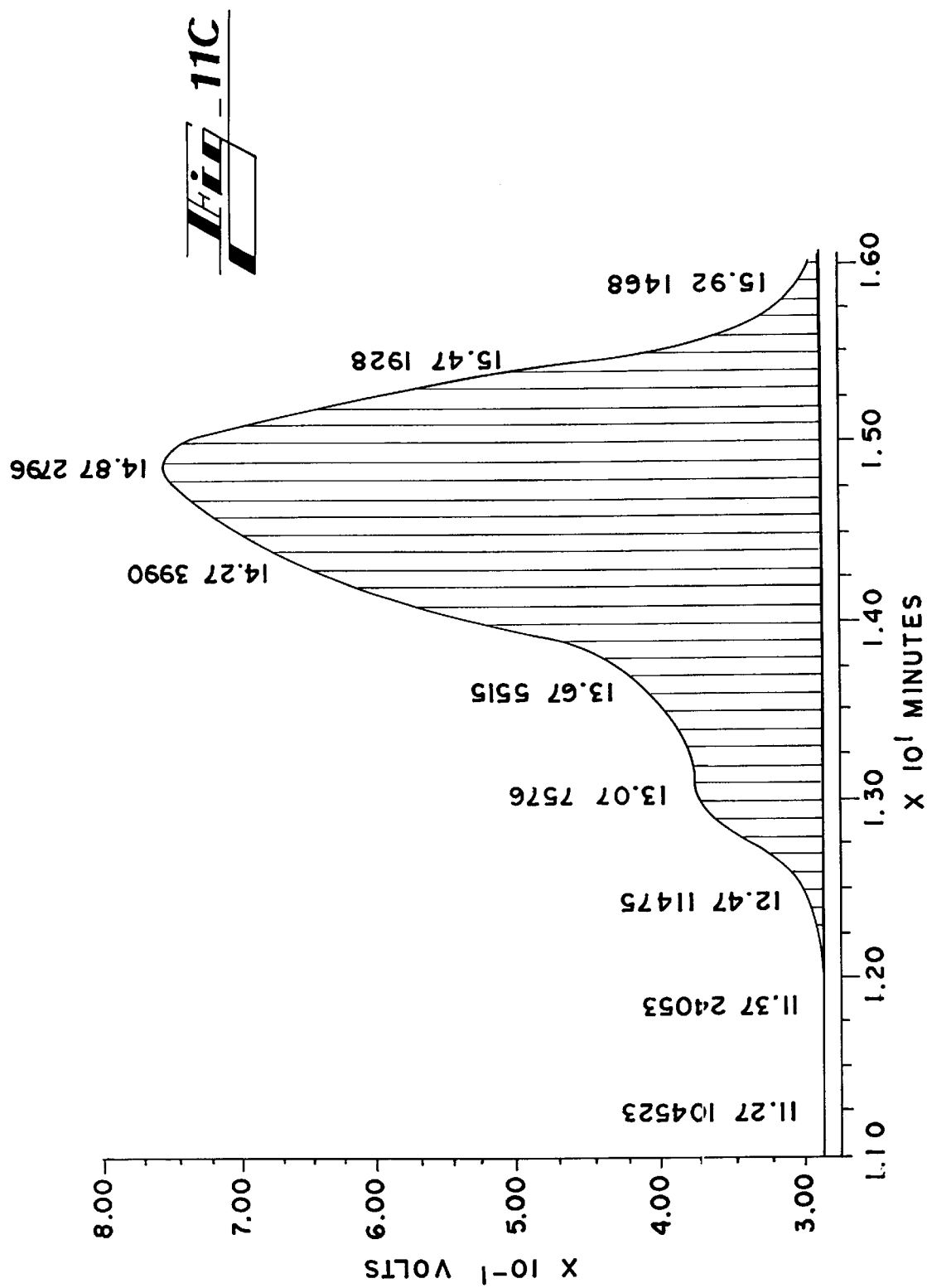

Poloxamer 188 (Pluronic® F68) was fractionated on a gel permeation chromatography system according to Example I. Three fractions were collected. FIG. 11A shows Fraction 1, an early, high molecular weight fraction. FIG. 11B shows Fraction II, which is the major peak. FIG. 11C shows Fraction III, a late eluting, lower molecular weight population of molecules. The percent oxyethylene of each fraction was determined by proton NMR using a 200 MHz NMR spectrophotometer. Approximately 10 mg of each sample was tested. Samples were prepared by adding approximately 0.7 mL of CDCl₃ to each vial. The solution was filtered and transferred to a 5-mm NMR tube. One drop of D₂O was added, and the tube was shaken prior to measurement.

TABLE IV

| Fraction | % POE[a] | MW[b] | Poloxamer |
|---|---|---|---|
| Early | 85 | 16,500 | 258 |
| Middle Fraction | 82 | 8652 | 178 |
| Late Fraction | 90 | 3751 | 039 | a. As measured by NMR
b. As measured by gel permeation chromatography

As shown in Table IV, the early eluting, the large molecular weight fraction had a high percentage of oxyethylene and corresponded to a poloxamer 258. The middle fraction had the smallest percentage of oxyethylene while the late eluting, small molecular weight fraction had the highest percentage of oxyethylene. The middle fraction had a calculated poloxamer number of 178 which corresponds closely to the desired number of 188. The late fraction had a calculated poloxamer number of 039. Thus, the commercially available poloxamer preparation has a significant population of polymers which may be harmful in a biological system.

EXAMPLE VIII

Figure 12A:
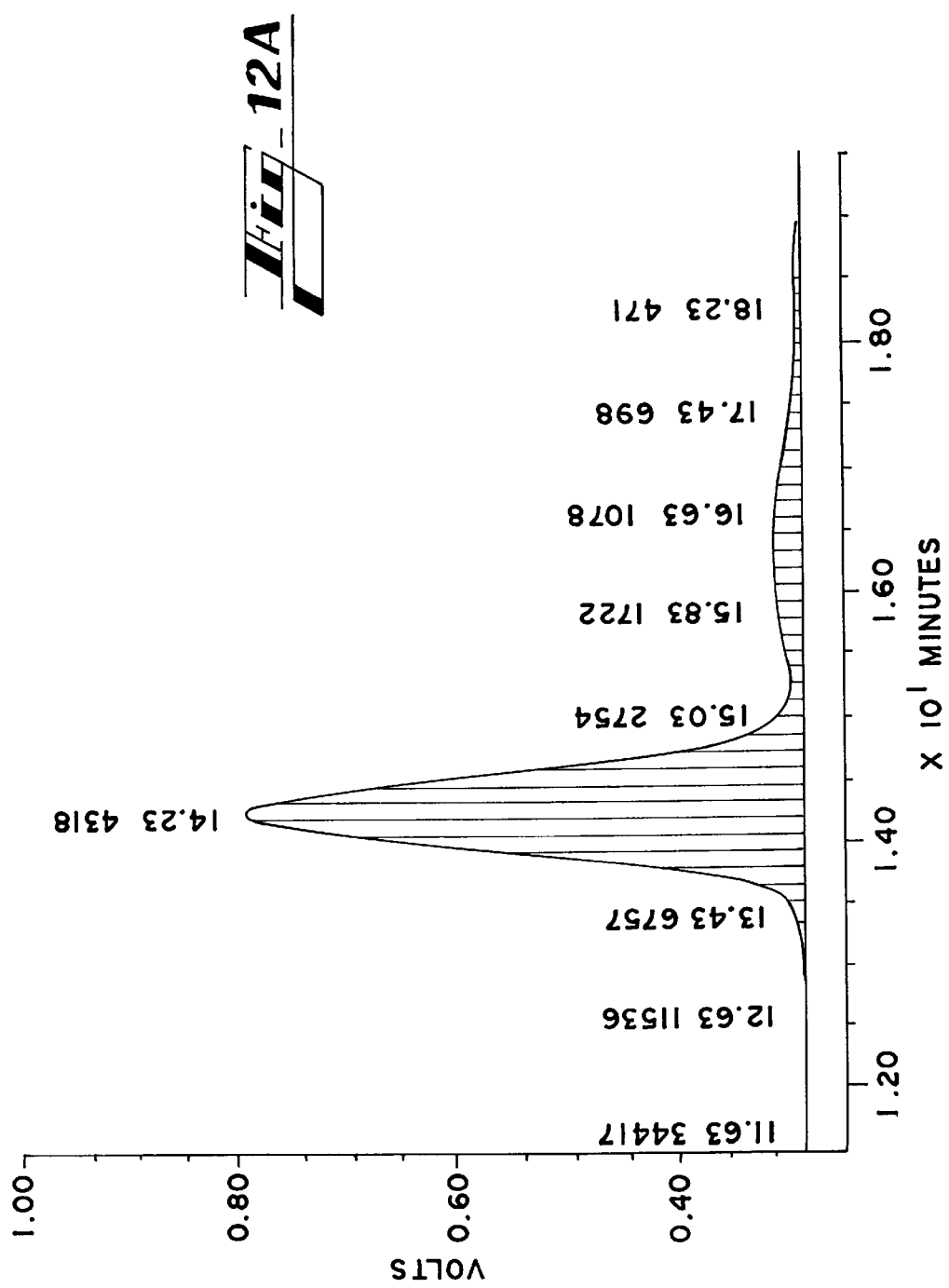
FIGS. 12A through 12C are gel permeation chromatograms of unfractionated and fractionated poloxamer 331.
Figure 12B:
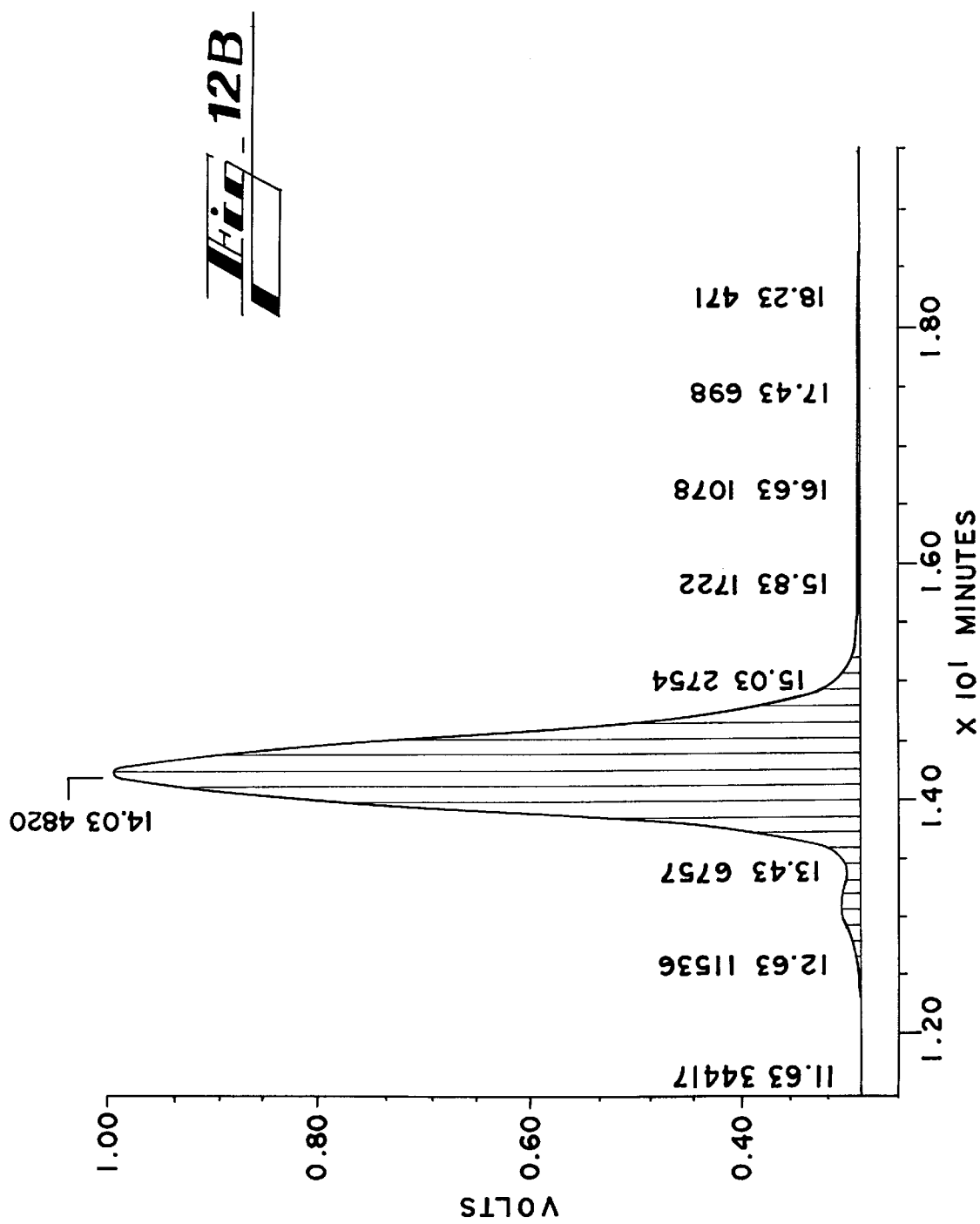
Figure 12C:
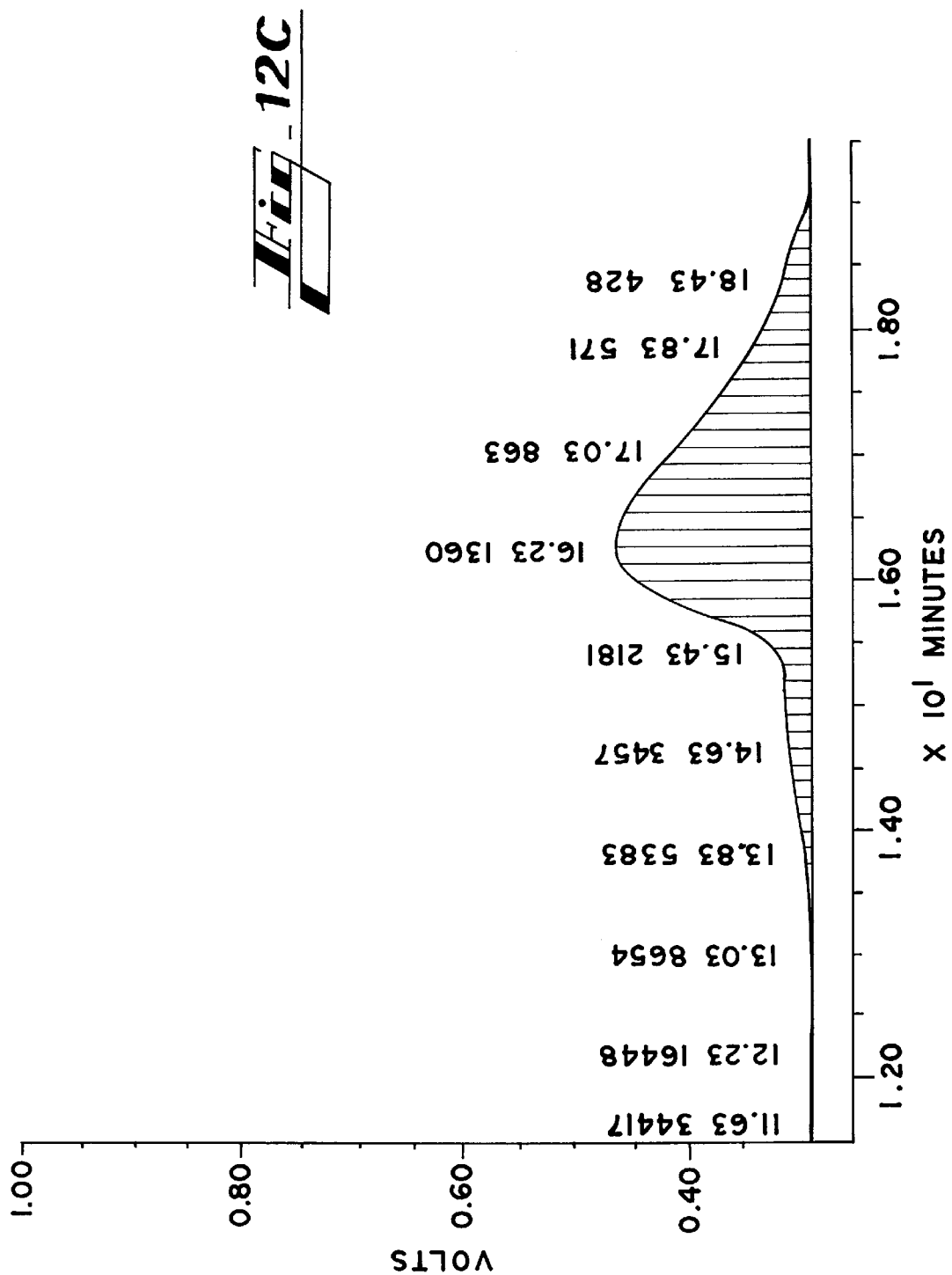

Poloxamer 331 (Pluronic® L101) was fractionated according to the protocol in Example VI. The chromatographs for unfractionated poloxamer 331, an early eluting fraction and a late eluting fraction are shown in FIGS. 12A through 12C respectively. The NMR spectra for each sample was then determined as in Example VI. The results of these spectra and chromatograms are summarized in Table V.

TABLE V

| Fraction | % POE[a] | MW[b] | Poloxamer | Unsaturation[c] |
|---|---|---|---|---|
| Unfractionated | 17 | 4045 | 342 | Yes |
| Early Fraction | 15 | 4452 | 381 | No |
| Late Fraction | 31 | 1466 | 103 | Yes | a. As measured by NMR
b. As measured by gel permeation chromatography
c. As measured by NMR When the poloxamer number for each fraction is calculated based on the empirical data collected, it is seen that the late fraction polymer is a very different poloxamer than the unfractionated preparation. In addition, the unsaturated population of polymers has been removed by the fractionation procedure.

It should be understood that the foregoing relates only to a preferred embodiment of the present invention and that numerous modifications or alterations may be made therein without departing from the spirit and the scope of the invention as set forth in the appended claims.

[1] Adamson, AW, PHYSICAL CHEMISTRY OF SURFACES. 4th Ed., John Wiley & Sons, New York (1982).
[2] See generally, HEMOSTASIS AND THROMBOSIS, BASIC PRINCIPLES AND CLINICAL PRACTICE, ed. by Colman, et al., J. B. Lipincott Company (1987)
[3] Atkinson, T P, et al., "", AM. J. PHYSIOL. 254:C20 (1988).
[4] Brooks, D E, and Evans, E A, Rheology of blood cells in CLINICAL HEMORHEOLOGY, Applications in Cardiovascular and Hematological Disease, Diabetes, Surgery and Gynecology. S. Chien, J. Dormandy, E. Ernst, and A. Matrai, eds, Martinus Nijhoff Publishers, Dordrecht (1987).
[5] Thompson, A R, and Harker, L A, MANUAL OF HEMOSTASIS AND THROMBOSIS, Edition 3, F. A. Davis Company, Philadelphia (1983).
[6] Lee, L H, "Effect of surface energetics on polymer friction and wear", in ADVANCES IN POLYMER FRICTION AND WEAR, Polymer Science and Technology, Vol. 5A. L. H Lee, editor, Plenum Press, New York (1974).
[7] Brooks and Evans (1987), supra
[8] Lee, (1974), supra
[9] Adamson, (1982), supra
[10] Grover, F. L., et al., "A nonionic surfactant and blood viscosity", ARCH SURG, 106:307 (1973).
[11] Papadea, C. and Hunter, R., "Effect of RheothRx® copolymer on blood viscosity related to fibrin(ogen) concentration", FASEB J 2:A384 (1988).
[12] Wiman, B. and Rinby, M., "Determination of soluble fibrin in plasma by a rapid and quantitative spectrophotometric assay", TOMB. HAEMOST, 55:189 (1986).
[13] Connaghan, D G, Francis, C W, Lane, D A, and Marder, V J, "Specific identification of fibrin polymers, fibrinogen degradation products, and cross-linked fibrin degradation products in plasma and serum with a new sensitive technique", BLOOD, 65:589 (1985).
[14] Wiman, B. and Ranby, M., "Determination of soluble fibrin in plasma by a rapid and quantitative spectrophotometric assay", THROMB. HAEMOST. 55:189 (1986).
[15] Vercellotte, G. M, et al., "Activation of Plasma Complement by Perfluorocarbon Artificial Blood: Probable Mechanism of Adverse Pulmonary Reactions in Treated Patients and Rationale for Corticosteroid Prophylaxis", BLOOD, Vol. 59, pp. 1299–1304 (1982).
[16] Lane, T. A., et al., "Paralysis of phagocyte migration due to an artificial blood substitute", BLOOD, Vol. 64, pp. 400–405 (1984).
[17] Lane, T. A., et al., "Reduction in the toxicity of a component of an artificial blood substitute by supercritical fluid fractionation", TRANSFUSION, Vol. 28, pp. 375–378 (1987).
[18] Lane, T. A., et al., "Reduction in the toxicity of a component of an artificial blood substitute by supercritical fluid fractionation", TRANSFUSION, Vol. 28, pp. 375–378 (1987).
[19] Hunter, et al., "The Adjuvant Activity of Nonionic Block Polymer Surfactants, mI. Characterization of Selected Biologically Active Surfaces", SCAND. J. IMMUNOL., Vol. 23, PP. 28–300 (1986).
[20] Henry, R. L., et al., "Burn Wound Coverings and the Use of Poloxamer Preparations", CRITICAL REVIEWS IN BIOCOMPATIBILITY, Vol. 5, No. 3, pp. 207–220 (1989).

We claim:

1. A substantially pure polyoxypropylene/polyoxyethylene block copolymer composition, wherein said substantially pure polyoxypropylene/polyoxyethylene block copolymer composition has less unsaturation than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 Daltons and 15,000 Daltons and b is an integer such that the molecular weight represented by the polyoxyethylene portion of the respective block copolymer constitutes between 5% and 95% of the respective block copolymer and the polydispersity value is less than approximately 1.07.

2. A substantially pure polyoxypropylene/polyoxyethylene block copolymer composition of claim 1, wherein the polyoxypropylene portion of the respective block copolymer has a molecular weight range of between 1,200 Daltons and 6,500 Daltons.

3. A substantially pure polyoxypropylene/polyoxyethylene block copolymer composition of claim 1, wherein the polyoxyethylene portion of the respective block copolymer constitutes between 10% and 95% of the respective block copolymer.

4. A substantially pure polyoxypropylene/polyoxyethylene block copolymer composition of claim 1, wherein the polyoxyethylene portion of the respective block copolymer constitutes between 5% and 15% of the respective block copolymer.

5. A substantially pure polyoxypropylene/polyoxyethylene block copolymer composition of claim 1, wherein the polyoxyethylene portion of the respective block copolymer constitutes 20% of the respective block copolymer.

6. A substantially pure polyoxypropylene/polyoxyethylene block copolymer composition of claim 1, wherein a and b are selected such that the average total molecular weight of said substantially pure block copolymer composition is between 5,000 Daltons and 15,000 Daltons.

7. A substantially pure polyoxypropylene/polyoxyethylene block copolymer composition of claim 2, wherein a and b are selected such that the average total molecular weight of said substantially pure block copolymer composition is between 5,000 Daltons and 15,000 Daltons.

8. A substantially pure polyoxypropylene/polyoxyethylene block copolymer composition of claim 3, wherein a and b are selected such that the average total molecular weight of said substantially pure block copolymer composition is between 5,000 Daltons and 15,000 Daltons.

9. A substantially pure polyoxypropylene/polyoxyethylene block copolymer composition of claim 5, wherein a and b are selected such that the average total molecular weight of said substantially pure block copolymer composition is between 5,000 Daltons and 15,000 Daltons.

10. A substantially pure polyoxypropylene/polyoxyethylene block copolymer composition of claim 4, wherein the average total molecular weight of said substantially pure block copolymer composition is between 3,000 Daltons and 5,500 Daltons.

11. A substantially pure polyoxypropylene/polyoxyethylene block copolymer composition of claim 4, wherein the average total molecular weight of said substantially pure block copolymer composition is between 4,500 Daltons and 5,500 Daltons.

12. A substantially pure polyoxypropylene/polyoxyethylene block copolymer composition of claim 1, wherein a is an integer such that the molecular weight of the polyoxypropylene portion of the respective block copolymer is 1,750 Daltons and the average total molecular weight of said substantially pure block copolymer composition is between 8,300 Daltons and 9,400 Daltons.

13. A substantially pure polyoxypropylene/polyoxyethylene block copolymer composition of claim 1, wherein a is an integer such that the molecular weight of the polyoxypropylene portion of the respective block copolymer is 1,750 Daltons and the average total molecular weight of said substantially pure block copolymer composition is 8,400 Daltons.

14. A substantially pure polyoxypropylene/polyoxyethylene block copolymer composition of claim 2, wherein a is an integer such that the molecular weight of the polyoxypropylene portion of the respective block copolymer is 1,750 Daltons and the average total molecular weight of said substantially pure block copolymer composition is 8,400 Daltons.

15. A substantially pure polyoxypropylene/polyoxyethylene block copolymer composition of claim 3, wherein a is an integer such that the molecular weight of the polyoxypropylene portion of the respective block copolymer is 1,750 Daltons and the average total molecular weight of said substantially pure block copolymer composition is 8,400 Daltons.

16. A substantially pure polyoxypropylene/polyoxyethylene block copolymer composition of claim 5, wherein a is an integer such that the molecular weight of the polyoxypropylene portion of the respective block copolymer is 1,750 Daltons and the average total molecular weight of said substantially pure block copolymer composition is 8,400 Daltons.

17. A substantially pure polyoxypropylene/polyoxyethylene block copolymer composition of claim 1, wherein the average total molecular weight of said substantially pure block copolymer composition is between 5,000 Daltons and 15,000 Daltons and b is an integer such that the molecular weight represented by the polyoxyethylene portion of the respective block copolymer constitutes between 75% and 85% of the respective block copolymer.

18. A substantially pure polyoxypropylene/polyoxyethylene block copolymer composition of claim 17, wherein b is an integer such that the molecular weight represented by the polyoxyethylene portion of the respective block copolymer constitutes 80% of the respective block copolymer.

19. A substantially pure polyoxypropylene/polyoxyethylene block copolymer composition of claim 6, wherein the average total molecular weight of said substantially pure block copolymer composition is between 7,000 and 12,000 Daltons.

20. A substantially pure polyoxypropylene/polyoxyethylene block copolymer composition of claim 7, wherein the average total molecular weight of said substantially pure block copolymer composition is between 7,000 and 12,000 Daltons.

21. A substantially pure polyoxypropylene/polyoxyethylene block copolymer composition of claim 8, wherein the average total molecular weight of said substantially pure block copolymer composition is between 7,000 and 12,000 Daltons.

22. A substantially pure polyoxypropylene/polyoxyethylene block copolymer composition of claim 9, wherein the average total molecular weight of said substantially pure block copolymer composition is between 7,000 and 12,000 Daltons.

23. A substantially pure polyoxypropylene/polyoxyethylene block copolymer composition of claim 18, wherein the average total molecular weight of said substantially pure block copolymer composition is between 7,000 and 12,000 Daltons.

24. A substantially pure polyoxypropylene/polyoxyethylene block copolymer composition of claim 1, wherein a is an integer such that the molecular weight of the polyoxypropylene portion of the respective block copolymer is 9,700 Daltons and the average total molecular weight of said substantially pure block copolymer composition is 10,000 Daltons.

25. A substantially pure polyoxypropylene/polyoxyethylene block copolymer composition of claim 1, wherein a is an integer such that the molecular weight of the polyoxypropylene portion of the respective block copolymer is 3,400 Daltons and the average total molecular weight of said substantially pure block copolymer composition is 4,000 Daltons.

26. A substantially pure polyoxypropylene/polyoxyethylene block copolymer composition of claim 1, wherein a is an integer such that the molecular weight of the polyoxypropylene portion of the respective block copolymer is between 950 Daltons and 4,000 Daltons and b is an integer such that the molecular weight represented by polyoxeythylene portion of the respective block copolymer constitutes between 50% and 95% of the respective block copolymer.

27. A substantially pure polyoxypropylene/polyoxyethylene block copolymer composition of claim 1, wherein the average total molecular weight of said substantially pure block copolymer composition is between 5,000 Daltons and 15,000 Daltons and a is an integer such that the molecular weight represented by the polyoxypropylene portion of the respective block copolymer constitutes between 15% and 25% of the respective block copolymer.

28. A substantially pure polyoxypropylene/polyoxyethylene block copolymer composition of claim 1, wherein the average total molecular weight of said substantially pure block copolymer composition is between 1,200 Daltons and 5,300 Daltons and a is an integer such that the molecular weight represented by the polyoxypropylene portion of the respective block copolymer constitutes between 10% and 50% of the respective block copolymer.

29. A substantially pure polyoxypropylene/polyoxyethylene block copolymer composition of claim 28, wherein the average total molecular weight of said substantially pure block copolymer composition is between 1,750 Daltons and 4,500 Daltons.

30. A substantially pure polyoxypropylene/polyoxyethylene block copolymer composition of claim 1, wherein the average total molecular weight of said substantially pure block copolymer composition is between 1,000 Daltons and 2,600 Daltons and a is an integer such that the molecular weight represented by the polyoxypropylene portion of the respective block copolymer constitutes 20% of the respective block copolymer.

31. A substantially pure polyoxypropylene/polyoxyethylene block copolymer composition of claim 30, wherein the average total molecular weight of said substantially pure block copolymer composition is between 1,200 Daltons and 2,400 Daltons.

32. A substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

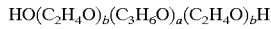

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein at least one impurity contains unsaturation; and
(b) substantially removing the at least one impurity from the non-purified block copolymer composition resulting in said substantially pure polyoxypropylene/polyoxyethylene block copolymer composition which thereby has the property of having less unsaturation than the non-purified copolymer composition from which said substantially pure polyoxypropylene/polyoxyethylene block copolymer composition is derived.

33. A method of making a substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

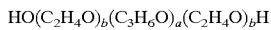

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein at least one impurity contains unsaturation; and
(b) substantially removing the at least one impurity from the non-purified block copolymer composition resulting in said substantially pure polyoxypropylene/polyoxyethylene block copolymer composition which thereby has the property of having less unsaturation than the non-purified copolymer composition from which said substantially pure polyoxypropylene/polyoxyethylene block copolymer composition is derived.

34. A substantially pure polyoxypropylene/polyoxyethylene block copolymer composition, wherein said substantially pure polyoxypropylene/polyoxyethylene block copolymer composition is less renal toxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

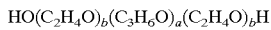

wherein a is an integer such that the molecular weight represented by the polyoxypropylene portion of the respective block copolymer is between 900 daltons and 15,000 daltons and b is an integer such that the molecular weight represented by the polyoxyethylene portion of the respective block copolymer constitutes between 5% and 95% of the respective block copolymer.

35. A substantially pure polyoxypropylene/polyoxyethylene block copolymer composition, wherein said substantially pure polyoxypropylene/polyoxyethylene block copolymer composition has less truncated polymer chains than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion of the respective block copolymer constitutes between 5% and 95% of the respective block copolymer.

36. A substantially pure polyoxypropylene/polyoxyethylene block copolymer composition, wherein said substantially pure polyoxypropylene/polyoxyethylene block copolymer composition is less cytotoxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion of the respective block copolymer constitutes between 5% and 95% of the respective block copolymer.

37. A substantially pure polyoxypropylene/polyoxyethylene block copolymer composition, wherein said substantially pure polyoxypropylene/polyoxyethylene block copolymer composition has less detergent-like activity than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion of the respective block copolymer constitutes between 5% and 95% of the respective block copolymer.

38. A substantially pure polyoxypropylene/polyoxyethylene block copolymer composition, wherein said substantially pure polyoxypropylene/polyoxyethylene block copolymer composition is less renal toxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein the average total molecular weight of said substantially pure block copolymer composition is between 5,000 and 15,000 Daltons and b is an integer such that the molecular weight represented by the polyoxyethylene portion of the respective block copolymer constitutes between 5% and 95% of the respective block copolymer.

39. A substantially pure polyoxypropylene/polyoxyethylene block copolymer composition, wherein said substantially pure polyoxypropylene/polyoxyethylene block copolymer composition has less truncated polymer chains than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein the average total molecular weight of said substantially pure block copolymer composition is between 5,000 and 15,000 Daltons and b is an integer such that the molecular weight represented by the polyoxyethylene portion of the respective block copolymer constitutes between 5% and 95% of the respective block copolymer.

40. A substantially pure polyoxypropylene/polyoxyethylene block copolymer composition, wherein said substantially pure polyoxypropylene/polyoxyethylene block copolymer composition is less cytotoxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein the average total molecular weight of said substantially pure block copolymer composition is between 5,000 and 15,000 Daltons and b is an integer such that the molecular weight represented by the polyoxyethylene portion of the respective block copolymer constitutes between 5% and 95% of the respective block copolymer.

41. A substantially pure polyoxypropylene/polyoxyethylene block copolymer composition, wherein said substantially pure polyoxypropylene/polyoxyethylene block copolymer composition has less detergent-like activity than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein the average total molecular weight of said substantially pure block copolymer composition is between 5,000 and 15,000 Daltons and b is an integer such that the molecular weight represented by the polyoxyethylene portion of the respective block copolymer constitutes between 5% and 95% of the respective block copolymer.

42. A substantially pure polyoxypropylene/polyoxyethylene block copolymer composition, wherein said substantially pure polyoxypropylene/polyoxyethylene block copolymer composition has less unsaturation than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein the average total molecular weight of said substantially pure block copolymer composition is between 5,000 and 15,000 Daltons and b is an integer such that the molecular weight represented by the polyoxyethylene portion of the respective block copolymer constitutes between 5% and 95% of the respective block copolymer.

43. A substantially pure polyoxypropylene/polyoxyethylene block copolymer composition, wherein said substantially pure polyoxypropylene/polyoxyethylene block copolymer composition is less renal toxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H4O)_b(C_3H_6O)_a(C2H4O)_bH$$

wherein b is an integer such that the molecular weight represented by the polyoxyethylene portion of the respective block copolymer constitutes between 5% and 95% of the respective block copolymer, and wherein the substantially pure block copolymer composition comprises greater than 92.2 percent by weight of a middle molecular weight fraction when fractionated by gel chromatography.

44. A substantially pure polyoxypropylene/polyoxyethylene block copolymer composition, wherein said substantially pure polyoxypropylene/polyoxyethylene block copolymer composition has less truncated polymer chains than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein b is an integer such that the molecular weight represented by the polyoxyethylene portion of the respective block copolymer constitutes between 5% and 95% of the respective block copolymer, and wherein the substantially pure block copolymer composition comprises greater than 92.2 percent by weight of a middle molecular weight fraction when fractionated by gel chromatography.

45. A substantially pure polyoxypropylene/polyoxyethylene block copolymer composition, wherein said substantially pure polyoxypropylene/polyoxyethylene block copolymer composition is less cytotoxic than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein b is an integer such that the molecular weight represented by the polyoxyethylene portion of the respective block copolymer constitutes between 5% and 95% of the respective block copolymer, and wherein the substantially pure block copolymer composition comprises greater than 92.2 percent by weight of a middle molecular weight fraction when fractionated by gel chromatography.

46. A substantially pure polyoxypropylene/polyoxyethylene block copolymer composition, wherein said substantially pure polyoxypropylene/polyoxyethylene block copolymer composition has less detergent-like activity than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein b is an integer such that the molecular weight represented by the polyoxyethylene portion of the respective block copolymer constitutes between 5% and 95% of the respective block copolymer, and wherein the substantially pure block copolymer composition comprises greater than 92.2 percent by weight of a middle molecular weight fraction when fractionated by gel chromatography.

47. A substantially pure polyoxypropylene/polyoxyethylene block copolymer composition, wherein said substantially pure polyoxypropylene/polyoxyethylene block copolymer composition has less unsaturation than a corresponding non-pure polyoxypropylene/polyoxyethylene block copolymer composition, said substantially pure polyoxypropylene/polyoxyethylene block copolymer composition containing block copolymers with each of the block copolymers having the following general formula:

$$HO(C_2H_4O)_b(C_3H_6O)_a(C_2H_4O)_bH$$

wherein b is an integer such that the molecular weight represented by the polyoxyethylene portion of the respective block copolymer constitutes between 5% and 95% of the respective block copolymer, and wherein the substantially pure block copolymer composition comprises greater than 92.2 percent by weight of a middle molecular weight fraction when fractionated by gel chromatography.

48. A substantially pure polyoxypropylene/polyoxyethylene block copolymer composition, wherein said substantially pure polyoxypropylene/polyoxyethylene block copolymer composition is prepared by:
  (a) providing a non-purified polyoxypropylene/polyoxyethylene block copolymer composition prepared by first polymerizing propylene oxide and thereafter copolymerizing ethylene oxide therewith which results in the formation of at least
    (1) block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
    (2) at least one impurity resulting from the manufacture of the non-purified block copolymer composition, wherein the impurity has the property of being renal toxic to a human body; and
  (b) substantially removing the at least one impurity from the non-purified block copolymer composition resulting in said substantially pure polyoxypropylene/polyoxyethylene block copolymer composition which thereby has the property of being less renal toxic than the non-purified copolymer composition from which said substantially pure polyoxypropylene/polyoxyethylene block copolymer composition is derived.

49. A substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein the impurity contains truncated polymer chains; and
(b) substantially removing the at least one impurity from the non-purified block copolymer composition resulting in said substantially pure polyoxypropylene/polyoxyethylene block copolymer composition which thereby has the property of having less truncated polymer chains than the non-purified block copolymer composition from which said substantially pure polyoxypropylene/polyoxyethylene block copolymer composition is derived.

50. A substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein the impurity has the property of being cytotoxic to a human body; and
(b) substantially removing the impurity from the non-purified block copolymer composition resulting in said substantially pure polyoxypropylene/polyoxyethylene block copolymer composition which thereby has the property of being less cytotoxic than the non-purified block copolymer composition from which said substantially pure polyoxypropylene/polyoxyethylene block copolymer composition is derived.

51. A substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein the impurity imparts detergent-like activity to the non-purified block copolymer composition; and
(b) substantially removing the impurity from the non-purified block copolymer composition resulting in said substantially pure polyoxypropylene/polyoxyethylene block copolymer composition which thereby has less detergent-like activity than the non-purified block copolymer composition from which said substantially pure polyoxypropylene/polyoxyethylene block copolymer composition is derived.

52. A method of making a substantially pure polyoxypropylene/polyoxyethylene block copolymer composition, wherein said substantially pure polyoxypropylene/polyoxyethylene block copolymer composition is prepared by:
(a) providing a non-purified polyoxypropylene/polyoxyethylene block copolymer composition prepared by first polymerizing propylene oxide and thereafter copolymerizing ethylene oxide therewith which results in the formation of at least
(1) block copolymers with each of the block copolymers having the following general formula:

$$HO(C_2H_4O)_b(C_3H_6O)_a(C_2H_4O)_bH$$

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and
(2) at least one impurity resulting from the manufacture of the non-purified block copolymer composition, wherein the impurity has the property of being renal toxic to a human body; and
(b) substantially removing the impurity from the non-purified block copolymer composition resulting in said substantially pure polyoxypropylene/polyoxyethylene block copolymer composition which thereby has the property of being less renal toxic than the non-purified copolymer composition from which said substantially pure polyoxypropylene/polyoxyethylene block copolymer composition is derived.

53. A method of making a substantially pure polyoxypropylene/polyoxyethylene block copolymer composition, wherein said substantially pure polyoxypropylene/polyoxyethylene block copolymer composition is prepared by:

(a) providing a non-purified polyoxypropylene/polyoxyethylene block copolymer composition prepared by first polymerizing propylene oxide and thereafter copolymerizing ethylene oxide therewith which results in the formation of at least (1) block copolymers with each of the block copolymers having the following general formula:

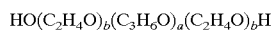

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and (2) at least one impurity resulting from the manufacture of the non-purified block copolymer composition, wherein the impurity contains truncated polymer chains; and (b) substantially removing the impurity from the non-purified block copolymer composition resulting in said substantially pure polyoxypropylene/polyoxyethylene block copolymer composition which thereby has the property of having less truncated polymer chains than the non-purified block copolymer composition from which said substantially pure polyoxypropylene/polyoxyethylene block copolymer composition is derived.

54. A method of making a substantially pure polyoxypropylene/polyoxyethylene block copolymer composition, wherein said substantially pure polyoxypropylene/polyoxyethylene block copolymer composition is prepared by:

(a) providing a non-purified polyoxypropylene/polyoxyethylene block copolymer composition prepared by first polymerizing propylene oxide and thereafter copolymerizing ethylene oxide therewith which results in the formation of at least (1) block copolymers with each of the block copolymers having the following general formula:

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and (2) at least one impurity resulting from the manufacture of the non-purified block copolymer composition, wherein the impurity has the property of being cytotoxic to a human body; and (b) substantially removing the impurity from the non-purified block copolymer composition resulting in said substantially pure polyoxypropylene/polyoxyethylene block copolymer composition which thereby has the property of being less cytotoxic than the non-purified block copolymer composition from which said substantially pure polyoxypropylene/polyoxyethylene block copolymer composition is derived.

55. A method of making a substantially pure polyoxypropylene/polyoxyethylene block copolymer composition, wherein said substantially pure polyoxypropylene/polyoxyethylene block copolymer composition is prepared by:

(a) providing a non-purified polyoxypropylene/polyoxyethylene block copolymer composition prepared by first polymerizing propylene oxide and thereafter copolymerizing ethylene oxide therewith which results in the formation of at least (1) block copolymers with each of the block copolymers having the following general formula:

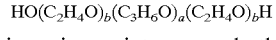

wherein a is an integer such that the molecular weight represented by the polyoxypropylene portion of the respective block copolymer is between 900 daltons and 15,000 daltons and b is an integer such that the molecular weight represented by the polyoxyethylene portion constitutes between 5% and 95% of the respective block copolymer, and (2) at least one impurity resulting from the manufacture of the non-purified block copolymer composition, wherein the impurity imparting detergent-like activity to the non-purified block copolymer composition; and (b) substantially removing the impurity from the non-purified block copolymer composition resulting in said substantially pure polyoxypropylene/polyoxyethylene block copolymer composition which thereby has less detergent-like activity than the non-purified block copolymer composition from which said substantially pure polyoxypropylene/polyoxyethylene block copolymer composition is derived.

56. A substantially pure polyoxypropylene/polyoxyethylene block copolymer composition of claim 34, wherein the polyoxypropylene portion of the respective block copolymer has a molecular weight range of between 1,200 Daltons and 6,500 Daltons.

57. A substantially pure polyoxypropylene/polyoxyethylene block copolymer composition of claim 34, wherein the polyoxyethylene portion of the respective block copolymer constitutes between 10% and 95% of the respective block copolymer.

58. A substantially pure polyoxypropylene/polyoxyethylene block copolymer composition of claim 34, wherein the polyoxyethylene portion of the respective block copolymer constitutes between 5% and 15% of the respective block copolymer.

59. A substantially pure polyoxypropylene/polyoxyethylene block copolymer composition of claim 34, wherein the polyoxyethylene portion of the respective block copolymer constitutes 20% of the respective block copolymer.

60. A substantially pure polyoxypropylene/polyoxyethylene block copolymer composition of claim 34, wherein a and b are selected such that the average total molecular weight of said substantially pure block copolymer composition is between 5,000 Daltons and 15,000 Daltons.

61. A substantially pure polyoxypropylene/polyoxyethylene block copolymer composition of claim 56, wherein a and b are selected such that the average total molecular weight of said substantially pure block copolymer composition is between 5,000 Daltons and 15,000 Daltons.

62. A substantially pure polyoxypropylene/polyoxyethylene block copolymer composition of claim 57, wherein a and b are selected such that the average total molecular weight of said substantially pure block copolymer composition is between 5,000 Daltons and 15,000 Daltons.

63. A substantially pure polyoxypropylene/polyoxyethylene block copolymer composition of claim 59, wherein a and b are selected such that the average total molecular weight of said substantially pure block copolymer composition is between 5,000 Daltons and 15,000 Daltons.

64. A substantially pure polyoxypropylene/ polyoxyethylene block copolymer composition of claim 58, wherein the average total molecular weight of said substantially pure block copolymer composition is between 3,000 Daltons and 5,500 Daltons.

65. A substantially pure polyoxypropylene/ polyoxyethylene block copolymer composition of claim 58, wherein the average total molecular weight of said substantially pure block copolymer composition is between 4,500 Daltons and 5,500 Daltons.

66. A substantially pure polyoxypropylene/ polyoxyethylene block copolymer composition of claim 34, wherein a is an integer such that the molecular weight of the polyoxypropylene portion of the respective block copolymer is 1,750 Daltons and the average total molecular weight of said substantially pure block copolymer composition is between 8,300 Daltons and 9,400 Daltons.

67. A substantially pure polyoxypropylene/ polyoxyethylene block copolymer composition of claim 34, wherein a is an integer such that the molecular weight of the polyoxypropylene portion of the respective block copolymer is 1,750 Daltons and the average total molecular weight of said substantially pure block copolymer composition is 8,400 Daltons.

68. A substantially pure polyoxypropylene/ polyoxyethylene block copolymer composition of claim 56, wherein a is an integer such that the molecular weight of the polyoxypropylene portion of the respective block copolymer is 1,750 Daltons and the average total molecular weight of said substantially pure block copolymer composition is 8,400 Daltons.

69. A substantially pure polyoxypropylene/ polyoxyethylene block copolymer composition of claim 57, wherein a is an integer such that the molecular weight of the polyoxypropylene portion of the respective block copolymer is 1,750 Daltons and the average total molecular weight of said substantially pure block copolymer composition is 8,400 Daltons.

70. A substantially pure polyoxypropylene/ polyoxyethylene block copolymer composition of claim 59, wherein a is an integer such that the molecular weight of the polyoxypropylene portion of the respective block copolymer is 1,750 Daltons and the average total molecular weight of said substantially pure block copolymer composition is 8,400 Daltons.

71. A substantially pure polyoxypropylene/ polyoxyethylene block copolymer composition of claim 34, wherein the average total molecular weight of said substantially pure block copolymer composition is between 5,000 Daltons and 15,000 Daltons and b is an integer such that the molecular weight represented by the polyoxyethylene portion of the respective block copolymer constitutes between 75% and 85% of the respective block copolymer.

72. A substantially pure polyoxypropylene/ polyoxyethylene block copolymer composition of claim 71, wherein b is an integer such that the molecular weight represented by the polyoxyethylene portion of the respective block copolymer constitutes 80% of the respective block copolymer.

73. A substantially pure polyoxypropylene/ polyoxyethylene block copolymer composition of claim 34, wherein the average total molecular weight of said substantially pure block copolymer composition is between 7,000 and 12,000 Daltons.

74. A substantially pure polyoxypropylene/ polyoxyethylene block copolymer composition of claim 56, wherein the average total molecular weight of said substantially pure block copolymer composition is between 7,000 and 12,000 Daltons.

75. A substantially pure polyoxypropylene/ polyoxyethylene block copolymer composition of claim 57, wherein the average total molecular weight of said substantially pure block copolymer composition is between 7,000 and 12,000 Daltons.

76. A substantially pure polyoxypropylene/ polyoxyethylene block copolymer composition of claim 59, wherein the average total molecular weight of said substantially pure block copolymer composition is between 7,000 and 12,000 Daltons.

77. A substantially pure polyoxypropylene/ polyoxyethylene block copolymer composition of claim 72, wherein the average total molecular weight of said substantially pure block copolymer composition is between 7,000 and 12,000 Daltons.

78. A substantially pure polyoxypropylene/ polyoxyethylene block copolymer composition of claim 34, wherein a is an integer such that the molecular weight of the polyoxypropylene portion of the respective block copolymer is 9,700 Daltons and the average total molecular weight of said substantially pure block copolymer composition is 10,000 Daltons.

79. A substantially pure polyoxypropylene/ polyoxyethylene block copolymer composition of claim 34, wherein a is an integer such that the molecular weight of the polyoxypropylene portion of the respective block copolymer is 3,400 Daltons and the average total molecular weight of said substantially pure block copolymer composition is 4,000 Daltons.

80. A substantially pure polyoxypropylene/ polyoxyethylene block copolymer composition of claim 34, wherein a is an integer such that the molecular weight of the polyoxypropylene portion of the respective block copolymer is between 950 Daltons and 4,000 Daltons and b is an integer such that the molecular weight represented by polyoxeythylene portion of the respective block copolymer constitutes between 50% and 95% of the respective block copolymer.

81. A substantially pure polyoxypropylene/ polyoxyethylene block copolymer composition of claim 34, wherein the average total molecular weight of said substantially pure block copolymer composition is between 5,000 Daltons and 15,000 Daltons and a is an integer such that the molecular weight represented by the polyoxypropylene portion of the respective block copolymer constitutes between 15% and 25% of the respective block copolymer.

82. A substantially pure polyoxypropylene/ polyoxyethylene block copolymer composition of claim 34, wherein the average total molecular weight of said substantially pure block copolymer composition is between 1,200 Daltons and 5,300 Daltons and a is an integer such that the molecular weight represented by the polyoxypropylene portion of the respective block copolymer constitutes between 10% and 50% of the respective block copolymer.

83. A substantially pure polyoxypropylene/ polyoxyethylene block copolymer composition of claim 82, wherein the average total molecular weight of said substantially pure block copolymer composition is between 1,750 Daltons and 4,500 Daltons.

84. A substantially pure polyoxypropylene/ polyoxyethylene block copolymer composition of claim 34, wherein the average total molecular weight of said substantially pure block copolymer composition is between 1,000

Daltons and 2,600 Daltons and a is an integer such that the molecular weight represented by the polyoxypropylene portion of the respective block copolymer constitutes 20% of the respective block copolymer.

85. A substantially pure polyoxypropylene/ polyoxyethylene block copolymer composition of claim 84, wherein the average total molecular weight of said substantially pure block copolymer composition is between 1,200 Daltons and 2,400 Daltons.

86. A substantially pure polyoxypropylene/ polyoxyethylene block copolymer composition of claim 34, wherein the average total molecular weight of said substantially pure block copolymer composition is between 6,000 and 13,000 Daltons.

87. A substantially pure polyoxypropylene/ polyoxyethylene block copolymer composition of claim 35, wherein the polyoxypropylene portion of the respective block copolymer has a molecular weight range of between 1,200 Daltons and 6,500 Daltons.

88. A substantially pure polyoxypropylene/ polyoxyethylene block copolymer composition of claim 35, wherein the polyoxyethylene portion of the respective block copolymer constitutes between 10% and 95% of the respective block copolymer.

89. A substantially pure polyoxypropylene/ polyoxyethylene block copolymer composition of claim 35, wherein the polyoxyethylene portion of the respective block copolymer constitutes between 5% and 15% of the respective block copolymer.

90. A substantially pure polyoxypropylene/ polyoxyethylene block copolymer composition of claim 35, wherein the polyoxyethylene portion of the respective block copolymer constitutes 20% of the respective block copolymer.

91. A substantially pure polyoxypropylene/ polyoxyethylene block copolymer composition of claim 35, wherein a and b are selected such that the average total molecular weight of said substantially pure block copolymer composition is between 5,000 Daltons and 15,000 Daltons.

92. A substantially pure polyoxypropylene/ polyoxyethylene block copolymer composition of claim 87, wherein a and b are selected such that the average total molecular weight of said substantially pure block copolymer composition is between 5,000 Daltons and 15,000 Daltons.

93. A substantially pure polyoxypropylene/ polyoxyethylene block copolymer composition of claim 88, wherein a and b are selected such that the average total molecular weight of said substantially pure block copolymer composition is between 5,000 Daltons and 15,000 Daltons.

94. A substantially pure polyoxypropylene/ polyoxyethylene block copolymer composition of claim 90, wherein a and b are selected such that the average total molecular weight of said substantially pure block copolymer composition is between 5,000 Daltons and 15,000 Daltons.

95. A substantially pure polyoxypropylene/ polyoxyethylene block copolymer composition of claim 89, wherein the average total molecular weight of said substantially pure block copolymer composition is between 3,000 Daltons and 5,500 Daltons.

96. A substantially pure polyoxypropylene/ polyoxyethylene block copolymer composition of claim 89, wherein the average total molecular weight of said substantially pure block copolymer composition is between 4,500 Daltons and 5,500 Daltons.

97. A substantially pure polyoxypropylene/ polyoxyethylene block copolymer composition of claim 35, wherein a is an integer such that the molecular weight of the polyoxypropylene portion of the respective block copolymer is 1,750 Daltons and the average total molecular weight of said substantially pure block copolymer composition is between 8,300 Daltons and 9,400 Daltons.

98. A substantially pure polyoxypropylene/ polyoxyethylene block copolymer composition of claim 35, wherein a is an integer such that the molecular weight of the polyoxypropylene portion of the respective block copolymer is 1,750 Daltons and the average total molecular weight of said substantially pure block copolymer composition is 8,400 Daltons.

99. A substantially pure polyoxypropylene/ polyoxyethylene block copolymer composition of claim 87, wherein a is an integer such that the molecular weight of the polyoxypropylene portion of the respective block copolymer is 1,750 Daltons and the average total molecular weight of said substantially pure block copolymer composition is 8,400 Daltons.

100. A substantially pure polyoxypropylene/ polyoxyethylene block copolymer composition of claim 88, wherein a is an integer such that the molecular weight of the polyoxypropylene portion of the respective block copolymer is 1,750 Daltons and the average total molecular weight of said substantially pure block copolymer composition is 8,400 Daltons.

101. A substantially pure polyoxypropylene/ polyoxyethylene block copolymer composition of claim 90, wherein a is an integer such that the molecular weight of the polyoxypropylene portion of the respective block copolymer is 1,750 Daltons and the average total molecular weight of said substantially pure block copolymer composition is 8,400 Daltons.

102. A substantially pure polyoxypropylene/ polyoxyethylene block copolymer composition of claim 35, wherein the average total molecular weight of said substantially pure block copolymer composition is between 5,000 Daltons and 15,000 Daltons and b is an integer such that the molecular weight represented by the polyoxyethylene portion of the respective block copolymer constitutes between 75% and 85% of the respective block copolymer.

103. A substantially pure polyoxypropylene/ polyoxyethylene block copolymer composition of claim 102, wherein b is an integer such that the molecular weight represented by the polyoxyethylene portion of the respective block copolymer constitutes 80% of the respective block copolymer.

104. A substantially pure polyoxypropylene/ polyoxyethylene block copolymer composition of claim 35, wherein the average total molecular weight of said substantially pure block copolymer composition is between 7,000 and 12,000 Daltons.

105. A substantially pure polyoxypropylene/ polyoxyethylene block copolymer composition of claim 87, wherein the average total molecular weight of said substantially pure block copolymer composition is between 7,000 and 12,000 Daltons.

106. A substantially pure polyoxypropylene/ polyoxyethylene block copolymer composition of claim 88, wherein the average total molecular weight of said substantially pure block copolymer composition is between 7,000 and 12,000 Daltons.

107. A substantially pure polyoxypropylene/ polyoxyethylene block copolymer composition of claim 90, wherein the average total molecular weight of said substantially pure block copolymer composition is between 7,000 and 12,000 Daltons.

108. A substantially pure polyoxypropylene/ polyoxyethylene block copolymer composition of claim 103, wherein the average total molecular weight of said substantially pure block copolymer composition is between 7,000 and 12,000 Daltons.

109. A substantially pure polyoxypropylene/ polyoxyethylene block copolymer composition of claim 35, wherein a is an integer such that the molecular weight of the polyoxypropylene portion of the respective block copolymer is 9,700 Daltons and the average total molecular weight of said substantially pure block copolymer composition is 10,000 Daltons.

110. A substantially pure polyoxypropylene/ polyoxyethylene block copolymer composition of claim 35, wherein a is an integer such that the molecular weight of the polyoxypropylene portion of the respective block copolymer is 3,400 Daltons and the average total molecular weight of said substantially pure block copolymer composition is 4,000 Daltons.

111. A substantially pure polyoxypropylene/ polyoxyethylene block copolymer composition of claim 35, wherein a is an integer such that the molecular weight of the polyoxypropylene portion of the respective block copolymer is between 950 Daltons and 4,000 Daltons and b is an integer such that the molecular weight represented by polyoxyethylene portion of the respective block copolymer constitutes between 50% and 95% of the respective block copolymer.

112. A substantially pure polyoxypropylene/ polyoxyethylene block copolymer composition of claim 35, wherein the average total molecular weight of said substantially pure block copolymer composition is between 5,000 Daltons and 15,000 Daltons and a is an integer such that the molecular weight represented by the polyoxypropylene portion of the respective block copolymer constitutes between 15% and 25% of the respective block copolymer.

113. A substantially pure polyoxypropylene/ polyoxyethylene block copolymer composition of claim 35, wherein the average total molecular weight of said substantially pure block copolymer composition is between 1,200 Daltons and 5,300 Daltons and a is an integer such that the molecular weight represented by the polyoxypropylene portion of the respective block copolymer constitutes between 10% and 50% of the respective block copolymer.

114. A substantially pure polyoxypropylene/ polyoxyethylene block copolymer composition of claim 113, wherein the average total molecular weight of said substantially pure block copolymer composition is between 1,750 Daltons and 4,500 Daltons.

115. A substantially pure polyoxypropylene/ polyoxyethylene block copolymer composition of claim 35, wherein the average total molecular weight of said substantially pure block copolymer composition is between 1,000 Daltons and 2,600 Daltons and a is an integer such that the molecular weight represented by the polyoxypropylene portion of the respective block copolymer constitutes 20% of the respective block copolymer.

116. A substantially pure polyoxypropylene/ polyoxyethylene block copolymer composition of claim 115, wherein the average total molecular weight of said substantially pure block copolymer composition is between 1,200 Daltons and 2,400 Daltons.

117. A substantially pure polyoxypropylene/ polyoxyethylene block copolymer composition of claim 36, wherein the polyoxypropylene portion of the respective block copolymer has a molecular weight range of between 1,200 Daltons and 6,500 Daltons.

118. A substantially pure polyoxypropylene/ polyoxyethylene block copolymer composition of claim 36, wherein the polyoxyethylene portion of the respective block copolymer constitutes between 10% and 95% of the respective block copolymer.

119. A substantially pure polyoxypropylene/ polyoxyethylene block copolymer composition of claim 36, wherein the polyoxyethylene portion of the respective block copolymer constitutes between 5% and 15% of the respective block copolymer.

120. A substantially pure polyoxypropylene/ polyoxyethylene block copolymer composition of claim 36, wherein the polyoxyethylene portion of the respective block copolymer constitutes 20% of the respective block copolymer.

121. A substantially pure polyoxypropylene/ polyoxyethylene block copolymer composition of claim 36, wherein a and b are selected such that the average total molecular weight of said substantially pure block copolymer composition is between 5,000 Daltons and 15,000 Daltons.

122. A substantially pure polyoxypropylene/ polyoxyethylene block copolymer composition of claim 117, wherein a and b are selected such that the average total molecular weight of said substantially pure block copolymer composition is between 5,000 Daltons and 15,000 Daltons.

123. A substantially pure polyoxypropylene/ polyoxyethylene block copolymer composition of claim 118, wherein a and b are selected such that the average total molecular weight of said substantially pure block copolymer composition is between 5,000 Daltons and 15,000 Daltons.

124. A substantially pure polyoxypropylene/ polyoxyethylene block copolymer composition of claim 120, wherein a and b are selected such that the average total molecular weight of said substantially pure block copolymer composition is between 5,000 Daltons and 15,000 Daltons.

125. A substantially pure polyoxypropylene/ polyoxyethylene block copolymer composition of claim 119, wherein the average total molecular weight of said substantially pure block copolymer composition is between 3,000 Daltons and 5,500 Daltons.

126. A substantially pure polyoxypropylene/ polyoxyethylene block copolymer composition of claim 119, wherein the average total molecular weight of said substantially pure block copolymer composition is between 4,500 Daltons and 5,500 Daltons.

127. A substantially pure polyoxypropylene/ polyoxyethylene block copolymer composition of claim 36, wherein a is an integer such that the molecular weight of the polyoxypropylene portion of the respective block copolymer is 1,750 Daltons and the average total molecular weight of said substantially pure block copolymer composition is between 8,300 Daltons and 9,400 Daltons.

128. A substantially pure polyoxypropylene/ polyoxyethylene block copolymer composition of claim 36, wherein a is an integer such that the molecular weight of the polyoxypropylene portion of the respective block copolymer is 1,750 Daltons and the average total molecular weight of said substantially pure block copolymer composition is 8,400 Daltons.

129. A substantially pure polyoxypropylene/ polyoxyethylene block copolymer composition of claim 117, wherein a is an integer such that the molecular weight of the polyoxypropylene portion of the respective block copolymer is 1,750 Daltons and the average total molecular weight of said substantially pure block copolymer composition is 8,400 Daltons.

130. A substantially pure polyoxypropylene/ polyoxyethylene block copolymer composition of claim 118, wherein a is an integer such that the molecular weight of the polyoxypropylene portion of the respective block copolymer is 1,750 Daltons and the average total molecular weight of said substantially pure block copolymer composition is 8,400 Daltons.

131. A substantially pure polyoxypropylene/ polyoxyethylene block copolymer composition of claim 120, wherein a is an integer such that the molecular weight of the polyoxypropylene portion of the respective block copolymer is 1,750 Daltons and the average total molecular weight of said substantially pure block copolymer composition is 8,400 Daltons.

132. A substantially pure polyoxypropylene/ polyoxyethylene block copolymer composition of claim 36, wherein the average total molecular weight of said substantially pure block copolymer composition is between 5,000 Daltons and 15,000 Daltons and b is an integer such that the molecular weight represented by the polyoxyethylene portion of the respective block copolymer constitutes between 75% and 85% of the respective block copolymer.

133. A substantially pure polyoxypropylene/ polyoxyethylene block copolymer composition of claim 132, wherein b is an integer such that the molecular weight represented by the polyoxyethylene portion of the respective block copolymer constitutes 80% of the respective block copolymer.

134. A substantially pure polyoxypropylene/ polyoxyethylene block copolymer composition of claim 36, wherein the average total molecular weight of said substantially pure block copolymer composition is between 7,000 and 12,000 Daltons.

135. A substantially pure polyoxypropylene/ polyoxyethylene block copolymer composition of claim 117, wherein the average total molecular weight of said substantially pure block copolymer composition is between 7,000 and 12,000 Daltons.

136. A substantially pure polyoxypropylene/ polyoxyethylene block copolymer composition of claim 118, wherein the average total molecular weight of said substantially pure block copolymer composition is between 7,000 and 12,000 Daltons.

137. A substantially pure polyoxypropylene/ polyoxyethylene block copolymer composition of claim 120, wherein the average total molecular weight of said substantially pure block copolymer composition is between 7,000 and 12,000 Daltons.

138. A substantially pure polyoxypropylene/ polyoxyethylene block copolymer composition of claim 133, wherein the average total molecular weight of said substantially pure block copolymer composition is between 7,000 and 12,000 Daltons.

139. A substantially pure polyoxypropylene/ polyoxyethylene block copolymer composition of claim 36, wherein a is an integer such that the molecular weight of the polyoxypropylene portion of the respective block copolymer is 9,700 Daltons and the average total molecular weight of said substantially pure block copolymer composition is 10,000 Daltons.

140. A substantially pure polyoxypropylene/ polyoxyethylene block copolymer composition of claim 36, wherein a is an integer such that the molecular weight of the polyoxypropylene portion of the respective block copolymer is 3,400 Daltons and the average total molecular weight of said substantially pure block copolymer composition is 4,000 Daltons.

141. A substantially pure polyoxypropylene/ polyoxyethylene block copolymer composition of claim 36, wherein a is an integer such that the molecular weight of the polyoxypropylene portion of the respective block copolymer is between 950 Daltons and 4,000 Daltons and b is an integer such that the molecular weight represented by polyoxeythylene portion of the respective block copolymer constitutes between 50% and 95% of the respective block copolymer.

142. A substantially pure polyoxypropylene/ polyoxyethylene block copolymer composition of claim 36, wherein the average total molecular weight of said substantially pure block copolymer composition is between 5,000 Daltons and 15,000 Daltons and a is an integer such that the molecular weight represented by the polyoxypropylene portion of the respective block copolymer constitutes between 15% and 25% of the respective block copolymer.

143. A substantially pure polyoxypropylene/ polyoxyethylene block copolymer composition of claim 36, wherein the average total molecular weight of said substantially pure block copolymer composition is between 1,200 Daltons and 5,300 Daltons and a is an integer such that the molecular weight represented by the polyoxypropylene portion of the respective block copolymer constitutes between 10% and 50% of the respective block copolymer.

144. A substantially pure polyoxypropylene/ polyoxyethylene block copolymer composition of claim 143, wherein the average total molecular weight of said substantially pure block copolymer composition is between 1,750 Daltons and 4,500 Daltons.

145. A substantially pure polyoxypropylene/ polyoxyethylene block copolymer composition of claim 36, wherein the average total molecular weight of said substantially pure block copolymer composition is between 1,000 Daltons and 2,600 Daltons and a is an integer such that the molecular weight represented by the polyoxypropylene portion of the respective block copolymer constitutes 20% of the respective block copolymer.

146. A substantially pure polyoxypropylene/ polyoxyethylene block copolymer composition of claim 145, wherein the average total molecular weight of said substantially pure block copolymer composition is between 1,200 Daltons and 2,400 Daltons.

147. A substantially pure polyoxypropylene/ polyoxyethylene block copolymer composition of claim 37, wherein the polyoxypropylene portion of the respective block copolymer has a molecular weight range of between 1,200 Daltons and 6,500 Daltons.

148. A substantially pure polyoxypropylene/ polyoxyethylene block copolymer composition of claim 37, wherein the polyoxyethylene portion of the respective block copolymer constitutes between 10% and 95% of the respective block copolymer.

149. A substantially pure polyoxypropylene/ polyoxyethylene block copolymer composition of claim 37, wherein the polyoxyethylene portion of the respective block copolymer constitutes between 5% and 15% of the respective block copolymer.

150. A substantially pure polyoxypropylene/ polyoxyethylene block copolymer composition of claim 37, wherein the polyoxyethylene portion of the respective block copolymer constitutes 20% of the respective block copolymer.

151. A substantially pure polyoxypropylene/ polyoxyethylene block copolymer composition of claim 37, wherein a and b are selected such that the average total molecular weight of said substantially pure block copolymer composition is between 5,000 Daltons and 15,000 Daltons.

152. A substantially pure polyoxypropylene/ polyoxyethylene block copolymer composition of claim 147, wherein a and b are selected such that the average total molecular weight of said substantially pure block copolymer composition is between 5,000 Daltons and 15,000 Daltons.

153. A substantially pure polyoxypropylene/ polyoxyethylene block copolymer composition of claim 148, wherein a and b are selected such that the average total molecular weight of said substantially pure block copolymer composition is between 5,000 Daltons and 15,000 Daltons.

154. A substantially pure polyoxypropylene/ polyoxyethylene block copolymer composition of claim 150, wherein a and b are selected such that the average total molecular weight of said substantially pure block copolymer composition is between 5,000 Daltons and 15,000 Daltons.

155. A substantially pure polyoxypropylene/ polyoxyethylene block copolymer composition of claim 149, wherein the average total molecular weight of said substantially pure block copolymer composition is between 3,000 Daltons and 5,500 Daltons.

156. A substantially pure polyoxypropylene/ polyoxyethylene block copolymer composition of claim 149, wherein the average total molecular weight of said substantially pure block copolymer composition is between 4,500 Daltons and 5,500 Daltons.

157. A substantially pure polyoxypropylene/ polyoxyethylene block copolymer composition of claim 37, wherein a is an integer such that the molecular weight of the polyoxypropylene portion of the respective block copolymer is 1,750 Daltons and the average total molecular weight of said substantially pure block copolymer composition is between 8,300 Daltons and 9,400 Daltons.

158. A substantially pure polyoxypropylene/ polyoxyethylene block copolymer composition of claim 37, wherein a is an integer such that the molecular weight of the polyoxypropylene portion of the respective block copolymer is 1,750 Daltons and the average total molecular weight of said substantially pure block copolymer composition is 8,400 Daltons.

159. A substantially pure polyoxypropylene/ polyoxyethylene block copolymer composition of claim 147, wherein a is an integer such that the molecular weight of the polyoxypropylene portion of the respective block copolymer is 1,750 Daltons and the average total molecular weight of said substantially pure block copolymer composition is 8,400 Daltons.

160. A substantially pure polyoxypropylene/ polyoxyethylene block copolymer composition of claim 148, wherein a is an integer such that the molecular weight of the polyoxypropylene portion of the respective block copolymer is 1,750 Daltons and the average total molecular weight of said substantially pure block copolymer composition is 8,400 Daltons.

161. A substantially pure polyoxypropylene/ polyoxyethylene block copolymer composition of claim 150, wherein a is an integer such that the molecular weight of the polyoxypropylene portion of the respective block copolymer is 1,750 Daltons and the average total molecular weight of said substantially pure block copolymer composition is 8,400 Daltons.

162. A substantially pure polyoxypropylene/ polyoxyethylene block copolymer composition of claim 37, wherein the average total molecular weight of said substantially pure block copolymer composition is between 5,000 Daltons and 15,000 Daltons and b is an integer such that the molecular weight represented by the polyoxyethylene portion of the respective block copolymer constitutes between 75% and 85% of the respective block copolymer.

163. A substantially pure polyoxypropylene/ polyoxyethylene block copolymer composition of claim 162, wherein b is an integer such that the molecular weight represented by the polyoxyethylene portion of the respective block copolymer constitutes 80% of the respective block copolymer.

164. A substantially pure polyoxypropylene/ polyoxyethylene block copolymer composition of claim 37, wherein the average total molecular weight of said substantially pure block copolymer composition is between 7,000 and 12,000 Daltons.

165. A substantially pure polyoxypropylene/ polyoxyethylene block copolymer composition of claim 147, wherein the average total molecular weight of said substantially pure block copolymer composition is between 7,000 and 12,000 Daltons.

166. A substantially pure polyoxypropylene/ polyoxyethylene block copolymer composition of claim 148, wherein the average total molecular weight of said substantially pure block copolymer composition is between 7,000 and 12,000 Daltons.

167. A substantially pure polyoxypropylene/ polyoxyethylene block copolymer composition of claim 150, wherein the average total molecular weight of said substantially pure block copolymer composition is between 7,000 and 12,000 Daltons.

168. A substantially pure polyoxypropylene/ polyoxyethylene block copolymer composition of claim 163, wherein the average total molecular weight of said substantially pure block copolymer composition is between 7,000 and 12,000 Daltons.

169. A substantially pure polyoxypropylene/ polyoxyethylene block copolymer composition of claim 37, wherein a is an integer such that the molecular weight of the polyoxypropylene portion of the respective block copolymer is 9,700 Daltons and the average total molecular weight of said substantially pure block copolymer composition is 10,000 Daltons.

170. A substantially pure polyoxypropylene/ polyoxyethylene block copolymer composition of claim 37, wherein a is an integer such that the molecular weight of the polyoxypropylene portion of the respective block copolymer is 3,400 Daltons and the average total molecular weight of said substantially pure block copolymer composition is 4,000 Daltons.

171. A substantially pure polyoxypropylene/ polyoxyethylene block copolymer composition of claim 37, wherein a is an integer such that the molecular weight of the polyoxypropylene portion of the respective block copolymer is between 950 Daltons and 4,000 Daltons and b is an integer such that the molecular weight represented by polyoxeythylene portion of the respective block copolymer constitutes between 50% and 95% of the respective block copolymer.

172. A substantially pure polyoxypropylene/ polyoxyethylene block copolymer composition of claim 37, wherein the average total molecular weight of said substantially pure block copolymer composition is between 5,000 Daltons and 15,000 Daltons and a is an integer such that the molecular weight represented by the polyoxypropylene portion of the respective block copolymer constitutes between 15% and 25% of the respective block copolymer.

173. A substantially pure polyoxypropylene/ polyoxyethylene block copolymer composition of claim 37, wherein the average total molecular weight of said substantially pure block copolymer composition is between 1,200 Daltons and 5,300 Daltons and a is an integer such that the molecular weight represented by the polyoxypropylene portion of the respective block copolymer constitutes between 10% and 50% of the respective block copolymer.

174. A substantially pure polyoxypropylene/ polyoxyethylene block copolymer composition of claim 173, wherein the average total molecular weight of said substantially pure block copolymer composition is between 1,750 Daltons and 4,500 Daltons.

175. A substantially pure polyoxypropylene/ polyoxyethylene block copolymer composition of claim 37, wherein the average total molecular weight of said substantially pure block copolymer composition is between 1,000 Daltons and 2,600 Daltons and a is an integer such that the molecular weight represented by the polyoxypropylene portion of the respective block copolymer constitutes 20% of the respective block copolymer.

176. A substantially pure polyoxypropylene/ polyoxyethylene block copolymer composition of claim 175, wherein the average total molecular weight of said substantially pure block copolymer composition is between 1,200 Daltons and 2,400 Daltons.

* * * * *